United States Patent
Wang et al.

(10) Patent No.: US 8,883,771 B2
(45) Date of Patent: Nov. 11, 2014

(54) BIVALENT INHIBITORS OF IAP PROTEINS AND THERAPEUTIC METHODS USING THE SAME

(71) Applicant: The Regents of the University of Michigan, Ann Arbor, MI (US)

(72) Inventors: Shaomeng Wang, Saline, MI (US); Rong Sheng, Ann Arbor, MI (US); Haiying Sun, Ann Arbor, MI (US); Liu Liu, Ann Arbor, MI (US); Jianfeng Lu, Ann Arbor, MI (US); Donna McEachern, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 13/969,030

(22) Filed: Aug. 16, 2013

(65) Prior Publication Data
US 2014/0057924 A1    Feb. 27, 2014

Related U.S. Application Data

(60) Provisional application No. 61/692,429, filed on Aug. 23, 2012.

(51) Int. Cl.
| | |
|---|---|
| C07D 225/00 | (2006.01) |
| A61K 31/545 | (2006.01) |
| C07D 519/00 | (2006.01) |
| A61K 31/407 | (2006.01) |
| A61K 31/496 | (2006.01) |
| A61K 45/06 | (2006.01) |

(52) U.S. Cl.
CPC ............ *C07D 519/00* (2013.01); *A61K 31/407* (2013.01); *A61K 31/496* (2013.01); *A61K 45/06* (2013.01)
USPC .......................................... 514/183; 540/460

(58) Field of Classification Search
USPC .......................................... 540/460; 514/183
See application file for complete search history.

(56) References Cited

U.S. PATENT DOCUMENTS

| 7,960,372 B2 | 6/2011 | Wang et al. |
| 2005/0197403 A1 | 9/2005 | Harran et al. |

*Primary Examiner* — Bruck Kifle
(74) *Attorney, Agent, or Firm* — Marshall, Gerstein & Borun LLP

(57) ABSTRACT

Inhibitors of IAP proteins and compositions containing the same are disclosed. Methods of using the IAP protein inhibitors in the treatment of diseases and conditions wherein inhibition of IAP proteins provides a benefit, like cancers, also are disclosed.

22 Claims, 1 Drawing Sheet

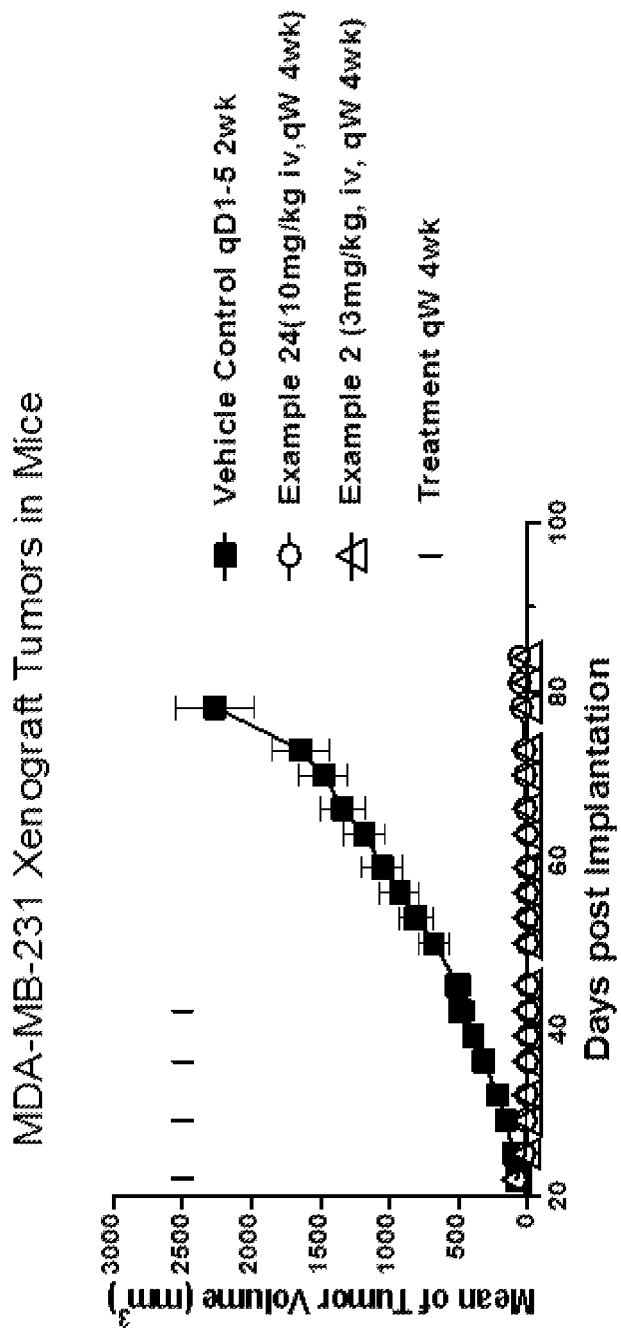

US 8,883,771 B2

BIVALENT INHIBITORS OF IAP PROTEINS AND THERAPEUTIC METHODS USING THE SAME

CROSS-REFERENCE TO RELATED APPLICATIONS

This application claims the benefit of U.S. provisional patent application No. 61/692,429 filed Aug. 23, 2012, incorporated herein by reference in its entirety.

GOVERNMENT FUNDING

This invention was made with government support under Grant Nos. CA127551 and CA109025 awarded by National Institutes of Health. The government has certain rights in the invention.

FIELD OF THE INVENTION

The present invention relates to bivalent inhibitors of Inhibitors of Apoptosis Proteins (IAPs) and to therapeutic methods of treating conditions and diseases wherein inhibition of IAP proteins provides a benefit. The present inhibitors bind to IAP proteins, including cIAP1, cIAP2, and XIAP, with very high affinities to induce apoptosis in human cancer cell lines to enhance the antitumor activity of other anticancer drugs.

BACKGROUND OF THE INVENTION

Apoptosis, or programmed cell death, is a cell process critical for homeostasis, normal development, host defense, and suppression of oncogenesis. Faulty regulation of apoptosis has been implicated in many human diseases,[1] including cancer,[1],[3] and it is now recognized that resistance to apoptosis is a hallmark of cancer.[4] As a consequence, targeting of key apoptosis regulators has emerged as an attractive strategy for the development of new approaches to human cancer treatment.[1]

Most current cancer therapies, including chemotherapeutic agents, radiation, and immunotherapy, indirectly induce apoptosis in cancer cells. The inability of cancer cells to execute an apoptotic program due to defects in the normal apoptotic machinery is thus often associated with an increase in resistance to chemotherapy, radiation, or immunotherapy-induced apoptosis. Such primary or acquired resistance of human cancers to current therapies due to apoptosis defects is a major problem in current cancer therapy.

In order to improve survival and quality of life of cancer patients, current and future efforts in the design and development of new molecular target-specific anticancer therapies includes strategies that specifically target cancer cell resistance to apoptosis. In this regard, targeting negative regulators that play a central role in directly inhibiting apoptosis in cancer cells represents a highly promising therapeutic strategy for new anticancer drug design.

One class of central negative regulators of apoptosis is the Inhibitors of Apoptosis Proteins (IAPs). This class includes proteins such as XIAP, cIAP1, cIAP2, ML-IAP, HIAP, KIAP, TSIAP, NAIP, survivin, livin, ILP-2, apollon, and BRUCE. IAP proteins potently suppress cancer cell apoptosis induced by a large variety of apoptotic stimuli, including chemotherapeutic agents, radiation, and immunotherapy.

Although their roles are not limited to regulation of apoptosis,[7],[8] IAP proteins are a class of key apoptosis regulators, and are characterized by the presence of one or more BIR (Baculoviral IAP Repeat) domains.[5]-[6] Among the IAPs, cellular IAP1 (cIAP1) and cIAP2 play a key role in the regulation of death-receptor mediated apoptosis, whereas X-linked IAP (XIAP) inhibits both death-receptor mediated and mitochondria mediated apoptosis by binding to and inhibiting caspase-3/7 and caspase-9, three cysteine proteases critical for execution of apoptosis.[5] These IAP proteins are highly overexpressed both in cancer cell lines and in human tumor tissues and have low expression in normal cells and tissues.[9] Extensive studies have demonstrated that overexpression of IAP proteins make cancer cells resistant to apoptosis induction by a variety of anticancer drugs.[10]-[12] A detailed discussion of IAP proteins and their role is cancer and apoptosis is set forth in U.S. Pat. No. 7,960,372, incorporated herein by reference. Hence, targeting one or more of these IAP proteins is a promising therapeutic strategy for the treatment of human cancer.[10]-[12]

Studies have shown that peptide-based inhibitors are useful tools to elucidate the anti-apoptotic function of IAPs and the role of IAPs in the response of cancer cells to chemotherapeutic agents. However, peptide-based inhibitors have intrinsic limitations as useful therapeutic agents, including a poor cell permeability and poor in vivo stability. In published studies using Smac-based peptide inhibitors, the peptides had to be fused to carrier peptides to make them relatively cell-permeable.

Small molecule inhibitors of IAP proteins also are known. For example, U.S. Patent Publication Application No. 2005/0197403 and U.S. Pat. No. 7,960,372 disclose dimeric Smac mimetic compounds, each incorporated herein by reference in its entirety.

Despite the discovery of small molecule inhibitors of IAP proteins, the design of potent, non-peptide inhibitors of IAP proteins remains a significant challenge in modern drug discovery. Accordingly, a need still exists in the art for IAP inhibitors having physical and pharmacological properties that permit use of the inhibitors in therapeutic applications. The present invention provides compounds designed to bind to IAP proteins and inhibit IAP protein activity.

SUMMARY OF THE INVENTION

It is generally accepted that the inability of cancer cells or their supporting cells to undergo apoptosis in response to genetic lesions or exposure to inducers of apoptosis (such as chemotherapeutic agents and radiation) is a major factor in the onset and progression of cancer. The induction of apoptosis in cancer cells or their supporting cells (e.g., neovascular cells in the tumor vasculature) is considered a universal mechanism of action for virtually all the effective cancer therapeutic drug and radiation therapies in practice today. One reason for the inability of a cell to undergo apoptosis is an increased expression and accumulation of IAPs.

The present invention therefore is directed to inhibitors of IAP proteins, to compositions comprising the inhibitors, and to methods of using the inhibitors in a therapeutic treatment of conditions and diseases wherein inhibition of IAP protein activity provides a benefit. The present compounds are potent inhibitors of IAP protein activation, and induce apoptosis of cancer cells.

BRIEF DESCRIPTION OF THE DRAWING

FIG. 1 is a plot of Mean Tumor Volume ($mm^3$) vs. Days Past Implantation showing the antitumor activity of Examples 2 and 24 in the MDA-MB-231 xenograft model in nude mice.

More particularly, the present invention is directed to compounds having a structural formula (I):

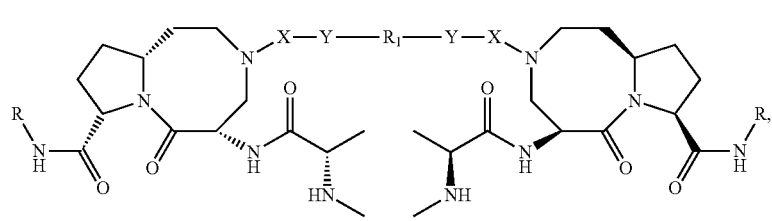

(I)

wherein X is selected from the group consisting of

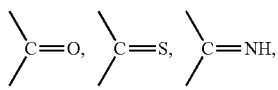

and —SO$_2$—;

Y is selected from the group consisting of —NH—, —O—, —S—, and null;

R is selected from the group consisting of

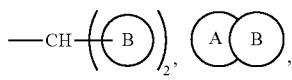

wherein ring A is a C$_{4-8}$ aliphatic ring,

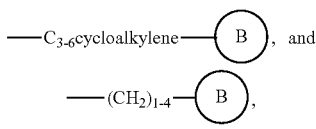

wherein the B ring is aryl or nitrogen atom-containing heteroaryl and the B rings are optionally substituted; and R$_1$ is selected from the group consisting of —(CH$_2$)$_{4-10}$—,

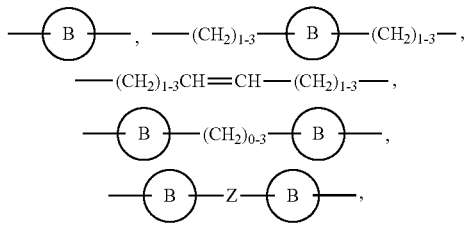

wherein Z is O, S, or NH, and

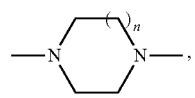

wherein n is 0, 1, or 2, and wherein the B ring is aryl or nitrogen atom-containing heteroaryl and the

rings are optionally substituted;

or a pharmaceutically acceptable salt, hydrate, solvate, or prodrug thereof.

In one embodiment, the present invention provides compounds that inhibit the activity of IAP proteins and increase the sensitivity of cells to inducers of apoptosis, such as an chemotherapeutic agents and radiation therapy.

In other embodiments, the present compounds are used in methods to induce apoptosis in cells and to sensitize cells to inducers of apoptosis.

In still another embodiment, the present invention provides a method of treating a condition or disease by administering a therapeutically effective amount of a compound of structural formula (I) to an individual in need thereof. The disease or condition of interest is treatable by inhibition of IAP proteins, for example, a cancer. The present compounds therefore are useful for the treatment and amelioration of disorders responsive to induction of apoptotic cell death, e.g., disorders characterized by dysregulation of apoptosis, including hyperproliferative diseases, such as cancer. In certain embodiments, the compounds can be used to treat and ameliorate a cancer that is characterized by resistance to cancer therapies (e.g., are chemoresistant, radiation resistant, hormone resistant, and the like). In other embodiments, the present compounds can be used to treat hyperproliferative diseases characterized by overexpression of IAPs.

Another embodiment of the present invention is to provide a composition comprising (a) an IAP inhibitor of structural formula (I) and (b) an excipient and/or pharmaceutically acceptable carrier useful in treating diseases or conditions wherein inhibition of IAP proteins provides a benefit.

Another embodiment of the present invention is to utilize a composition comprising a compound of structural formula (I) and a second therapeutically active agent in a method of treating an individual for a disease or condition wherein inhibition of IAP proteins provides a benefit.

In a further embodiment, the invention provides for use of a composition comprising a IAP protein inhibitor of structural formula (I) and an optional second therapeutic agent for the manufacture of a medicament for treating a disease or condition of interest, e.g., a cancer.

Still another embodiment of the present invention is to provide a kit for human pharmaceutical use comprising (a) a container, (b1) a packaged composition comprising an IAP protein inhibitor of structural formula (I), and, optionally, (b2) a packaged composition comprising a second therapeutic agent useful in the treatment of a disease or condition of interest, and (c) a package insert containing directions for use of the composition or compositions, administered simultaneously or sequentially, in the treatment of the disease or condition.

An IAP protein inhibitor of structural formula (I) and the second therapeutic agent can be administered together as a single-unit dose or separately as multi-unit doses, wherein the IAP inhibitor of structural formula (I) is administered before the second therapeutic agent or vice versa. It is envisioned that one or more dose of an IAP inhibitor of structural formula (I) and/or one or more dose of a second therapeutic agent can be administered.

In one embodiment, an IAP protein inhibitor of structural formula (I) and a second therapeutic agent are administered simultaneously. In related embodiments, the IAP protein inhibitor of structural formula (I) and second therapeutic agent are administered from a single composition or from separate compositions. In a further embodiment, the IAP protein inhibitor of structural formula (I) and second therapeutic agent are administered sequentially. An IAP protein inhibitor of structural formula (I), as used in the present invention, can be administered in an amount of about 0.005 to about 500 milligrams per dose, about 0.05 to about 250 milligrams per dose, or about 0.5 to about 100 milligrams per dose.

DETAILED DESCRIPTION OF THE PREFERRED EMBODIMENTS

The present invention is described in connection with preferred embodiments. However, it should be appreciated that the invention is not limited to the disclosed embodiments. It is understood that, given the description of the embodiments of the invention herein, various modifications can be made by a person skilled in the art. Such modifications are encompassed by the claims below.

Smac/DIABLO (second mitochondria-derived activator of caspases or direct IAP binding protein with low pI) is a protein released from mitochondria in response to apoptotic stimuli and functions as an endogenous inhibitor of cIAP1, cIAP2 and XIAP.[14],[15] The interaction between Smac and IAPs is mediated by the N-terminal AVPI tetrapeptide motif in Smac and one or more BIR domains in these IAP proteins.[16],[17] Smac is a homodimer which binds to both the BIR2 and BIR3 domains in XIAP and antagonizes the inhibition of XIAP to caspase-3/-7 and caspase-9.[18] In comparison, Smac binds to only the BIR3 domain in cIAP1 and cIAP2[19] and induces rapid proteins degradation in cells.[20] Through two distinct mechanisms, Smac is a very efficient antagonist of these three IAP proteins.

The crystal and NMR structures of XIAP BIR3 complexed with Smac protein or Smac peptide show that the AVPI tetrapeptide motif in Smac binds to a well-defined surface groove in XIAP and this interaction represents an attractive site for the design of small-molecule XIAP inhibitors.[16]-[18] By use of AVPI tetrapeptide as the lead structure, several classes of small-molecule Smac mimetics have been designed as antagonists of XIAP and cIAP1/2.[21]-[38] Two different types of Smac mimetics have been designed.[21]-[23] The first type, designed to mimic a single AVPI binding motif, is called monovalent Smac mimetics.[21]-[23] The second type, the bivalent Smac mimetics, consists of two AVPI mimetics, tethered through a linker, to mimic the dimeric form of Smac proteins.[21]-[23]

One advantage of monovalent Smac mimetics as potential drugs is an oral bioavailability, but a drawback is a modest potency in antagonizing full-length XIAP in functional assays. A major advantage of bivalent Smac mimetics is that they are much more potent antagonists of XIAP than monovalent Smac mimetics by concurrently targeting both BIR2 and BIR3 domains in XIAP.[30] Bivalent Smac mimetics typically are 2-3 orders of magnitude more potent than their monovalent Smac mimetic counterparts in induction of apoptosis in cancer cells.[21] Currently, three monovalent and two bivalent Smac mimetics have advanced into clinical trials for the treatment of human cancer.[21]

Because bivalent Smac mimetics are significantly more potent than monovalent Smac mimetics in targeting XIAP and cIAP1/2, in induction of apoptosis of cancer cells in vitro and in vivo, and in inhibition of tumor growth, the present bivalent compounds have been designed for use in cancer treatment and the treatment of other diseases and conditions mediated by IAP protein activity.

The term "IAP proteins," as used herein, refers to any known member of the Inhibitors of Apoptosis Protein family, including, but not limited to, XIAP, cIAP-1, cIAP-2, ML-IAP, HIAP, TSIAP, KIAP, NAIP, survivin, livin, ILP-2, apollon, and BRUCE.

The term "overexpression of IAPs," as used herein, refers to an elevated level (e.g., aberrant level) of mRNAs encoding for an IAP protein(s), and/or to elevated levels of IAP protein(s) in cells as compared to similar corresponding non-pathological cells expressing basal levels of mRNAs encoding IAP proteins or having basal levels of IAP proteins. Methods for detecting the levels of mRNAs encoding IAP proteins or levels of IAP proteins in a cell include, but are not limited to, Western blotting using IAP protein antibodies, immunohistochemical methods, and methods of nucleic acid amplification or direct RNA detection. As important as the absolute level of IAP proteins in cells is to determining that they overexpress IAP proteins, so also is the relative level of IAP proteins to other pro-apoptotic signaling molecules (e.g., pro-apoptotic Bcl-2 family proteins) within such cells. When the balance of these two are such that, were it not for the levels of the IAP proteins, the pro-apoptotic signaling molecules would be sufficient to cause the cells to execute the apoptosis program and die, said cells would be dependent on the IAP proteins for their survival. In such cells, exposure to an inhibiting effective amount of an IAP protein inhibitor will be sufficient to cause the cells to execute the apoptosis program and die. Thus, the term "overexpression of an IAP protein" also refers to cells that, due to the relative levels of pro-apoptotic signals and anti-apoptotic signals, undergo apoptosis in response to inhibiting effective amounts of compounds that inhibit the function of IAP proteins.

The term "a disease or condition wherein inhibition of an IAP protein provides a benefit" pertains to a condition in which an IAP protein, and/or an action of an IAP protein, is important or necessary, e.g., for the onset, progress, expression of that disease or condition, or a disease or a condition which is known to be treated by an IAP protein inhibitor. An example of such a condition includes, but is not limited to, a cancer. One of ordinary skill in the art is readily able to determine whether a compound treats a disease or condition mediated by an IAP protein for any particular cell type, for example, by assays which conveniently can be used to assess the activity of particular compounds.

The term "second therapeutic agent" refers to a therapeutic agent different from an IAP inhibitor of structural formula (I) and that is known to treat the disease or condition of interest. For example when a cancer is the disease or condition of interest, the second therapeutic agent can be a known chemotherapeutic drug, like taxol, or radiation, for example.

The term "disease" or "condition" denotes disturbances and/or anomalies that as a rule are regarded as being pathological conditions or functions, and that can manifest themselves in the form of particular signs, symptoms, and/or malfunctions. As demonstrated below, a compound of structural formula (I) is a potent inhibitor of IAP proteins and can be used in treating diseases and conditions wherein inhibition an IAP protein provides a benefit.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound of the invention to an individual in need of such treatment.

Within the meaning of the invention, "treatment" also includes relapse prophylaxis or phase prophylaxis, as well as the treatment of acute or chronic signs, symptoms and/or malfunctions. The treatment can be orientated symptomatically, for example, to suppress symptoms. It can be effected over a short period, be oriented over a medium term, or can be a long-term treatment, for example within the context of a maintenance therapy.

The terms "sensitize" and "sensitizing," as used herein, refer to making, through the administration of a first agent (e.g., a compound of structural formula I), an animal or a cell within an animal more susceptible, or more responsive, to the biological effects (e.g., promotion or retardation of an aspect of cellular function including, but not limited to, cell division, cell growth, proliferation, invasion, angiogenesis, or apoptosis) of a second agent. The sensitizing effect of a first agent on a target cell can be measured as the difference in the intended biological effect (e.g., promotion or retardation of an aspect of cellular function including, but not limited to, cell growth, proliferation, invasion, angiogenesis, or apoptosis) observed upon the administration of a second agent with and without administration of the first agent. The response of the sensitized cell can be increased by at least 10%, at least 20%, at least 30%, at least 40%, at least 50%, at least 60%, at least 70%, at least 80%, at least 90%, at least 100%, at least 150%, at least 200%, at least 350%, at least 300%, at least 350%, at least 400%, at least 450%, or at least 500% over the response in the absence of the first agent.

The term "hyperproliferative disease," as used herein, refers to any condition in which a localized population of proliferating cells in an animal is not governed by the usual limitations of normal growth. Examples of hyperproliferative disorders include, but are not restricted to tumors, neoplasms, lymphomas and the like. A neoplasm is said to be benign if it does not undergo invasion or metastasis, and malignant if it does either of these. A "metastatic" cell means that the cell can invade and destroy neighboring body structures. Hyperplasia is a form of cell proliferation involving an increase in cell number in a tissue or organ without significant alteration in structure or function. Metaplasia is a form of controlled cell growth in which one type of fully differentiated cell substitutes for another type of differentiated cell.

The pathological growth of activated lymphoid cells often results in an autoimmune disorder or a chronic inflammatory condition. As used herein, the term "autoimmune disorder" refers to any condition in which an organism produces antibodies or immune cells which recognize the organism's own molecules, cells, or tissues. Nonlimiting examples of autoimmune disorders include autoimmune hemolytic anemia, autoimmune hepatitis, Berger's disease or IgA nephropathy, celiac sprue, chronic fatigue syndrome, Crohn's disease, dermatomyositis, fibromyalgia, graft versus host disease, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjögren's syndrome, systemic lupus erythematosus, type 1 diabetes, ulcerative colitis, vitiligo, and the like.

The term "neoplastic disease," as used herein, refers to any abnormal growth of cells being either benign (non-cancerous) or malignant (cancerous).

The term "anti-neoplastic agent," as used herein, refers to any compound that retards the proliferation, growth, or spread of a targeted (e.g., malignant) neoplasm.

The term "apoptosis-modulating agents," as used herein, refers to agents which are involved in modulating (e.g., inhibiting, decreasing, increasing, promoting) apoptosis. Examples of apoptosis-modulating agents include proteins which comprise a death domain such as, but not limited to, Fas/CD95, TRAMP, TNF RI, DR1, DR2, DR3, DR4, DR5, DR6, FADD, and RIP. Other examples of apoptotic-modulating agents include, but are not limited to, TNFα, Fas ligand, antibodies to Fas/CD95 and other TNF family receptors, TRAIL (also known as Apo2 Ligand or Apo2L/TRAIL), agonists (e.g., monoclonal or polyclonal agonistic antibodies) of TRAIL-R1 or TRAIL-R2, Bcl-2, p53, BAX, BAD, Akt, CAD, PI3 kinase, PP1, and caspase proteins. Modulating agents broadly include agonists and antagonists of TNF family receptors and TNF family ligands. Apoptosis-modulating agents may be soluble or membrane bound (e.g. ligand or receptor). Preferred apoptosis-modulating agents are inducers of apoptosis, such as TNF or a TNF-related ligand, particularly a TRAMP ligand, a Fas/CD95 ligand, a TNFR-1 ligand, or TRAIL.

The term "dysregulation of apoptosis," as used herein, refers to any aberration in the ability of (e.g., predisposition) a cell to undergo cell death via apoptosis. Dysregulation of apoptosis is associated with or induced by a variety of conditions, including for example, autoimmune disorders (e.g., systemic lupus erythematosus, rheumatoid arthritis, graft-versus-host disease, myasthenia gravis, or Sjögren's syndrome), chronic inflammatory conditions (e.g., psoriasis, asthma or Crohn's disease), hyperproliferative disorders (e.g., tumors, B cell lymphomas, or T cell lymphomas), viral infections (e.g., herpes, papilloma, or HIV), and other conditions such as osteoarthritis and atherosclerosis. It should be noted that when the dysregulation is induced by or associated with a viral infection, the viral infection may or may not be detectable at the time dysregulation occurs or is observed. That is, viral-induced dysregulation can occur even after the disappearance of symptoms of viral infection.

The term "therapeutically effective amount" or "effective dose" as used herein refers to an amount of the active ingredient(s) that is(are) sufficient, when administered by a method of the invention, to efficaciously deliver the active ingredient(s) for the treatment of condition or disease of interest to an individual in need thereof. In the case of a cancer or other proliferation disorder, the therapeutically effective amount of the agent may reduce (i.e., retard to some extent and preferably stop) unwanted cellular proliferation; reduce the number of cancer cells; reduce the tumor size; inhibit (i.e., retard to some extent and preferably stop) cancer cell infiltration into peripheral organs; inhibit (i.e., retard to some extent and preferably stop) tumor metastasis; inhibit, to some extent, tumor growth; reduce TAP protein signaling in the target cells increase survival time; and/or relieve, to some extent, one or more of the symptoms associated with the cancer by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%. To the extent the administered compound or composition prevents growth and/or kills existing cancer cells, it may be cytostatic and/or cytotoxic.

The term "container" means any receptacle and closure therefor suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to an individual in a sequence and sufficiently close in time so as to provide the desired therapeutic effect and can act in concert. For example, an IAP protein inhibitor of structural formula (I) can be administered at the same time or sequentially in any order at different points in time as a second therapeutic agent. A present IAP protein inhibitor and the second therapeutic agent can be administered separately, in any appropriate form and by any suitable route. When a present IAP protein inhibitor and the second therapeutic agent are not administered concurrently, it is understood that they can be administered in any order to a subject in need thereof. For example, a present IAP protein inhibitor can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent treatment modality (e.g., radiotherapy), to an individual in need thereof. In various embodiments, an IAP protein inhibitor of structural formula (I) and the second therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at 1 minute to 24 hours apart.

The use of the terms "a", "an", "the", and similar referents in the context of describing the invention (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the invention and is not a limitation on the scope of the invention unless otherwise claimed. No language in the specification should be construed as indicating any non-claimed element as essential to the practice of the invention.

The present invention is directed to compounds of structural formula (I), which are mimetics of Smac and function as inhibitors of IAPs proteins. The present compounds sensitize cells to inducers of apoptosis and, in some instances, themselves induce apoptosis by inhibiting IAPs proteins. Therefore, the invention relates to methods of sensitizing cells to inducers of apoptosis, and to methods of inducing apoptosis in cells, comprising contacting the cells with a compound of structural formula (I) alone or in combination with an inducer of apoptosis. The invention further relates to methods of treating or ameliorating disorders in an animal that are responsive to induction of apoptosis comprising administering to the animal a compound of structural formula (I) and an inducer of apoptosis. Such disorders include those characterized by a dysregulation of apoptosis and those characterized by overexpression of IAP proteins.

The present invention is directed to potent inhibitors of IAP proteins. The present IAP protein inhibitors are nonpeptidic, bivalent Smac mimetics that bind to XIAP, cIAP1, and cIAP2 with low to sub-nanomolar affinities and are highly effective in antagonizing XIAP in cell-free functional assays. The present compounds efficiently induce the degradation of cIAP1 and cIAP2 in cancer cells at low concentrations, activate caspase-3 and -8, and cleave PARP. The present compounds have a low $IC_{50}$ in inhibition of cell growth in both MDA-MB-231 and SK-OV-3 cell lines.

The IAP protein inhibitors of the present invention therefore are useful in the treatment of unwanted proliferating cells, including cancers and precancers, in subjects in need of such treatment. Also provided are methods of treating a subject having unwanted proliferating cells comprising administering a therapeutically effective amount of a present compound to a subject in need of such treatment. Also provided are methods of preventing the proliferation of unwanted proliferating cells, such as cancers and precancers, in a subject comprising the step of administering a therapeutically effective amount of a compound of structural formula (I) to a subject at risk of developing a condition characterized by unwanted proliferating cells. In some embodiments, the compounds of structural formula (I) reduced the proliferation of unwanted cells by inducing apotosis in those cells.

The present invention is directed to IAP protein inhibitors having a structural formula (I):

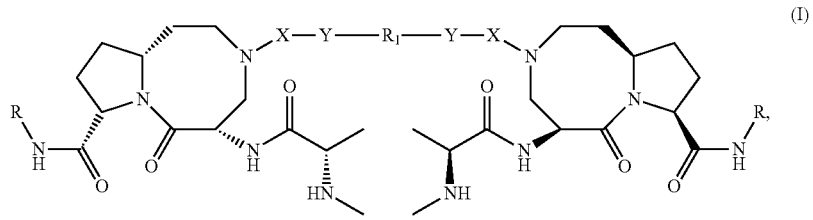

wherein X is selected from the group consisting of

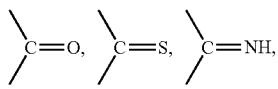

and —SO$_2$—;
Y is selected from the group consisting of —NH—, —O—, —S—, and null;
R is selected from the group consisting of

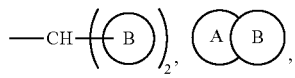

wherein ring A is a C$_{4-8}$ aliphatic ring,

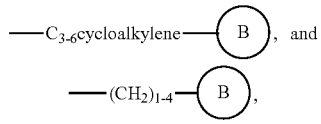

wherein the B ring is aryl or nitrogen atom-containing heteroaryl and the B rings are optionally substituted; and
R$_1$ is selected from the group consisting of —(CH$_2$)$_{4-10}$—,

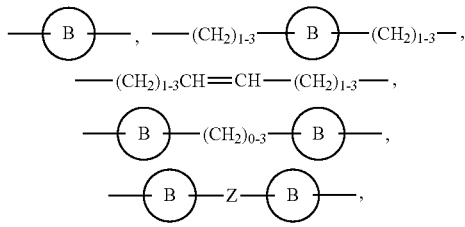

wherein Z is O, S, or NH, and

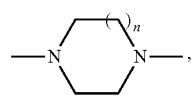

wherein n is 0, 1, or 2, and wherein the B ring is aryl or nitrogen atom-containing heteroaryl and the

rings are optionally substituted;
or a pharmaceutically acceptable salt, hydrate, solvate, or prodrug thereof.

As used herein, the term "C$_{4-8}$ aliphatic ring" refers to cyclobutyl, cyclopentyl, cyclohexyl, cycloheptyl, and cyclooctyl, either unsubstituted or substituted with 1 to 3 groups, for example, C$_{1-4}$alkyl, halo, trifluoromethyl, trifluoromethoxy, hydroxy, alkoxy, nitro, cyano, alkylamino, or amino groups.

As used herein, the term "alkyl" refers to straight chained and branched saturated C$_{1-10}$ hydrocarbon groups, nonlimiting examples of which include methyl, ethyl, and straight chain and branched propyl, butyl, pentyl, hexyl, heptyl, octyl, nonyl, and decyl groups. The term C$_n$ means the alkyl group has "n" carbon atoms.

The term "C$_{3-6}$cycloalkylene" refers to a disubstituted cycloalkane having 3 to 6 carbon atoms, for example

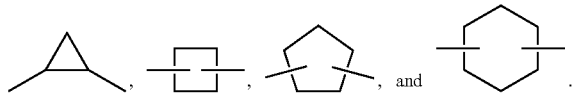

The "C$_{3-6}$cycloalkylene" can be unsubstituted, or substituted with 1 to 3 groups, for example, C$_{1-4}$alkyl, halo, trifluoromethyl, trifluoromethoxy, hydroxy, alkoxy, nitro, cyano, alkylamino, or amino groups.

The term "alkenyl" is defined identically as "alkyl," except for containing a carbon-carbon double bond, e.g., ethenyl, propenyl, and butenyl.

As used herein, the term "halo" is defined as fluoro, chloro, bromo, and iodo.

The term "hydroxy" is defined as —OH.
The term "alkoxy" is defined as —OR, wherein R is alkyl.
The term "amino" is defined as —NH$_2$, and the term "alkylamino" is defined as —NR$_2$, wherein at least one R is alkyl and the second R is alkyl or hydrogen.
The term "nitro" is defined as —NO$_2$.
The term "cyano" is defined as —CN.
The term "trifluoromethyl" is defined as —CF$_3$.
The term "trifluoromethoxy" is defined as —OCF$_3$.

As used herein, the term "aryl" refers to a monocyclic or polycyclic aromatic group, preferably a monocyclic or bicyclic aromatic group, e.g., phenyl or naphthyl. Unless otherwise indicated, an aryl group can be unsubstituted or substituted with one or more, and in particular one to four, groups independently selected from, for example, halo, alkyl, alkenyl, —OCF$_3$, —NO$_2$, —CN, —NC, —OH, alkoxy, amino, alkylamino, —CO$_2$H, —CO$_2$alkyl, alkynyl, cycloalkyl, nitro, sulfhydryl, imino, amido, phosphonate, phosphinate, silyl, alkylthio, sulfonyl, sulfonamide, aldehyde, heterocycloalkyl, trifluoromethyl, aryl, and heteroaryl.

As used herein, the term "heteroaryl" refers to a monocyclic or bicyclic ring system containing one or two aromatic rings and containing at least one and up to four nitrogen atoms in an aromatic ring. Unless otherwise indicated, a heteroaryl group can be unsubstituted or substituted with one or more, and in particular one to four, substituents selected from, for example, halo, alkyl, alkenyl, —OCF$_3$, —NO$_2$, —CN, —NC, —OH, alkoxy, amino, alkylamino, —CO$_2$H, —CO$_2$alkyl, alkynyl, cycloalkyl, nitro, sulfhydryl, imino, amido, phosphonate, phosphinate, silyl, alkylthio, sulfonyl, sulfonamide, aldehyde, heterocycloalkyl, trifluoromethyl, aryl, and heteroaryl.

The term "arylene" refers to a bidentate aryl group that bonds to two other groups and serves to connect these groups, e.g.,

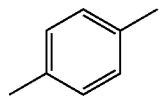

The term "heteroarylene" is similarly defined.

Nonlimiting examples of aryl groups are

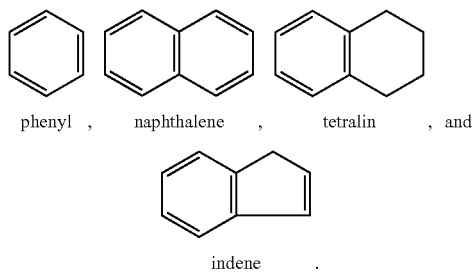

Nonlimiting examples of heteroaryl groups are

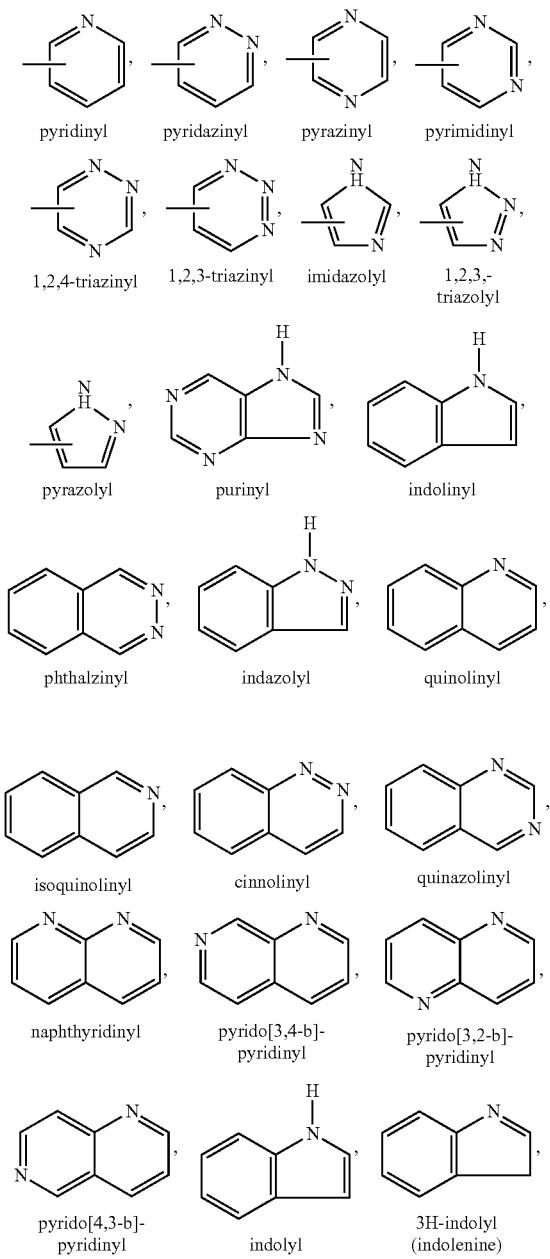

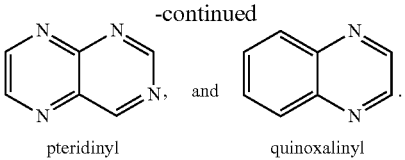

The compounds of structural formula (I) inhibit IAP proteins and are useful in the treatment of a variety of diseases and conditions. In particular, the compounds of structural formula (I) are used in methods of treating a disease or condition wherein inhibition of an IAP protein provides a benefit, for example, cancers, autoimmune disorders, and chronic inflammatory conditions. The method comprises administering a therapeutically effective amount of a compound of structural formula (I) to an individual in need thereof. The present methods also encompass administering a second therapeutic agent to the individual in addition to the compound of structural formula (I). The second therapeutic agent is selected from drugs known as useful in treating the disease or condition afflicting the individual in need thereof, e.g., a chemotherapeutic agent and/or radiation known as useful in treating a particular cancer.

In some preferred embodiments, the B ring is phenyl, naphthyl, pyridinyl, pyridazinyl, pyrazinyl, or pyrimidinyl.

In some preferred embodiments, R includes, but is not limited to:

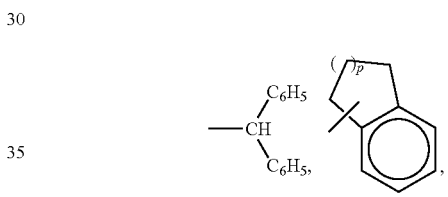

wherein p is 0 to 4,

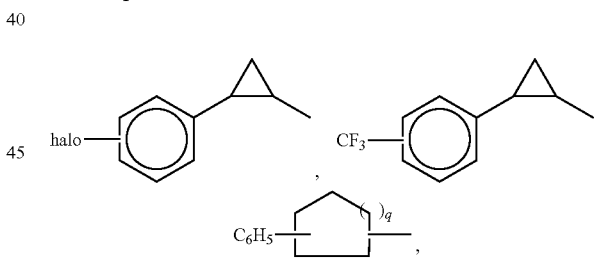

wherein q is 0 to 2, and —$(CH_2)_{2-4}$—$C_6H_5$.

Specific R groups include, but are not limited to:

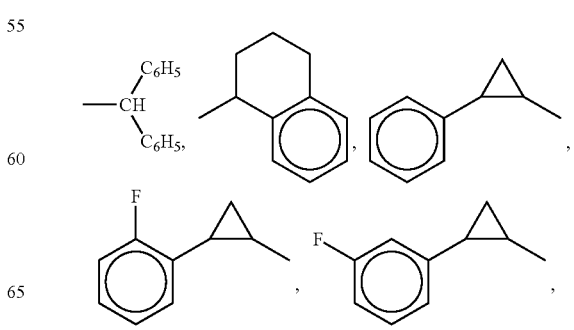

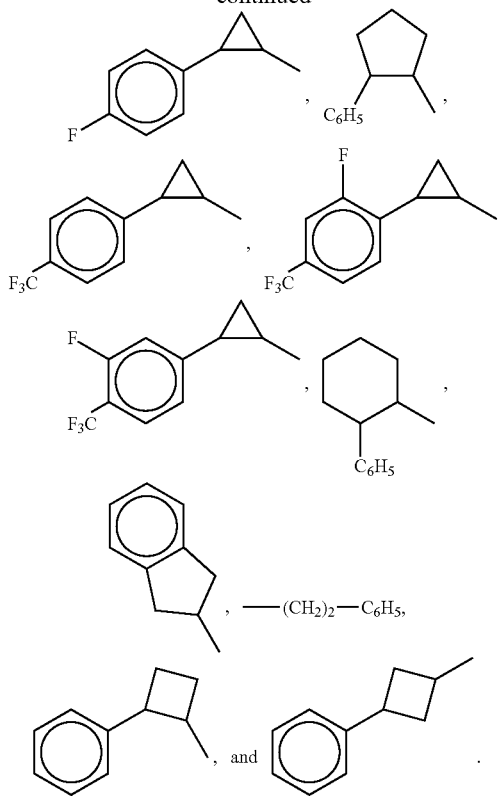

In some preferred embodiments $R_1$ is, but not limited to,

—$(CH_2)_{4-8}$—, —$(CH_2)_{4-8}$—,

—$(CH_2)_{1-2}$—⌬—$(CH_2)_{1-2}$—,

—$(CH_2)_{1-2}$—CH=CH—$(CH_2)_{1-2}$—, and wherein n is 0 or 1.

Specific $R_1$ groups include, but are not limited to,

—$(CH_2)_4$—, —$(CH_2)_6$—, —$(CH_2)_8$—,

—$CH_2$—⌬—$CH_2$—,

—$(CH_2)_2$—CH=CH—$(CH)_{1-2}$—,

In some preferred embodiments, X is $\underset{/}{\overset{\backslash}{C}}=O$ and Y is —NH—.

In other preferred embodiments, X is $SO_2$ and Y is null.

In another preferred embodiment, X is $\underset{/}{\overset{\backslash}{C}}=O$ and Y is null.

In still another preferred embodiment, X is $\underset{/}{\overset{\backslash}{C}}=S$ and Y is —NH—.

In still yet another preferred embodiment, X and X' are $\underset{/}{\overset{\backslash}{C}}=O$ and Y is —O—.

Additionally, salts, hydrates, solvates, and prodrugs of the present compounds also are included in the present invention and can be used in the methods disclosed herein. The present invention further includes all possible stereoisomers and geometric isomers of the compounds of structural formula (I). The present invention includes both racemic compounds and optically active isomers. When a compound of structural formula (I) is desired as a single enantiomer, it can be obtained either by resolution of the final product or by stereospecific synthesis from either isomerically pure starting material or use of a chiral auxiliary reagent, for example, see Z. Ma et al., *Tetrahedron: Asymmetry*, 8(6), pages 883-888 (1997). Resolution of the final product, an intermediate, or a starting material can be achieved by any suitable method known in the art. Additionally, in situations where tautomers of the compounds of structural formula (I) are possible, the present invention is intended to include all tautomeric forms of the compounds.

Compounds of the invention can exist as salts. Pharmaceutically acceptable salts of the compounds of the invention often are preferred in the methods of the invention. The term "pharmaceutically acceptable salt," as used herein, refers to any salt (e.g., obtained by reaction with an acid or a base) of a compound of the present invention that is physiologically tolerated in the target animal (e.g., a mammal). Salts of the compounds of the present invention may be derived from inorganic or organic acids and bases. The term "pharmaceutically acceptable salts" also refers to zwitterionic forms of the compounds of structural formula (I). Salts of compounds of formula (I) can be prepared during the final isolation and purification of the compounds or separately by reacting the compound with an acid having a suitable cation. The pharmaceutically acceptable salts of compounds of structural formula (I) can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Nonlimiting examples of salts of compounds of the invention include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulphonate, and p-toluenesulfonate salts. Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like. In addition, available amino groups present in the compounds of the invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides.

Compounds of structural formula (I) can contain one or more asymmetric center, and therefore can exist as stereoisomers. The present invention includes both mixtures and individual stereoisomers. In particular, the compounds of structural formula (I) include both the individual cis- and trans-isomers, and mixtures of the cis- and trans-isomers, e.g.,

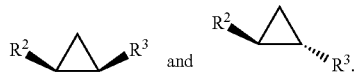

The term "prodrug," as used herein, refers to a pharmacologically inactive derivative of a parent "drug" molecule that requires biotransformation (e.g., either spontaneous or enzymatic) within the target physiological system to release, or to convert (e.g., enzymatically, physiologically, mechanically, electromagnetically) the prodrug into the active drug. Prodrugs are designed to overcome problems associated with stability, toxicity, lack of specificity, or limited bioavailability.

Prodrugs often offer advantages of solubility, tissue compatibility, or delayed release in the mammalian organism. (See e.g., Bundgard, "Design of Prodrugs", pp. 7-9, 21-24, Elsevier, Amsterdam (1985); and Silverman, "The Organic Chemistry of Drug Design and Drug Action", pp. 352-401, Academic Press, San Diego, Calif. (1992)). Exemplary prodrugs comprise an active drug molecule itself and a chemical masking group (e.g., a group that reversibly suppresses the activity of the drug). Some preferred prodrugs are variations or derivatives of compounds that have groups cleavable under metabolic conditions. Exemplary prodrugs become pharmaceutically active in vivo or in vitro when they undergo solvolysis under physiological conditions or undergo enzymatic degradation or other biochemical transformation (e.g., phosphorylation, hydrogenation, dehydrogenation, glycosylation). Common prodrugs include acid derivatives such as esters prepared by reaction of parent acids with a suitable alcohol (e.g., a lower alkanol), amides prepared by reaction of the parent acid compound with an amine, or basic groups reacted to form an acylated base derivative (e.g., a lower alkylamide).

Specific compounds of the present invention include, but are not limited to, compounds having the structure set forth below.

Structures

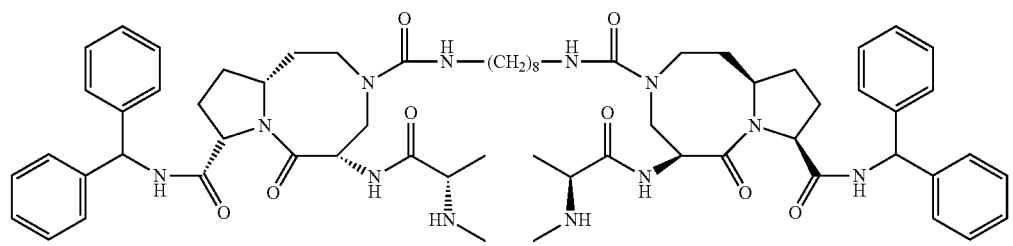

Example 1

-continued
Structures
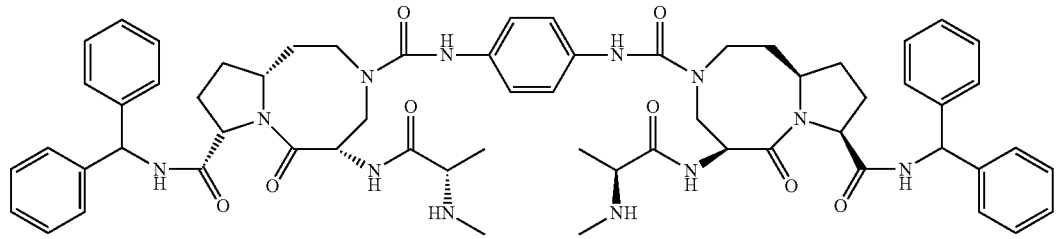
Example 2
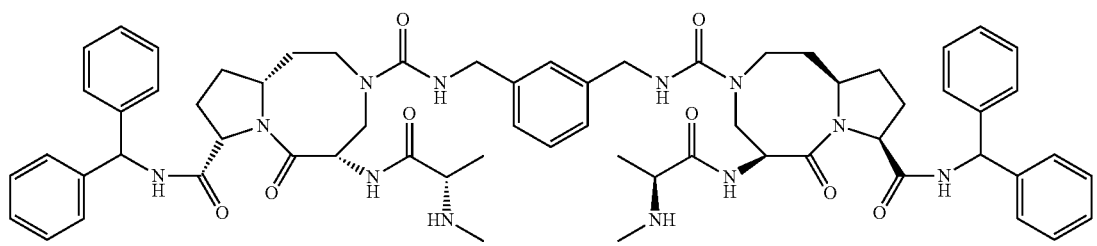
Example 3
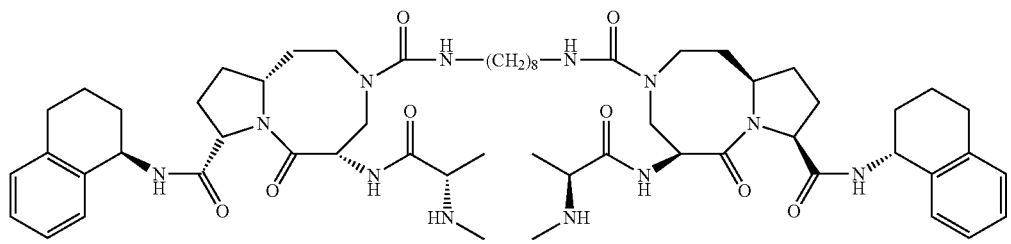
Example 4
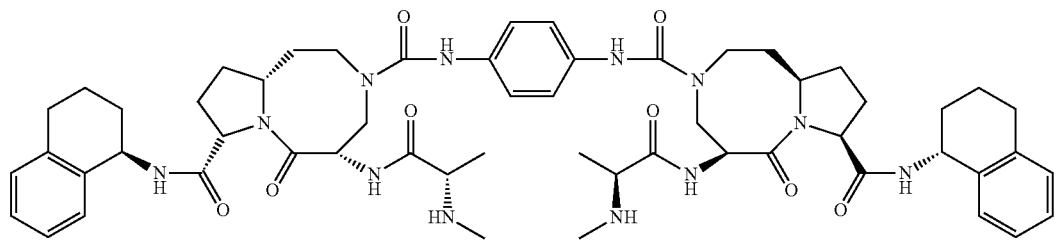
Example 5
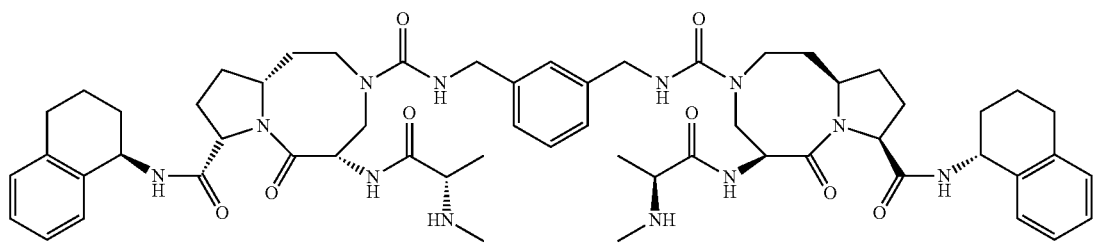
Example 6

-continued
Structures
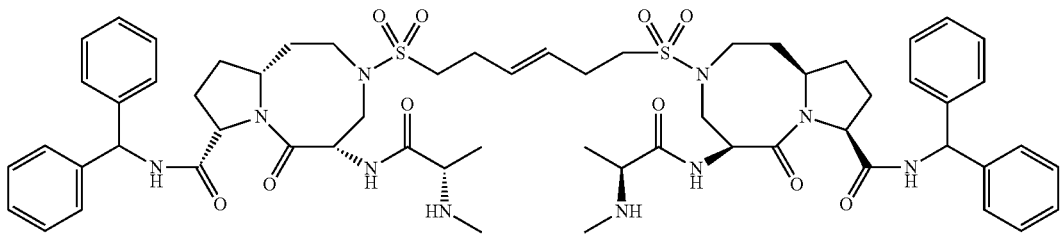
Example 7
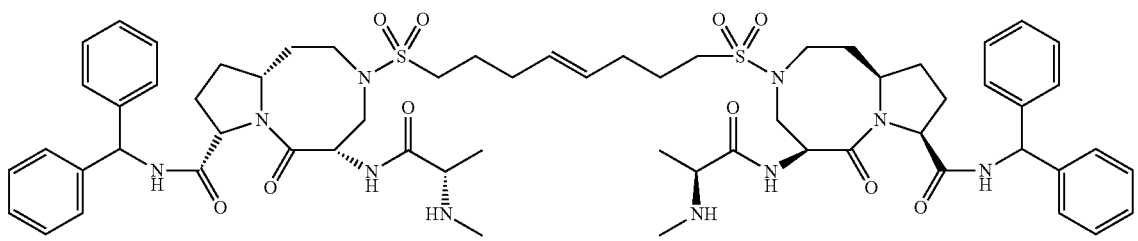
Example 8
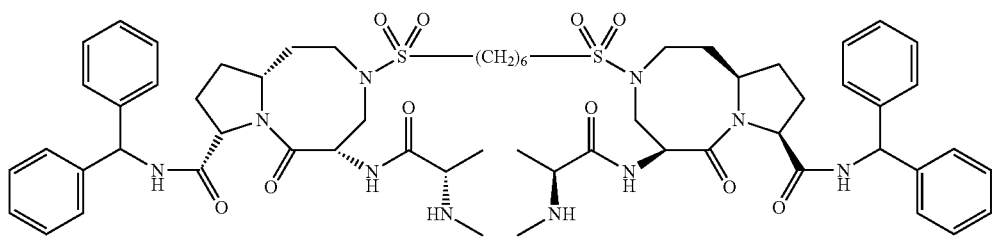
Example 9
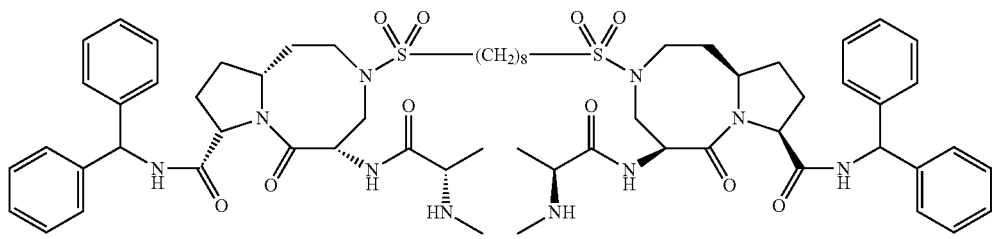
Example 10
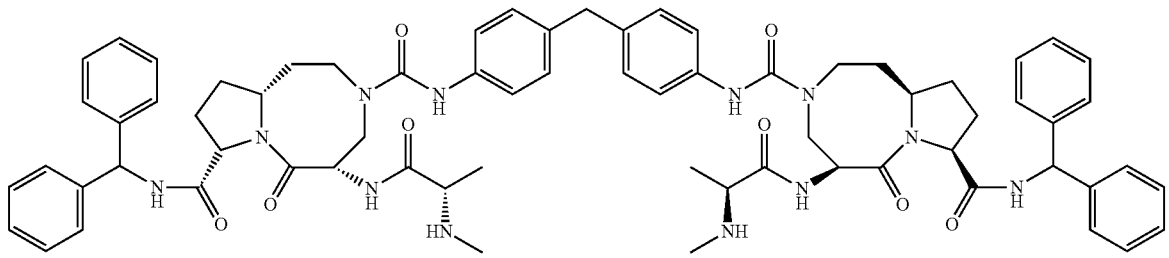
Example 11

-continued
Structures
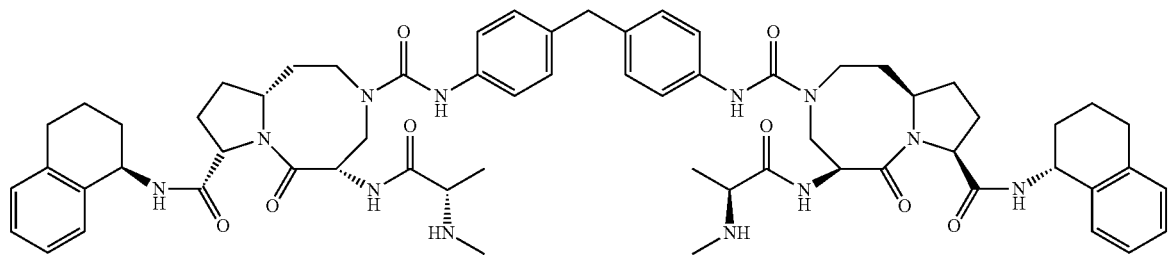
Example 12
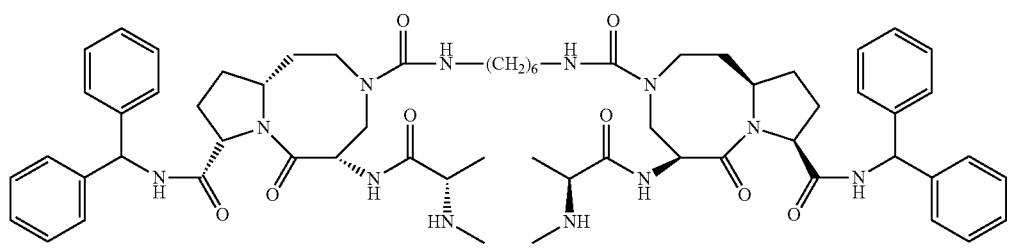
Example 13
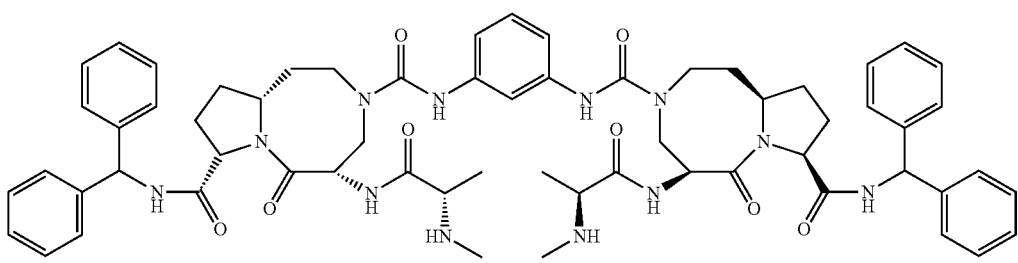
Example 14
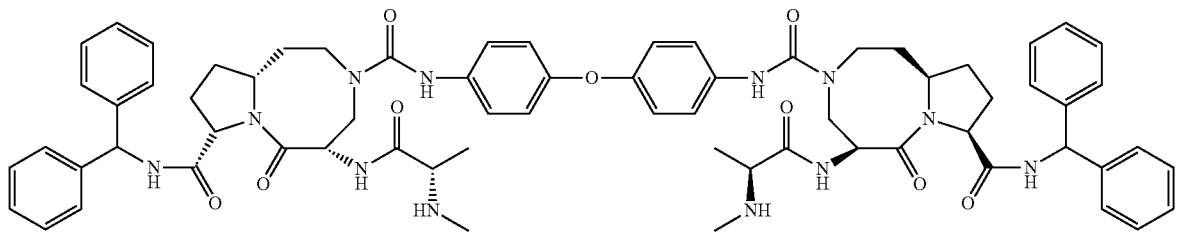
Example 15
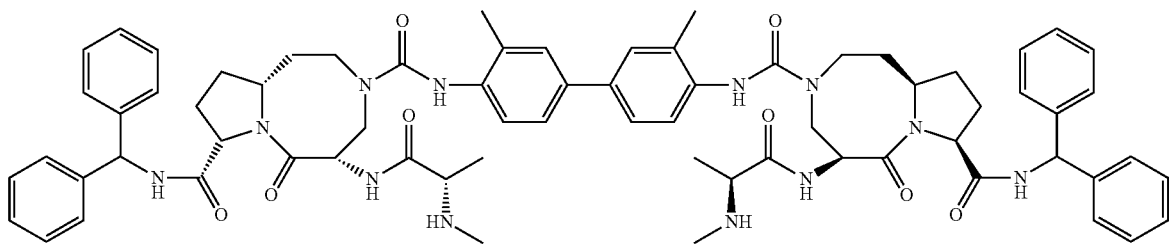
Example 16

-continued
Structures
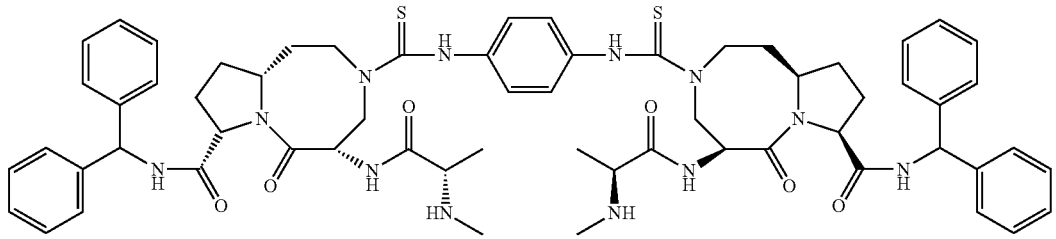
Example 17
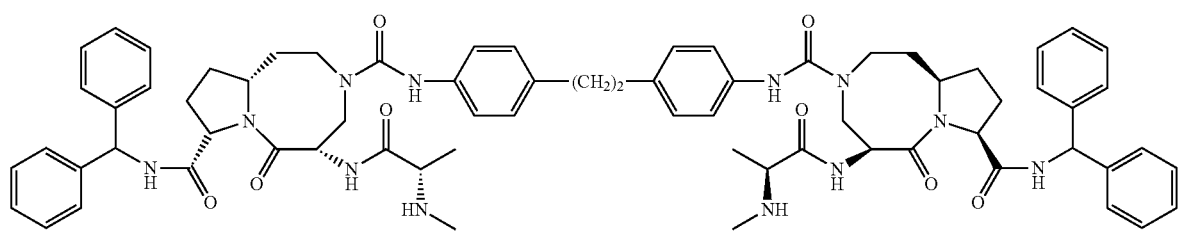
Example 18
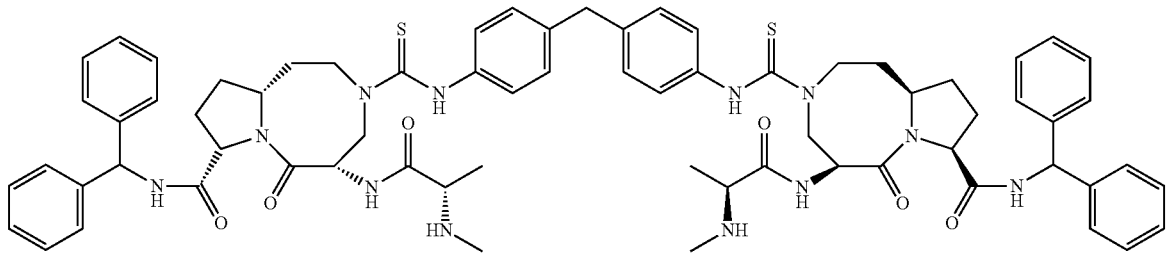
Example 19
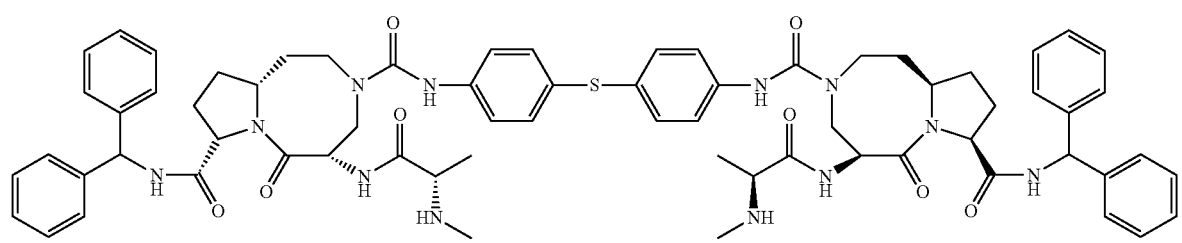
Example 20
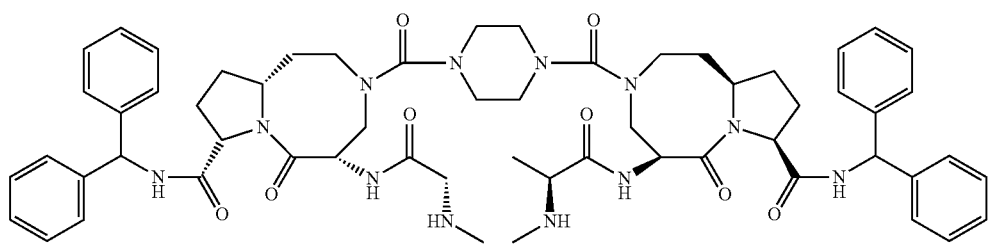
Example 21

-continued
Structures
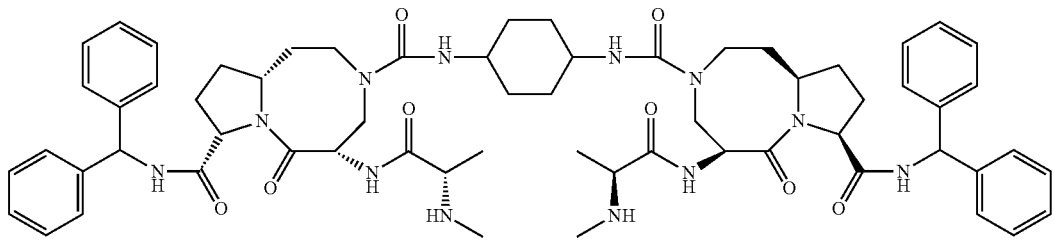
Example 22
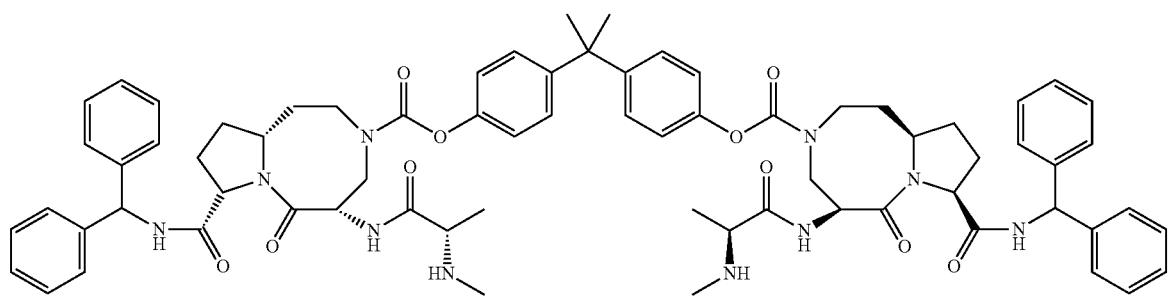
Example 23
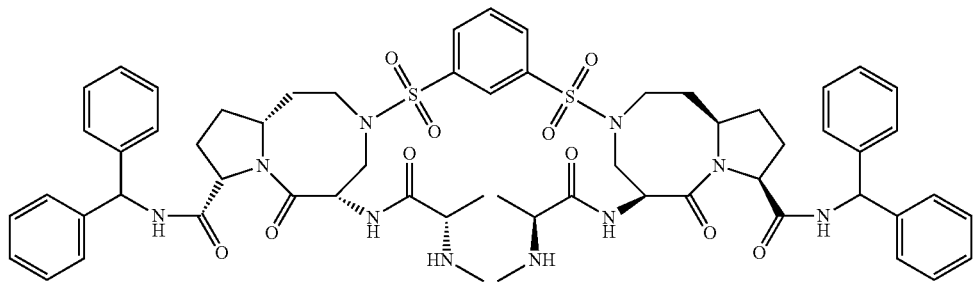
Example 24
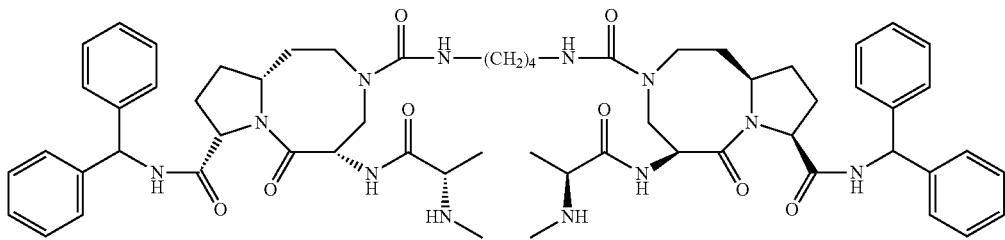
Example 25
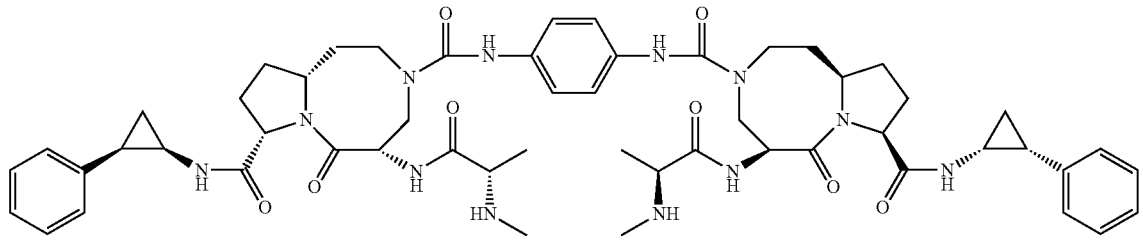
Example 26

-continued
Structures
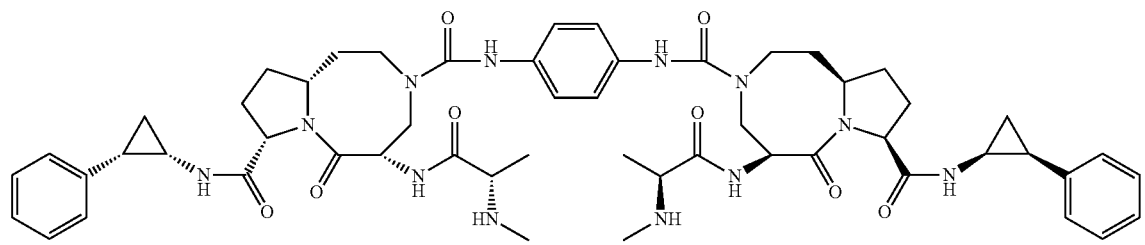
Example 27
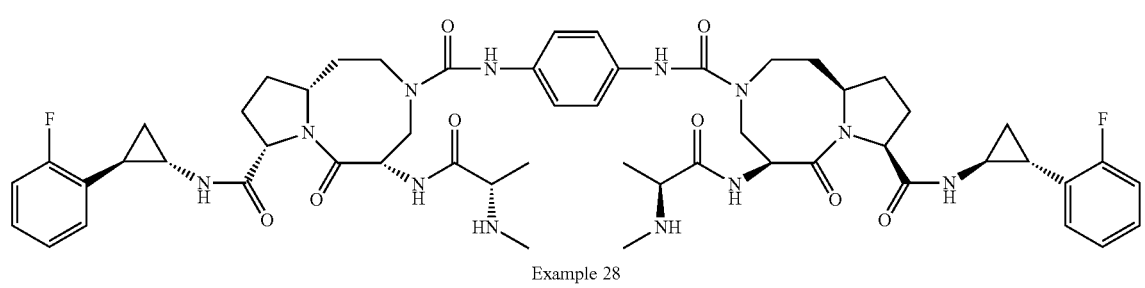 [SMILES: CN[C@@H](C)C(=O)N[C@H]1CN(C(=O)Nc2ccc(NC(=O)N3CC[C@H]4CC[C@@H](C(=O)N[C@H]5C[C@@H]5c5ccccc5F)N4C(=O)[C@@H](NC(=O)[C@H](C)NC)C3)cc2)CC[C@H]2CC[C@@H](C(=O)N[C@H]3C[C@@H]3c3ccccc3F)N2C1=O]
Example 28
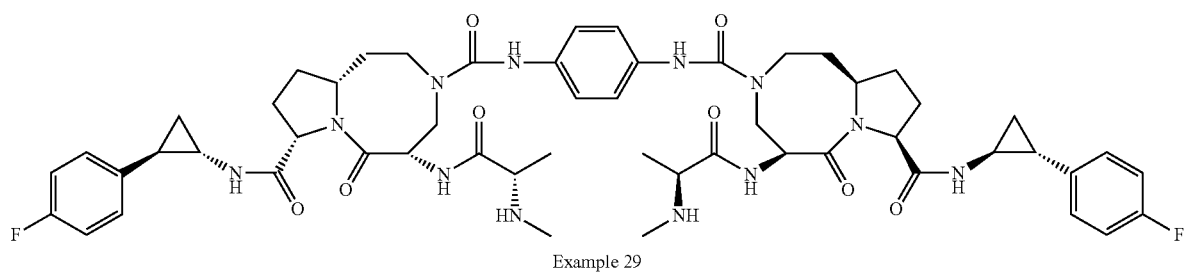 [SMILES: CN[C@@H](C)C(=O)N[C@H]1CN(C(=O)Nc2ccc(NC(=O)N3CC[C@H]4CC[C@@H](C(=O)N[C@H]5C[C@@H]5c5ccc(F)cc5)N4C(=O)[C@@H](NC(=O)[C@H](C)NC)C3)cc2)CC[C@H]2CC[C@@H](C(=O)N[C@H]3C[C@@H]3c3ccc(F)cc3)N2C1=O]
Example 29
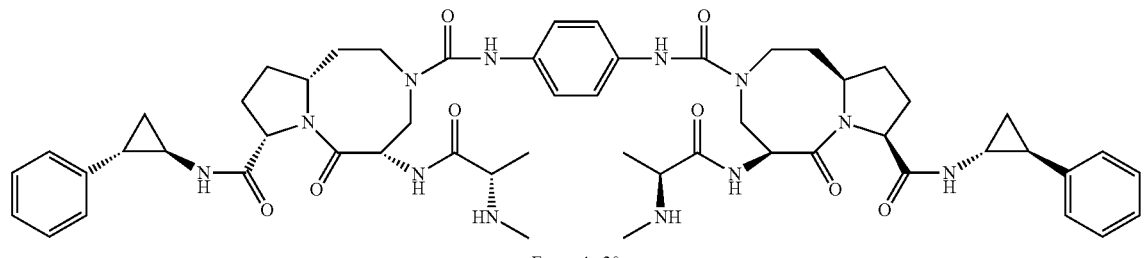
Example 30
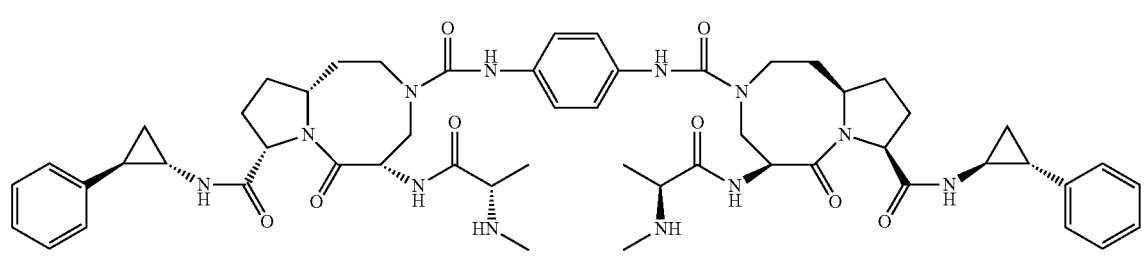
Example 31

-continued
Structures
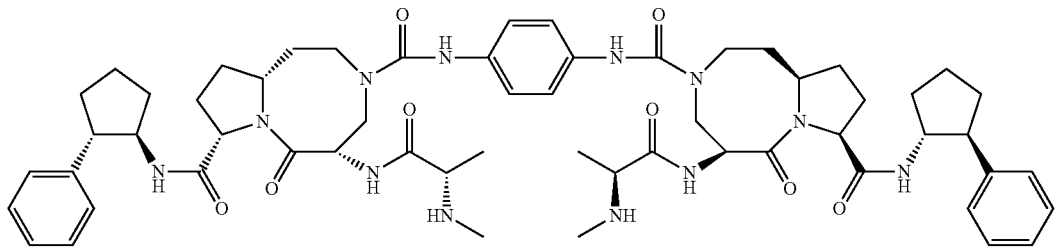
Example 32
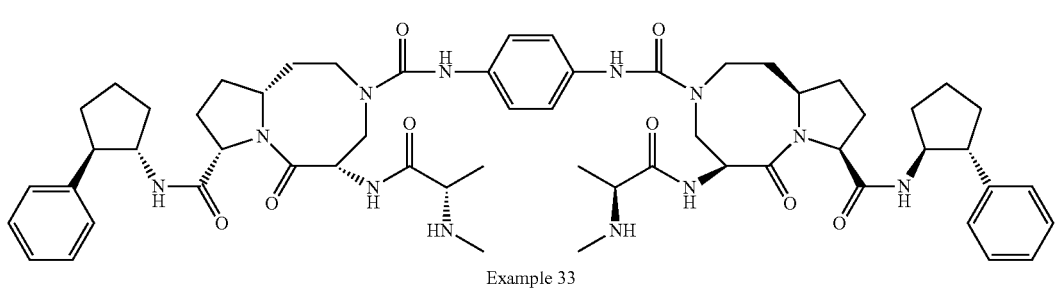 [SMILES: CN[C@@H](C)C(=O)N[C@H]1CN(C(=O)Nc2ccc(NC(=O)N3CC[C@H]4CC[C@@H](C(=O)N[C@H]5CCC[C@@H]5c5ccccc5)N4C(=O)[C@@H](NC(=O)[C@H](C)NC)C3)cc2)CC[C@H]2CC[C@@H](C(=O)N[C@H]3CCC[C@@H]3c3ccccc3)N2C1=O]
Example 33
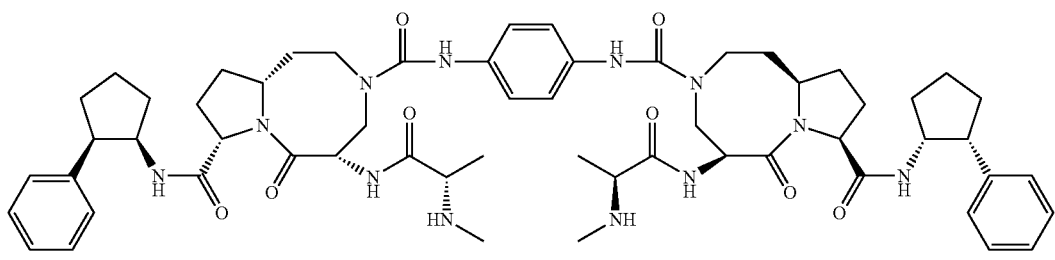
Example 34
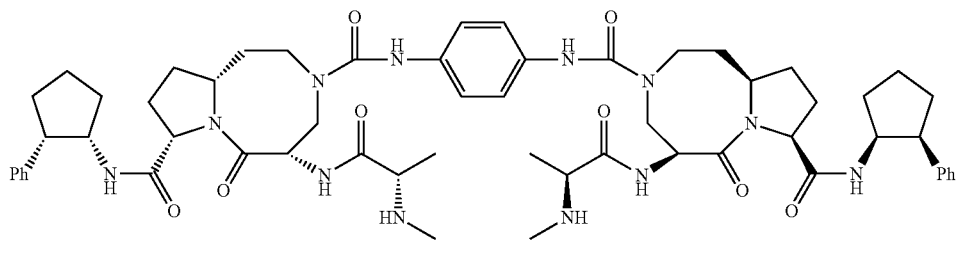
Example 35
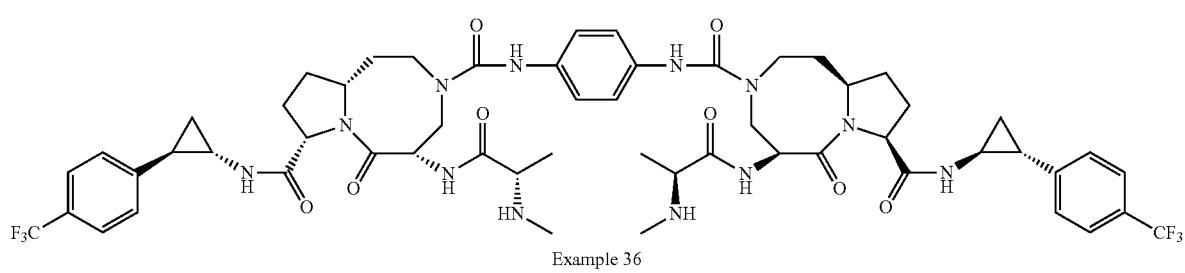 [SMILES: CN[C@@H](C)C(=O)N[C@H]1CN(C(=O)Nc2ccc(NC(=O)N3CC[C@H]4CC[C@@H](C(=O)N[C@H]5C[C@@H]5c5ccc(C(F)(F)F)c(F)c5)N4C(=O)[C@@H](NC(=O)[C@H](C)NC)C3)cc2)CC[C@H]2CC[C@@H](C(=O)N[C@H]3C[C@@H]3c3ccc(C(F)(F)F)c(F)c3)N2C1=O]
Example 36

-continued
Structures
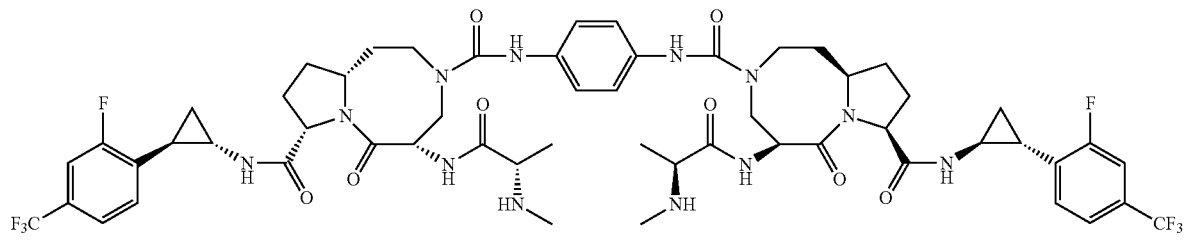
Example 37
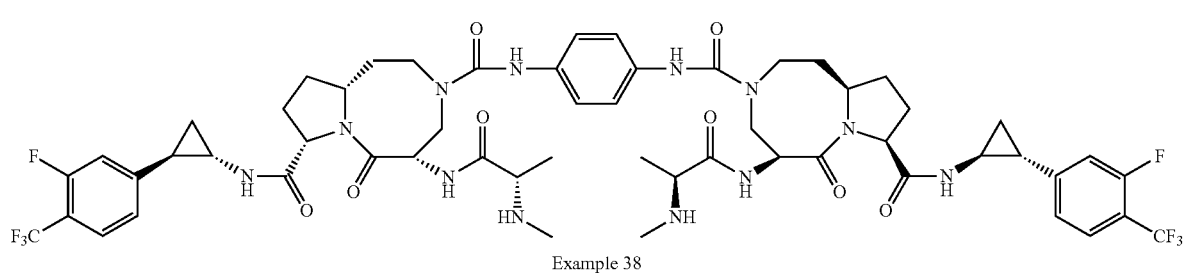
Example 38
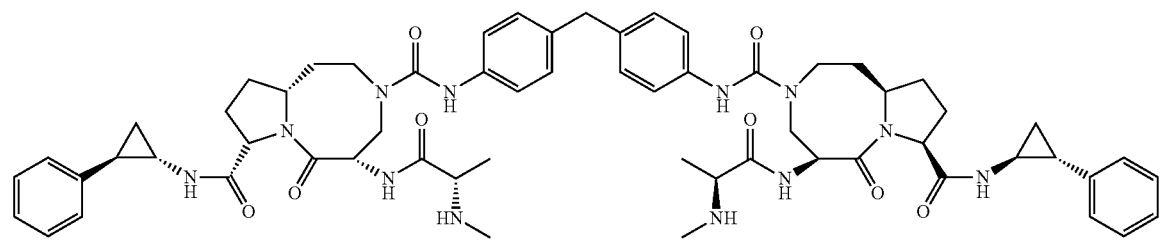
Example 39
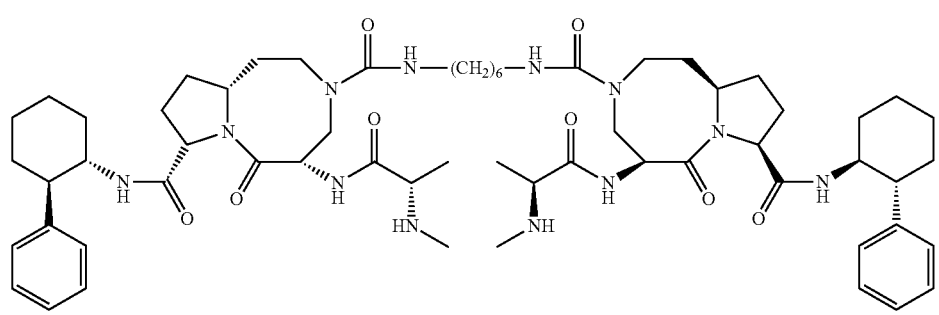
Example 40
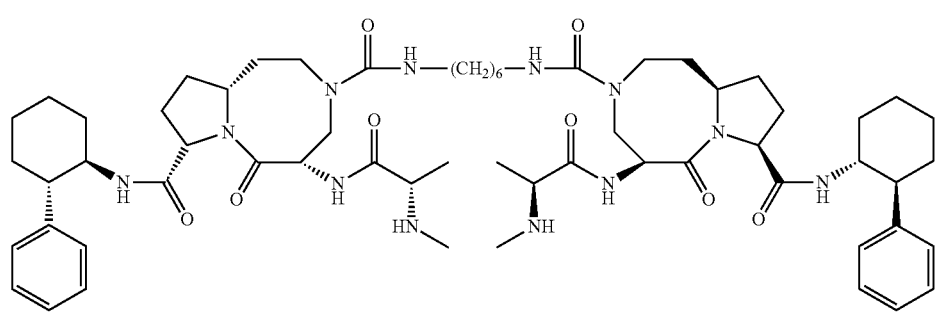
Example 41

-continued
Structures
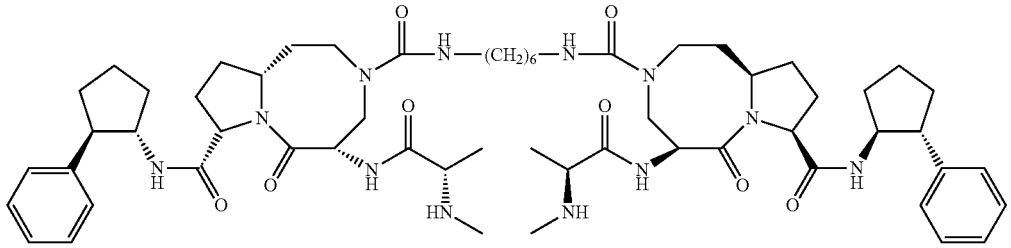
Example 42
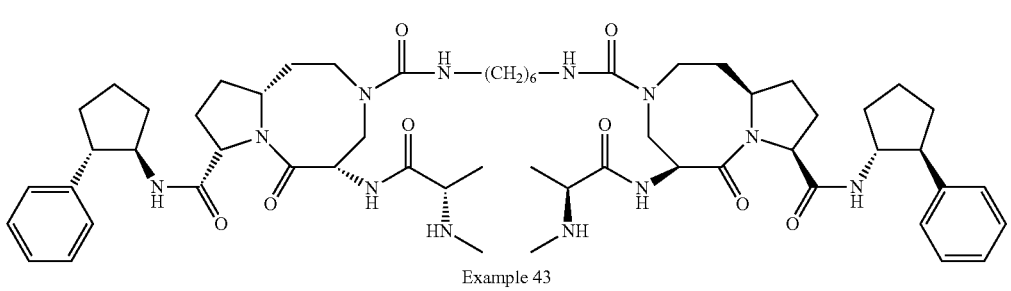
Example 43
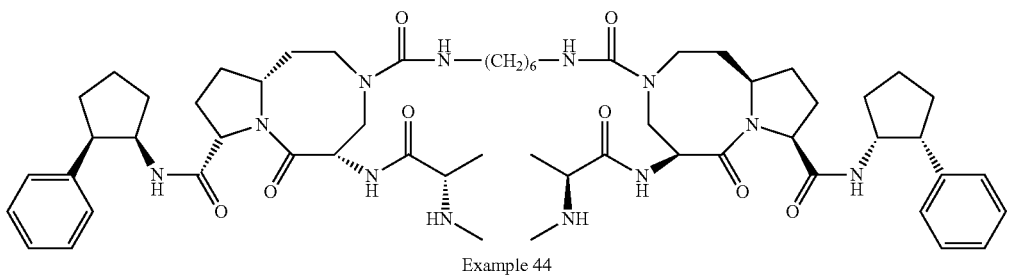
Example 44
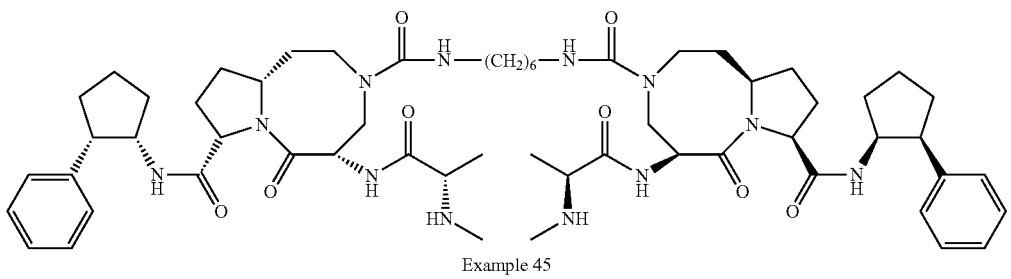
Example 45
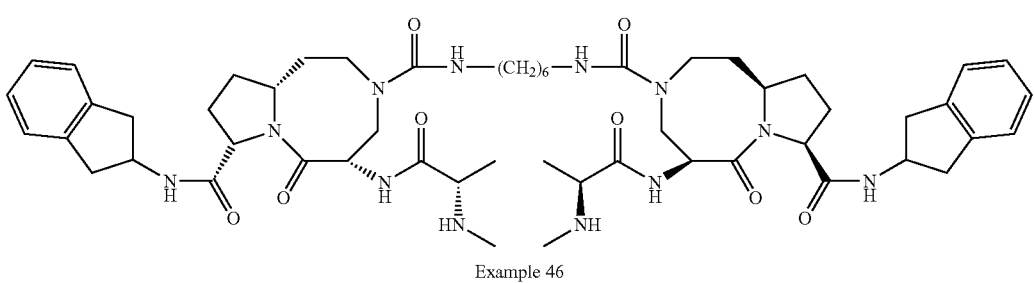
Example 46

| Structures |
|---|
| 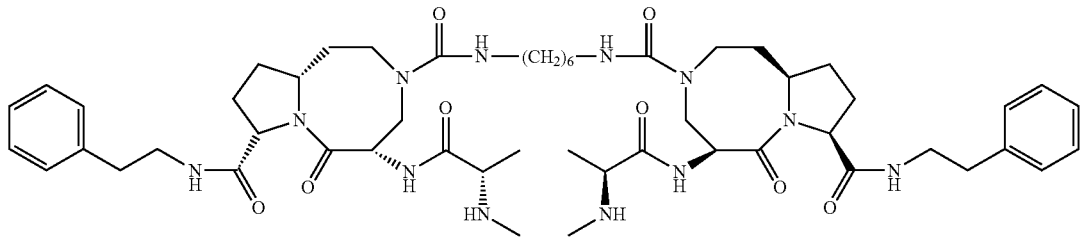<br>Example 47 |
| 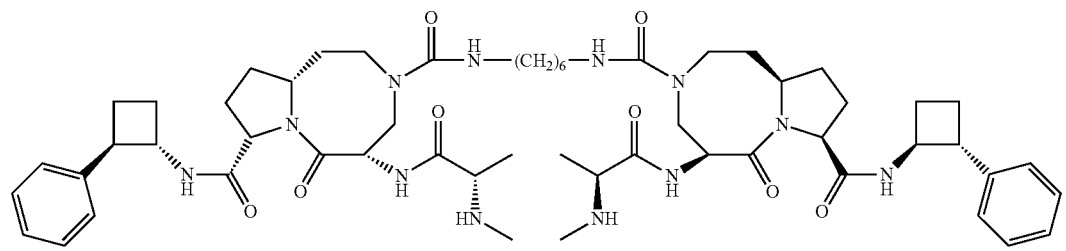<br>Example 48 |
| 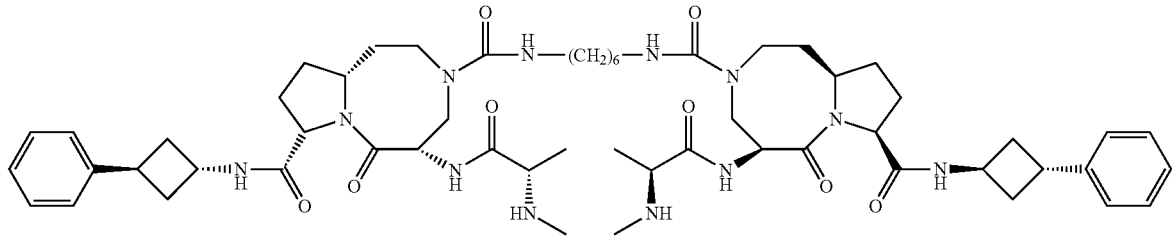<br>Example 49 |
| 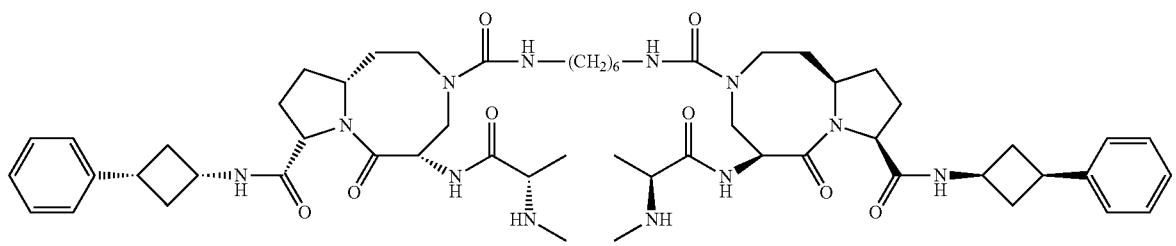<br>Example 50 |

The present invention provides IAP protein inhibitors, as exemplified by compounds of structural formula (I), for the treatment of a variety of diseases and conditions wherein inhibition of IAP proteins has a beneficial effect. In one embodiment, the present invention relates to a method of treating an individual suffering from a disease or condition wherein inhibition of IAP proteins provides a benefit comprising administering a therapeutically effective amount of a compound of structural formula (I) to an individual in need thereof.

The present IAP protein inhibitors satisfy a need for the treatment of multiple cancer types, either when administered as monotherapy to induce apoptosis in cancer cells dependent on IAP function, or when administered in a temporal relationship with other anticancer therapies so as to render a greater proportion of the cancer cells susceptible to executing the apoptosis program compared to the corresponding proportion of cells in an animal treated only with the cancer therapeutic drug or radiation therapy alone.

The term "anticancer therapy" as used herein, refers to therapeutic agents (e.g., chemotherapeutic compounds and/or molecular therapeutic compounds), radiation therapies, and surgical interventions used in the treatment of hyperproliferative diseases, such as a cancer in mammals.

The method of the present invention can be accomplished by administering a compound of structural formula (I) as the neat compound or as a pharmaceutical composition. Administration of a pharmaceutical composition, or neat compound of structural formula (I), can be performed during or after the onset of the disease or condition of interest. Typically, the pharmaceutical compositions are sterile, and contain no toxic, carcinogenic, or mutagenic compounds that would cause an adverse reaction when administered. Further provided are kits comprising a compound of structural formula (I) and, optionally, a second therapeutic agent useful in the treatment of diseases and conditions wherein inhibition of an IAP protein provides a benefit, packaged separately or together, and an insert having instructions for using these active agents.

In many embodiments, a compound of structural formula (I) is administered in conjunction with a second therapeutic agent useful in the treatment of a disease or condition wherein inhibition of an IAP protein provides a benefit. The second therapeutic agent is different from the compound of structural formula (I). A compound of structural formula (I) and the second therapeutic agent can be administered simultaneously or sequentially to achieve the desired effect. In addition, the compound of structural formula (I) and second therapeutic agent can be administered from a single composition or two separate compositions.

The second therapeutic agent is administered in an amount to provide its desired therapeutic effect. The effective dosage range for each second therapeutic agent is known in the art, and the second therapeutic agent is administered to an individual in need thereof within such established ranges.

In certain embodiments, a combination treatment comprising administering a therapeutically effective amount of a compound of structural formula (I) and a second therapeutic agent produces a greater tumor response and greater clinical benefit compared to treatment with a compound of structural formula (I) or second therapeutic agent alone.

The compounds of structural formula (I) also can be used to achieve administration of a lower, and therefore less toxic and more tolerable, dose of a second therapeutic agent to produce the same tumor response/clinical benefit as the conventional dose of a second therapeutic agent. Also, because the compounds of the present invention act at least in part by inhibiting IAP proteins, the exposure of cancer and supporting cells to therapeutically effective amounts of the present IAP protein inhibitors can be temporally linked to coincide with the attempts of cells to execute the apoptosis program in response to a second therapeutic agent. Thus, in some embodiments, administering compound of the present invention in connection with a second therapeutic agent in certain temporal relationships provides especially efficacious therapeutic results.

A compound of structural formula (I) and the second therapeutic agent therefore can be administered together as a single-unit dose or separately as multi-unit doses, wherein the compound of structural formula (I) is administered before the second therapeutic agent or vice versa. One or more dose of the compound of structural formula (I) and/or one or more dose of the second therapeutic agent can be administered. The compounds of structural formula (I) therefore can be used in conjunction with one or more second therapeutic agents, for example, but not limited to, anticancer agents.

The diseases and conditions that can be treated in accordance to the invention include, for example, cancers. A variety of cancers can be treated including, but not limited to: carcinomas, including bladder (including accelerated and metastic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, renal, and skin (including squamous cell carcinoma); hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma, hematopoietic tumors of myeloid lineage, including acute and chronic myelogenous leukemias, myelodysplastic syndrome, myeloid leukemia, and promyelocytic leukemia; tumors of the central and peripheral nervous system, including astrocytoma, neuroblastoma, glioma, and schwannomas; tumors of mesenchymal origin, including fibrosarcoma, rhabdomyoscarcoma, and osteosarcoma; and other tumors, including melanoma, xenoderma pigmentosum, keratoactanthoma, seminoma, thyroid follicular cancer, teratocarcinoma, renal cell carcinoma (RCC), pancreatic cancer, myeloma, myeloid and lymphoblastic leukemia, neuroblastoma, and glioblastoma.

Additional forms of cancer treatable by the IAP protein inhibitors of the present invention include, for example, adult and pediatric oncology, growth of solid tumors/malignancies, myxoid and round cell carcinoma, locally advanced tumors, metastatic cancer, human soft tissue sarcomas, including Ewing's sarcoma, cancer metastases, including lymphatic metastases, squamous cell carcinoma, particularly of the head and neck, esophageal squamous cell carcinoma, oral carcinoma, blood cell malignancies, including multiple myeloma, leukemias, including acute lymphocytic leukemia, acute nonlymphocytic leukemia, chronic lymphocytic leukemia, chronic myelocytic leukemia, and hairy cell leukemia, effusion lymphomas (body cavity based lymphomas), thymic lymphoma lung cancer (including small cell carcinoma, cutaneous T cell lymphoma, Hodgkin's lymphoma, non-Hodgkin's lymphoma, cancer of the adrenal cortex, ACTH-producing tumors, nonsmall cell cancers, breast cancer, including small cell carcinoma and ductal carcinoma), gastrointestinal cancers (including stomach cancer, colon cancer, colorectal cancer, and polyps associated with colorectal neoplasia), pancreatic cancer, liver cancer, urological cancers (including bladder cancer, such as primary superficial bladder tumors, invasive transitional cell carcinoma of the bladder, and muscle-invasive bladder cancer), prostate cancer, malignancies of the female genital tract (including ovarian carcinoma, primary peritoneal epithelial neoplasms, cervical carcinoma, uterine endometrial cancers, vaginal cancer, cancer of the vulva, uterine cancer and solid tumors in the ovarian follicle), malignancies of the male genital tract (including testicular cancer and penile cancer), kidney cancer (including renal cell carcinoma, brain cancer (including intrinsic brain tumors, neuroblastoma, astrocytic brain tumors, gliomas, and metastatic tumor cell invasion in the central nervous system), bone cancers (including osteomas and osteosarcomas), skin cancers (including malignant melanoma, tumor progression of human skin keratinocytes, and squamous cell cancer), thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma.

Another embodiment of the present invention is to induce apoptosis and potentiate the induction of apoptosis in response to apoptosis induction signals by use of an IAP protein inhibition of structural formula (I). The present IAP protein inhibitors also sensitize cells to inducers of apoptosis, including cells that are resistant to such inducers. The IAP protein inhibitors of the present invention can be used to induce apoptosis in any disorder that can be treated, ameliorated, or prevented by the induction of apoptosis. Thus, the present invention provides compositions and methods for targeting animals characterized as overexpressing an IAP protein. In some of the embodiments, the cells (e.g., cancer cells) show elevated expression levels of IAP proteins as compared to non-pathological samples (e.g., non-cancerous cells). In other embodiments, the cells operationally manifest elevated expression levels of IAP proteins by virtue of executing the apoptosis program and dying in response to a therapeutically effective amount of a compound of structural formula (I), said response occurring, at least in part, due to the dependence in such cells on IAP protein function for their survival.

In another embodiment, the invention pertains to modulating an apoptosis-associated state which is associated with one or more apoptosis-modulating agents. Examples of apoptosis-modulating agents include, but are not limited to, Fas/CD95, TRAMP, TNF RI, DR1, DR2, DR3, DR4, DR5, DR6, FADD, RIP, TNFα, Fas ligand, TRAIL, antibodies to TRAIL-R1 or TRAIL-R2, Bcl-2, p53, BAX, BAD, Akt, CAD, PI3 kinase, PP1, and caspase proteins. Other agents involved in the initiation, decision, and degradation phase of apoptosis are also included. Examples of apoptosis-modulating agents include agents, the activity, presence, or change in concentration of which, can modulate apoptosis in a subject. Preferred apoptosis-modulating agents are inducers of apoptosis, such as TNF or a TNF-related ligand, particularly a TRAMP ligand, a Fas/CD95 ligand, a TNFR-1 ligand, or TRAIL.

These therapies can be used in a variety of settings for the treatment of various cancers. In a specific embodiment, the individual in need of treatment has previously undergone treatment for cancer. Such previous treatments include, but are not limited to, prior chemotherapy, radiotherapy, surgery, or immunotherapy, such as cancer vaccines.

In one embodiment, the present invention provides a method of treating a cancer comprising: (a) administering to an individual in need thereof a therapeutically effective amount of an IAP protein inhibitor of structural formula (I); and (b) administering to the individual a therapeutically effective amount of one or more of radiotherapy, chemotherapy, and immunotherapy. The amounts administered are each effective to treat cancer. In another embodiment, the amounts are together effective to treat the cancer.

In another embodiment, the invention provides a method for treating a cancer, said method comprising administering to a subject in need thereof a pharmaceutical composition comprising an IAP protein inhibitor of structural formula (I).

In another embodiment, the present IAP protein inhibitors are used in methods of treating T and B cell mediated autoimmune diseases; inflammatory diseases; infections; hyperproliferative diseases; AIDS; degenerative conditions; vascular diseases; and the like. In some embodiments, infections suitable for treatment with the compositions and methods of the present invention include, but are not limited to, infections caused by viruses, bacteria, fungi, mycoplasma, prions, and the like.

The present compounds and methods also are useful in the treatment of autoimmune disorder or a chronic inflammatory condition. As used herein, the term "autoimmune disorder" refers to any condition in which an organism produces antibodies or immune cells which recognize the organism's own molecules, cells or tissues. Non-limiting examples of autoimmune disorders include autoimmune hemolytic anemia, autoimmune hepatitis, Berger's disease or IgA nephropathy, celiac sprue, chronic fatigue syndrome, Crohn's disease, dermatomyositis, fibromyalgia, graft versus host disease, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjögren's syndrome, systemic lupus erythematosus, type 1 diabetes, ulcerative colitis, vitiligo, and the like.

Additional diseases and conditions, including cancers, that can be treated by administration of a present IAP protein inhibitor are disclosed in U.S. Pat. No. 7,960,372; incorporated herein by reference in its entirety.

In the present method, a therapeutically effective amount of one or more compound (I), typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

A compound of structural formula (I) can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a compound of structural formula (I) is administered in an effective amount to achieve its intended purpose. The exact formulation, route of administration, and dosage is determined by an individual physician in view of the diagnosed condition or disease. Dosage amount and interval can be adjusted individually to provide levels of a compound of structural formula (I) that is sufficient to maintain therapeutic effects.

Toxicity and therapeutic efficacy of the compounds of structural formula (I) can be determined by standard pharmaceutical procedures in cell cultures or experimental animals, e.g., for determining the maximum tolerated dose (MTD) of a compound, which defines as the highest dose that causes no toxicity in animals. The dose ratio between the maximum tolerated dose and therapeutic effects (e.g. inhibiting of tumor growth) is the therapeutic index. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a compound of structural formula (I) required for use in therapy varies with the nature of the condition being treated, the length of time that activity is desired, and the age and the condition of the patient, and ultimately is determined by the attendant physician. Dosage amounts and intervals can be adjusted individually to provide plasma levels of the IAP protein inhibitor that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a present IAP protein inhibitor can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

A compound of structural formula (I) used in a method of the present invention can be administered in an amount of about 0.005 to about 500 milligrams per dose, about 0.05 to about 250 milligrams per dose, or about 0.5 to about 100 milligrams per dose. For example, a compound of structural formula (I) can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 500 milligrams.

The dosage of a composition containing an IAP protein inhibitor of structural formula (I), or a composition containing the same, can be from about 1 ng/kg to about 200 mg/kg, about 1 µg/kg to about 100 mg/kg, or about 1 mg/kg to about 50 mg/kg. The dosage of a composition can be at any dosage including, but not limited to, about 1 µg/kg. The dosage of a composition may be at any dosage including, but not limited to, about 1 µg/kg, 10 µg/kg, 25 µg/kg, 50 µg/kg, 75 µg/kg, 100 µg/kg, 125 µg/kg, 150 µg/kg, 175 µg/kg, 200 µg/kg, 225 µg/kg, 250 µg/kg, 275 µg/kg, 300 µg/kg, 325 µg/kg, 350 µg/kg, 375 µg/kg, 400 µg/kg, 425 µg/kg, 450 µg/kg, 475 µg/kg, 500 µg/kg, 525 µg/kg, 550 µg/kg, 575 µg/kg, 600 µg/kg, 625 µg/kg, 650 µg/kg, 675 µg/kg, 700 µg/kg, 725 µg/kg, 750 µg/kg, 775 µg/kg, 800 µg/kg, 825 µg/kg, 850 µg/kg, 875 µg/kg, 900 µg/kg, 925 µg/kg, 950 µg/kg, 975 µg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, or 200 mg/kg. The above dosages are exemplary of the average case, but there can be individual instances in which higher or lower dosages are merited, and such are within the scope of this invention. In practice, the physician determines the actual dosing regimen that is most suitable for an individual patient, which can vary with the age, weight, and response of the particular patient.

In the treatment of a cancer, a compound of structural formula (I) can be administered with a chemotherapeutic agent and/or an immunotherapeutic agent and/or radiation or in conjunction with another therapeutic technique, such as a surgery. As used herein, the term chemotherapeutic includes an anticancer agent, an anti-neoplastic agent, an apoptosis-modulating agent.

Embodiments of the present invention employ electromagnetic radiation of: gamma-radiation ($10^{-20}$ to $10^{-13}$ m), X-ray radiation ($10^{-12}$ to $10^{-9}$ m), ultraviolet light (10 nm to 400 nm), visible light (400 nm to 700 nm), infrared radiation (700 nm to 1 mm), and microwave radiation (1 mm to 30 cm).

Many cancer treatment protocols currently employ radiosensitizers activated by electromagnetic radiation, e.g., X-rays. Examples of X-ray-activated radiosensitizers include, but are not limited to, metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FUdR), hydroxyurea, cis-platin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, PHOTOFRIN®, benzoporphyrin derivatives, NPe6, tin etioporphyrin (SnET2), pheoborbide-a, bacteriochlorophyll-a, naphthalocyanines, phthalocyanines, zinc phthalocyanine, and therapeutically effective analogs and derivatives of the same.

Radiosensitizers can be administered in conjunction with a therapeutically effective amount of one or more compounds in addition to a present IAP protein inhibitor, such compounds including, but not limited to, compounds that promote the incorporation of radiosensitizers to the target cells, compounds that control the flow of therapeutics, nutrients, and/or oxygen to the target cells, chemotherapeutic agents that act on the tumor with or without additional radiation, or other therapeutically effective compounds for treating cancer or other disease. Examples of additional therapeutic agents that can be used in conjunction with radiosensitizers include, but are not limited to, 5-fluorouracil (5-FU), leucovorin, oxygen, carbogen, red cell transfusions, perfluorocarbons (e.g., FLUO-SOLW®-DA), 2,3-DPG, BW12C, calcium channel blockers, pentoxifylline, antiangiogenesis compounds, hydralazine, and L-BSO.

The chemotherapeutic agent can be any pharmacological agent or compound that induces apoptosis. The pharmacological agent or compound can be, for example, a small organic molecule, peptide, polypeptide, nucleic acid, or antibody. Chemotherapeutic agents that can be used include, but are not limited to, alkylating agents, antimetabolites, hormones and antagonists thereof, natural products and their derivatives, radioisotopes, antibodies, as well as natural products, and combinations thereof. For example, an IAP protein inhibitor of the present invention can be administered with antibiotics, such as doxorubicin and other anthracycline analogs, nitrogen mustards, such as cyclophosphamide, pyrimidine analogs such as 5-fluorouracil, cis-platin, hydroxyurea, taxol and its natural and synthetic derivatives, and the like. As another example, in the case of mixed tumors, such as adenocarcinoma of the breast, where the tumors include gonadotropin-dependent and gonadotropin-independent cells, the compound can be administered in conjunction with leuprolide or goserelin (synthetic peptide analogs of LH-RH). Other antineoplastic protocols include the use of an inhibitor compound with another treatment modality, e.g., surgery or radiation, also referred to herein as "adjunct anti-neoplastic modalities." Additional chemotherapeutic agents useful in the invention include hormones and antagonists thereof, radioisotopes, antibodies, natural products, and combinations thereof.

Examples of chemotherapeutic agents useful in a method of the present invention are listed in the following table.

TABLE 1

Alkylating agents
Nitrogen mustards mechlorethamine
cyclophosphamide
ifosfamide
melphalan
chlorambucil
uracil mustard
temozolomide
Nitrosoureas carmustine (BCNU)
lomustine (CCNU)
semustine (methyl-CCNU)
chlormethine
streptozocin
Ethylenimine/Methyl-melamine triethylenemelamine (TEM)
triethylene thiophosphoramide
(thiotepa)
hexamethylmelamine
(HMM, altretamine)
Alkyl sulfonates busulfan
pipobroman TABLE 1-continued Triazines dacarbazine (DTIC)
Antimetabolites
Folic Acid analogs methotrexate
trimetrexate
pemetrexed
(Multi-targeted antifolate)
Pyrimidine analogs 5-fluorouracil
fluorodeoxyuridine
gemcitabine
cytosine arabinoside
(AraC, cytarabine)
5-azacytidine
2,2'-difluorodeoxy-cytidine
floxuridine
pentostatine
Purine analogs
6-mercaptopurine
6-thioguanine
azathioprine
2'-deoxycoformycin
(pentostatin)
erythrohydroxynonyl-adenine (EHNA)
fludarabine phosphate
2-chlorodeoxyadenosine
(cladribine, 2-CdA)
Type I Topoisomerase Inhibitors camptothecin
topotecan
irinotecan
Biological response modifiers G-CSF
GM-CSF
Differentiation Agents retinoic acid derivatives
Hormones and antagonists
Adrenocorticosteroids/antagonists prednisone and equivalents
dexamethasone
ainoglutethimide
Progestins hydroxyprogesterone caproate
medroxyprogesterone acetate
megestrol acetate
Estrogens diethylstilbestrol
ethynyl estradiol/equivalents
Antiestrogen tamoxifen
Androgens testosterone propionate
fluoxymesterone/equivalents
Antiandrogens flutamide
gonadotropin-releasing
hormone analogs
leuprolide
Natural products
Antimitotic drugs
Taxanes paclitaxel
Vinca alkaloids
vinblastine (VLB)
vincristine
vinorelbine TABLE 1-continued vindesine
Taxotere ® (docetaxel)
estramustine
estramustine phosphate
Epipodophylotoxins etoposide
teniposide
Antibiotics actimomycin D
daunomycin (rubidomycin)
doxorubicin (adriamycin)
mitoxantroneidarubicin
bleomycin
splicamycin (mithramycin)
mitromycin-C
dactinomycin
aphidicolin
epirubicin
idarubicin
daunorubicin
mithramycin
deoxy co-formycin
Enzymes L-asparaginase
L-arginase
Radiosensitizers metronidazole
misonidazole
desmethylmisonidazole
pimonidazole
etanidazole
nimorazole
RSU 1069
EO9
RB 6145
Nonsteroidal antiandrogens SR4233
flutamide
nicotinamide
5-bromodeozyuridine
5-iododeoxyuridine
bromodeoxycytidine
Miscellaneous agents
Platinum coordination complexes cisplatin
carboplatin
oxaliplatin
anthracenedione
mitoxantrone
Substituted urea hydroxyurea
Methylhydrazine derivatives N-methylhydrazine (MIH)
procarbazine
Adrenocortical suppressant mitotane (o,p'-DDD)
ainoglutethimide
Cytokines interferon ($\alpha$, $\beta$, $\gamma$)
interleukin-2
Photosensitizers hematoporphyrin derivatives
PHOTOFRIN ®
benzoporphyrin derivatives
Npe6
tin etioporphyrin (SnET2)
pheoboride-a
bacteriochlorophyll-a
naphthalocyanines

TABLE 1-continued phthalocyanines
zinc phthalocyanines
Radiation

X-ray
ultraviolet light
gamma radiation
visible light
infrared radiation
microwave radiation Microtubule affecting agents interfere with cellular mitosis and are well known in the art for their cytotoxic activity. Microtubule affecting agents useful in the invention include, but are not limited to, allocolchicine (NSC 406042), halichondrin B (NSC 609395), colchicines (NSC 757), colchicines derivatives (e.g., NSC 33410), dolastatin 10 (NSC 376128), maytansine (NSC 153858), rhizoxin (NSC 332598), paclitaxel (NSC 125973), TAXOL® derivatives (e.g., NSC 608832), thiocolchicine NSC 361792), trityl cysteine (NSC 83265), vinblastine sulfate (NSC 49842), vincristine sulfate (NSC 67574), natural and synthetic epothilones including but not limited to epothilone A, eopthilone B, and discodermolide (see Service, (1996) Science, 274:2009) estramustine, nocodazole, MAP4, and the like. Examples of such agents are also described in Bulinski (1997) *J. Cell Sci.* 110:3055 3064; Panda (1997) *Proc. Natl. Acad. Sci. USA* 94:10560-10564; Muhlradt (1997) *Cancer Res.* 57:3344-3346; Nicolaou (1997) *Nature* 397:268-272; Vasquez (1997) *Mol. Biol. Cell.* 8:973-985; and Panda (1996) *J. Biol. Chem.* 271:29807-29812.

Cytostatic agents that may be used include, but are not limited to, hormones and steroids (including synthetic analogs): 17-α-ethinylestadiol, diethylstilbestrol, testosterone, prednisone, fluoxymesterone, dromostanolone propionate, testolactone, megestrolacetate, methylprednisolone, methyltestosterone, prednisolone, triamcinolone, hlorotrianisene, hydroxyprogesterone, aminogluthimide, estramustine, medroxyprogesteroneacetate, leuprolide, flutamide, toremifene, zoladex.

Other cytostatic agents are antiangiogenics, such as matrix metalloproteinase inhibitors, and other VEGF inhibitors, such as anti-VEGF antibodies and small molecules such as ZD6474 and SU668. Anti-Her2 antibodies also may be utilized. An EGFR inhibitor is EKB-569 (an irreversible inhibitor). Also included are antibody C225 immunospecific for the EGFR and Src inhibitors.

Also suitable for use as a cytostatic agent is CASODEX® (bicalutamide, Astra Zeneca) which renders androgen-dependent carcinomas non-proliferative. Yet another example of a cytostatic agent is the antiestrogen TAMOXIFEN® which inhibits the proliferation or growth of estrogen dependent breast cancer. Inhibitors of the transduction of cellular proliferative signals are cytostatic agents. Representative examples include epidermal growth factor inhibitors, Her-2 inhibitors, MEK-1 kinase inhibitors, MAPK kinase inhibitors, PI3 inhibitors, Src kinase inhibitors, and PDGF inhibitors.

Antimicrobial therapeutic agents may also be used as second therapeutic agents in the present invention. Any agent that can kill, inhibit, or otherwise attenuate the function of microbial organisms may be used, as well as any agent contemplated to have such activities. Antimicrobial agents include, but are not limited to, natural and synthetic antibiotics, antibodies, inhibitory proteins (e.g., defensins), antisense nucleic acids, membrane disruptive agents and the like, used alone or in combination. Indeed, any type of antibiotic may be used including, but not limited to, antibacterial agents, antiviral agents, antifungal agents, and the like.

Additional second therapeutic agents that can be administered with an IAP protein inhibitor of the present invention are disclosed in U.S. Pat. No. 7,960,372, incorporated herein by reference in its entirety.

The compounds of the present invention typically are administered in admixture with a pharmaceutical carrier selected with regard to the intended route of administration and standard pharmaceutical practice. Pharmaceutical compositions for use in accordance with the present invention are formulated in a conventional manner using one or more physiologically acceptable carriers comprising excipients and auxiliaries that facilitate processing of compounds of structural formula (I).

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of the compound of structural formula (I) is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a compound of structural formula (I). When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a compound of structural formula (I).

When a therapeutically effective amount of a compound of structural formula (I) is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle.

Compounds of structural formula (I) can be readily combined with pharmaceutically acceptable carriers well-known in the art. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding the compound of structural formula (I) to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

A compound of structural formula (I) can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a compound of structural formula (I) can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

A compound of structural formula (I) also can be formulated in rectal compositions, such as suppositories or retention enemas, e.g., containing conventional suppository bases. In addition to the formulations described previously, the compound of structural formula (I) also can be formulated as a depot preparation. Such long-acting formulations can be administered by implantation (for example, subcutaneously or intramuscularly) or by intramuscular injection. Thus, for example, the compounds of structural formula (I) can be formulated with suitable polymeric or hydrophobic materials (for example, as an emulsion in an acceptable oil) or ion exchange resins.

In particular, the compounds of structural formula (I) can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. The compounds of structural formula (I) also can be injected parenterally, for example, intravenously, intramuscularly, subcutaneously, or intracoronarily. For parenteral administration, the IAP protein inhibitors are best used in the form of a sterile aqueous solution which can contain other substances, for example, salts or monosaccharides, such as mannitol or glucose, to make the solution isotonic with blood.

As an additional embodiment, the present invention includes kits which comprise one or more compounds or compositions packaged in a manner that facilitates their use to practice methods of the invention. In one simple embodiment, the kit includes a compound or composition described herein as useful for practice of a method (e.g., a composition comprising a compound of structural formula (I) and an optional second therapeutic agent), packaged in a container, such as a sealed bottle or vessel, with a label affixed to the container or included in the kit that describes use of the compound or composition to practice the method of the invention. Preferably, the compound or composition is packaged in a unit dosage form. The kit further can include a device suitable for administering the composition according to the intended route of administration.

Prior IAP protein inhibitors possessed properties that hindered their development as therapeutic agents. In accordance with an important feature of the present invention, compounds of structural formula (I) were synthesized and evaluated as inhibitors of IAP proteins. For example, compounds of the present invention typically have a bonding affinity ($IC_{50}$) to IAP proteins of less than 100 nM, less than 50 nM, less than 25 nM, and less than 10 nM.

Synthesis of Compounds

Compounds of the present invention and were prepared as follows. The following synthetic schemes are representative of the reactions used to synthesize compounds of structural formula (I). Modifications and alternate schemes to prepare IAP protein inhibitors of the invention are readily within the capabilities of persons skilled in the art.

Solvents and reagents were obtained commercially and used without further purification. Chemical shifts (δ) of NMR spectra are reported as δ values (ppm) downfield relative to an internal standard, with multiplicities reported in the usual manner.

Unless otherwise stated all temperatures are in degrees Celsius.

In the synthetic methods, the examples, and throughout the specification, the abbreviations have the following meanings:

| | |
|---|---|
| MS | mass spectrometry |
| CbzCl | benzyl chloroformate |
| LiOH | lithium hydroxide |
| HCl | hydrochloric acid |
| $CD_3OD$ | deuterated methanol |
| NMR | nuclear magnetic resonance spectrometry |
| Hz | Hertz |
| EDC | 1-ethyl-3-(3-dimethylaminopropyl)carbodiimide hydrochloride |
| HOBt | 1-hydroxybenzotriazole |
| Pd/C | palladium on carbon |

Synthetic Scheme 1

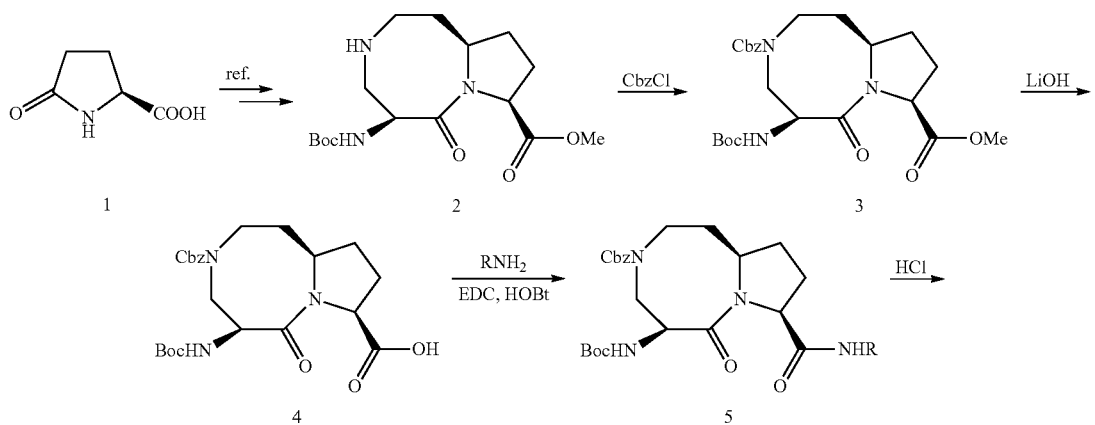

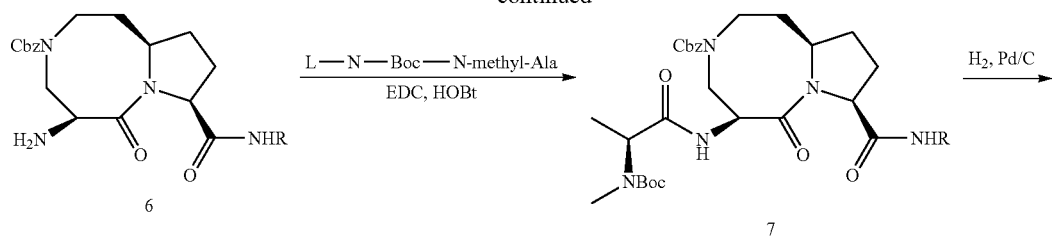
-continued
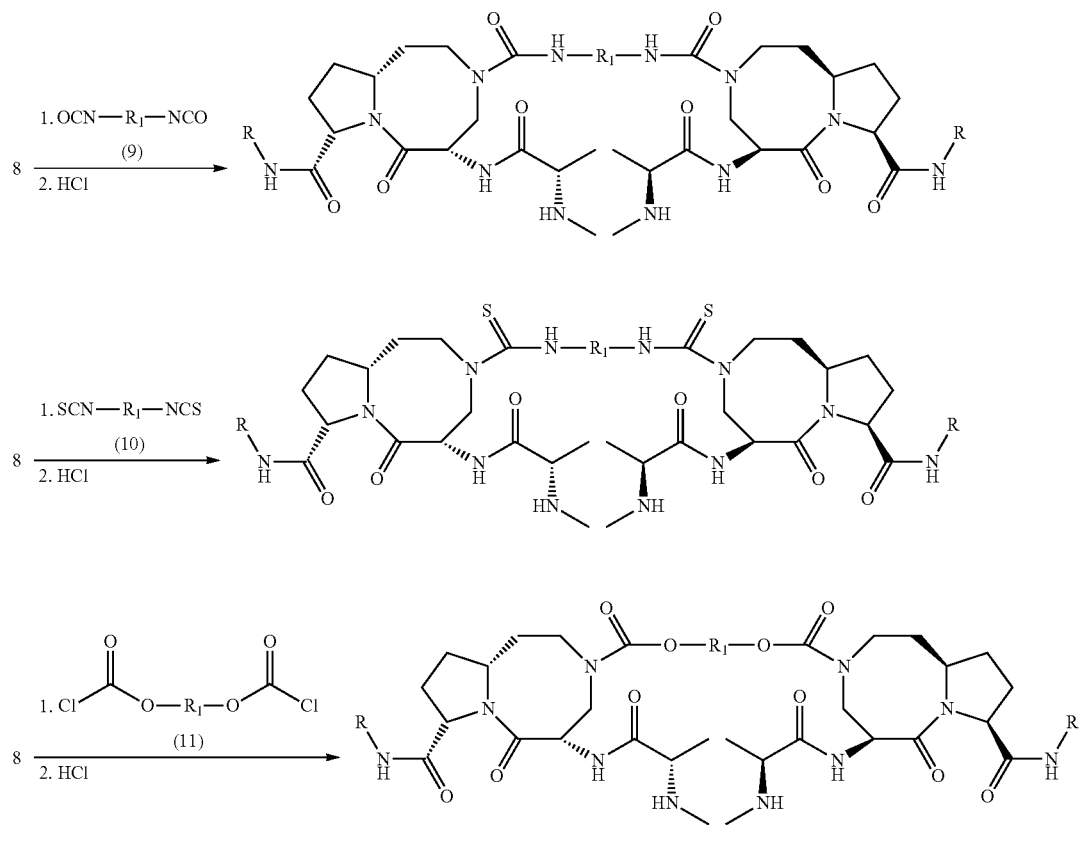
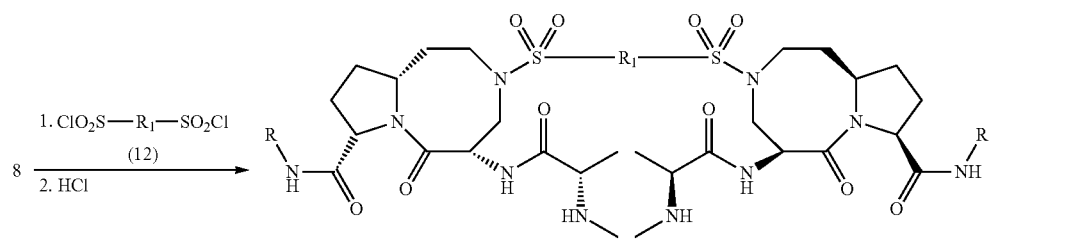

Each compound of structural formula (I), except those having a cyclopropyl ring in R, are synthesized according to the method shown in the above Synthetic Scheme 1. Compound 2 was synthesized according to the method disclosed in Q. Cai et al., *J. Med. Chem.*, 2011, 2714-26. Protection of the amino group in compound 2 with Cbz gave a carbamate 3. Hydrolysis of the methyl ester in carbamate 3 yielded acid 4. Condensation of acid 4 with a series of amines respectively afforded amides 5. Removal of the Boc protecting group in amide 5 yielded amine 6. Condensation of amine 6 with L-N-Boc-N-methyl-alanine provided amides 7. Cleavage of the Cbz protecting group in amide 7 afforded amines 8.

Condensation of amine 8 with a series of diisocyanates (9), and the subsequent removal of the Boc protecting groups yielded bis-urea containing Smac mimetics. Condensation of amine 8 with a series of diisothiocyanates (10) and the subsequent removal of the Boc protecting groups yielded bis-thiourea containing Smac mimetics. Condensation of amine 8 with a series of dicarbonochloridate (12) and the subsequent removal of the Boc protecting groups yielded bis-carbamate contained Smac mimetics. Condensation of amine 8 with a series of disulfonyl chlorides and the subsequent removal of the Boc protecting groups yielded bis-sulfonamides containing Smac mimetics.

Synthetic Scheme 2

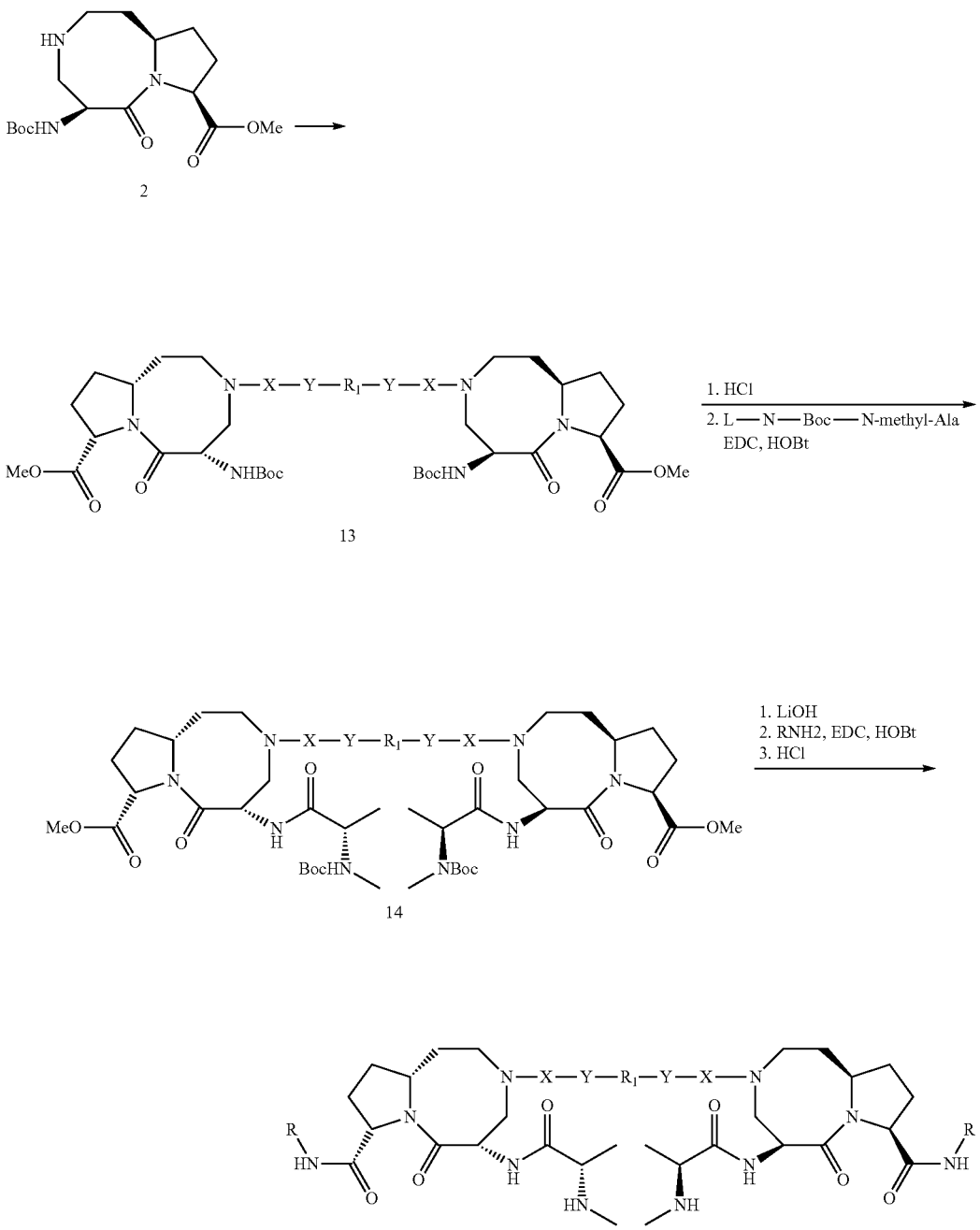

Compounds of general structural formula (I) having a cyclopropyl ring in R, the synthesis is shown in above Synthetic Scheme 2. Condensation of compound 2 with diisocyanates, diisothiocyanates, dicarbonochloridate, or disulfonyl chlorides respectively gave intermediates 13. Removal of the Boc protecting groups in compound 13, and the subsequent condensation with L-N-Boc-N-methyl-Ala yielded amides 14. Hydrolysis of the methyl esters in amide 14 furnished a series of acids. Condensation of the acids with a series of amine and the subsequent deprotection of the Boc protecting groups provided final compounds.

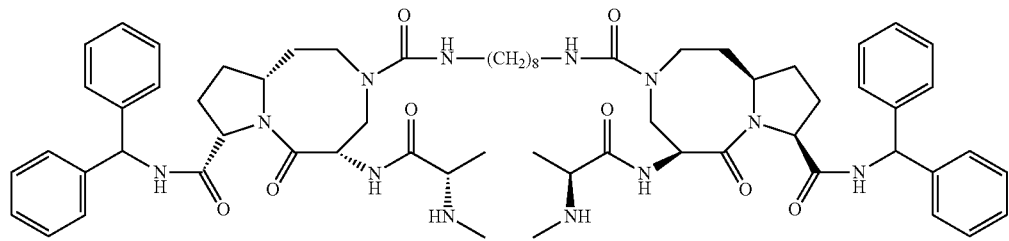

Example 1

$^1$H NMR (300 MHz, CD$_3$OD): δ 7.37-7.24 (m, 20H), 6.16 (s, 2H), 4.72-4.60 (m, 4H), 4.10 (m, 2H), 4.00-3.85 (m, 6H), 3.25-3.04 (m, 8H), 2.69 (s, 6H), 2.34 (m, 2H), 2.14-2.03 (m, 6H), 1.77-1.48 (m, 8H), 1.54 (d, J=6.9 Hz, 6H), 1.35 (m, 8H); ESI MS: m/z 1151.8 (M+H)$^+$.

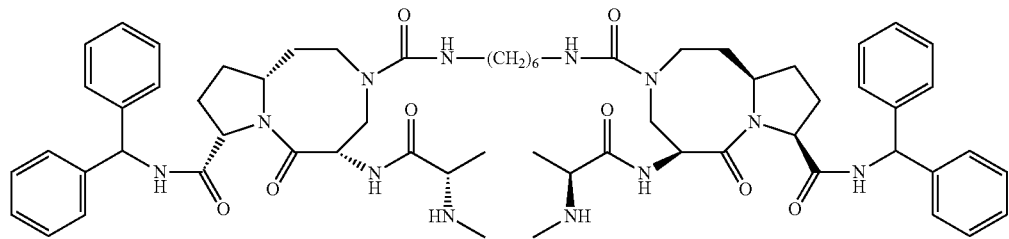

Example 13

$^1$H NMR (300 MHz, CD$_3$OD): δ 7.35-7.23 (m, 20H), 6.15 (s, 2H), 4.70-4.60 (m, 4H), 4.10 (m, 2H), 3.97-3.80 (m, 6H), 3.25-3.03 (m, 8H), 2.69 (s, 6H), 2.34 (m, 2H), 2.10-2.03 (m, 6H), 1.78-1.57 (m, 8H), 1.52 (d, J=7.2 Hz, 6H), 1.39 (m, 4H); ESI MS: m/z 1123.6 (M+H)$^+$.

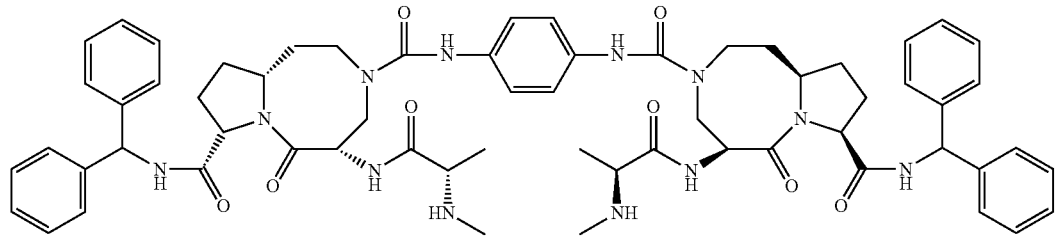

Example 2

$^1$H NMR (300 MHz, CD$_3$OD): δ 7.53 (s, 4H), 7.37 (m, 20H), 6.18 (s, 2H), 4.84 (m, 2H), 4.67 (t, J=8.4 Hz, 2H), 4.27 (m, 2H), 4.09-3.80 (m, 6H), 3.30-3.05 (m, 4H), 2.71 (s, 6H), 2.37 (m, 2H), 2.35-1.80 (m, 4H), 1.70-1.55 (m, 6H), 1.45 (d, J=6.9 Hz, 6H); ESI MS: m/z 1115.9 (M+H)$^+$.

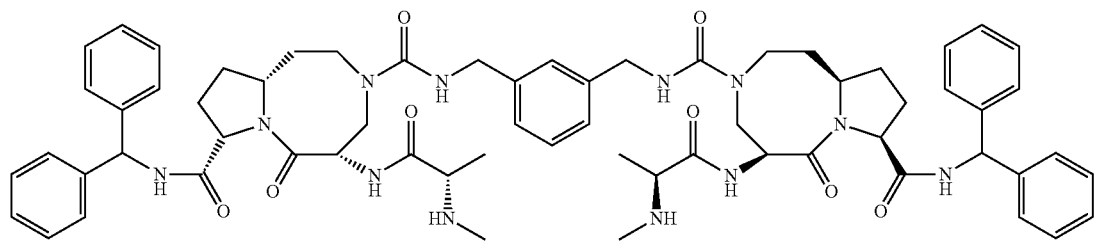
Example 3
$^1$H NMR (300 MHz, CD$_3$OD): δ 7.36-7.15 (m, 24H), 6.15 (s, 2H), 4.84 (m, 2H), 4.63 (m, 4H), 4.32-4.14 (m, 4H), 3.99-3.81 (m, 6H), 3.16-3.06 (m, 4H), 2.63 (s, 6H), 2.34 (m, 2H), 2.18-2.85 (m, 6H), 1.85-1.60 (m, 4H), 1.50 (d, J=7.2 Hz, 6H); ESI MS: m/z 1143.67 (M+H)$^+$.
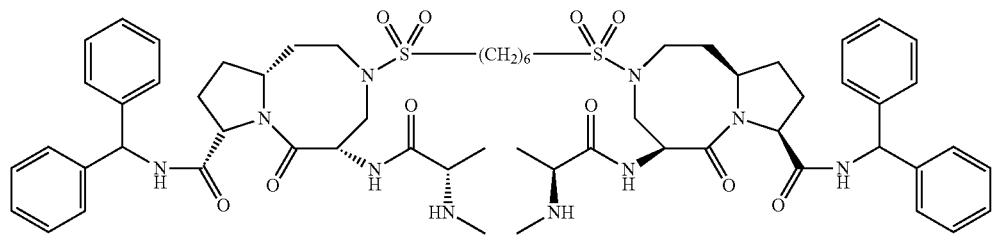
Example 9
$^1$H NMR (300 MHz, CD$_3$OD): δ 7.36 (m, 20H), 6.14 (s, 2H), 4.82 (m, 2H), 4.60 (t, J=8.4 Hz, 2H), 4.44 (m, 2H), 3.92-3.80 (m, 4H), 3.70 (m, 2H), 3.42 (m, 2H), 3.16-3.03 (m, 6H), 2.66 (s, 6H), 2.36 (m, 2H), 2.16 (m, 2H), 2.00 (m, 4H), 1.73 (m, 8H), 1.52-1.43 (m, 10H); ESI MS: m/z 1165.4 (M+H)$^+$.
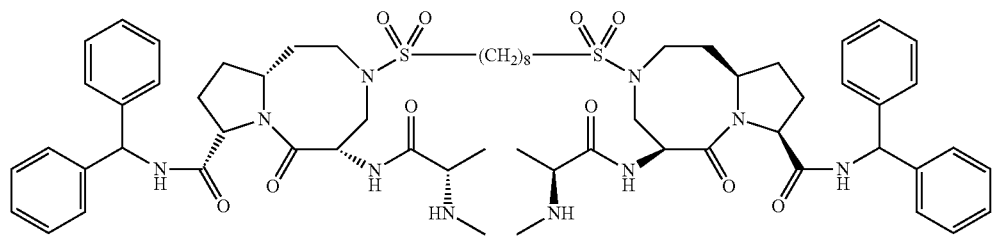
Example 10
$^1$H NMR (300 MHz, CD$_3$OD): δ 7.36-7.22 (m, 20H), 6.14 (s, 2H), 4.82 (m, 2H), 4.60 (t, J=8.4 Hz, 2H), 4.44 (m, 2H), 3.91-3.85 (m, 4H), 3.65 (m, 2H), 3.48 (m, 2H), 3.15-3.03 (m, 6H), 2.66 (s, 6H), 2.32 (m, 2H), 2.14 (m, 2H), 2.00 (m, 4H), 1.85-1.70 (m, 8H), 1.52 (d, J=8.7 Hz, 6H), 1.42-1.33 (m, 6H); ESI MS: m/z 1193.7 (M+H)$^+$.

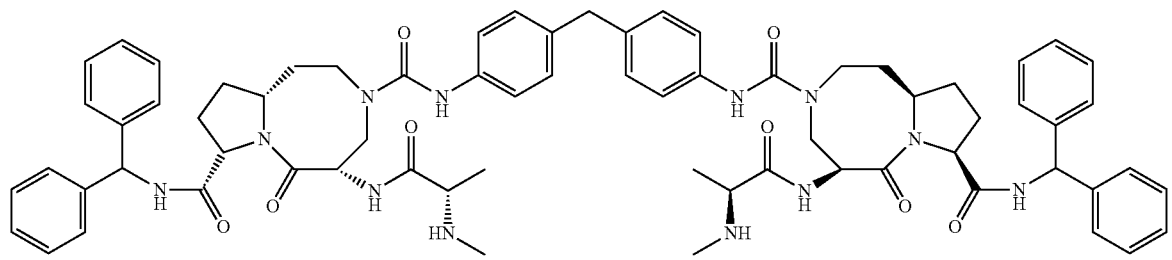
Example 11
$^1$H NMR (300 MHz, CD$_3$OD): δ 7.48 (d, J=8.1 Hz, 4H), 7.33 (m, 20H), 7.11 (d, J=8.1 Hz, 4H), 6.17 (s, 2H), 4.82 (m, 2H), 4.63 (m, 2H), 4.25 (m, 2H), 4.08-4.03 (m, 6H), 3.88 (s, 2H), 3.30-3.20 (m, 4H), 2.70 (s, 6H), 2.34 (m, 2H), 2.20-1.80 (m, 6H), 1.75-1.60 (m, 4H), 1.55 (d, J=6.9 Hz, 6H); ESI MS: m/z 1206.4 (M+H)$^+$.
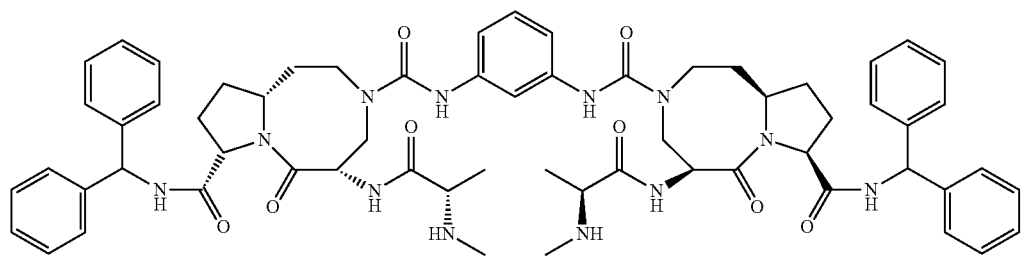
Example 14
$^1$H NMR (300 MHz, CD$_3$OD): δ 8.14 (m, 1H), 7.34-7.18 (m, 23H), 6.17 (s, 2H), 4.84 (m, 2H), 4.67 (t, J=8.4 Hz, 2H), 4.22 (m, 2H), 4.07 (m, 6H), 3.24 (m, 4H), 2.73 (s, 6H), 2.34 (m, 2H), 2.14-2.04 (m, 6H), 1.77-1.66 (m, 4H), 1.57 (d, J=6.9 Hz, 6H); ESI MS: m/z 1115.9 (M+H)$^+$.
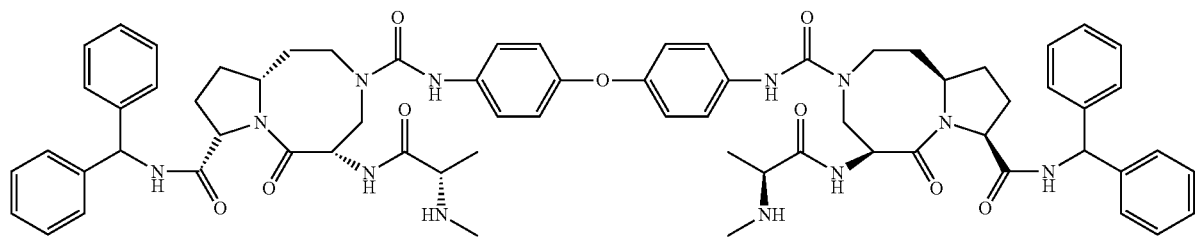
Example 15
$^1$H NMR (300 MHz, CD$_3$OD): δ 7.55 (d, J=9.0 Hz, 4H), 7.36-7.24 (m, 20H), 6.91 (d, J=9.0 Hz, 4H), 6.17 (m, 2H), 4.84 (m, 2H), 4.64 (t, J=8.1 Hz, 2H), 4.23 (m, 2H), 4.09 (m, 6H), 3.21 (m, 4H), 2.71 (s, 6H), 2.34 (m, 2H), 2.14-2.02 (m, 6H), 1.80-1.73 (m, 4H), 1.56 (d, J=6.9 Hz, 6H); ESI MS: m/z 1207.3 (M+H)$^+$.

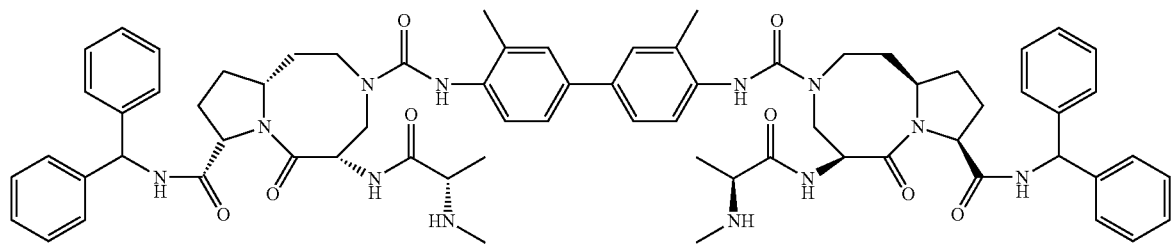
Example 16
¹H NMR (300 MHz, CD₃OD): δ 7.46-7.25 (m, 26H), 6.17 (s, 2H), 4.84 (m, 2H), 4.65 (m, 2H), 4.32 (m, 2H), 4.19-4.02 (m, 6H), 3.22 (m, 4H), 2.66 (s, 6H), 2.37 (s, 6H), 2.24-2.02 (m, 8H), 1.83-1.70 (m, 4H), 1.53 (d, J=6.6 Hz, 6H); ESI MS: m/z 1220.2 (M+H)⁺.
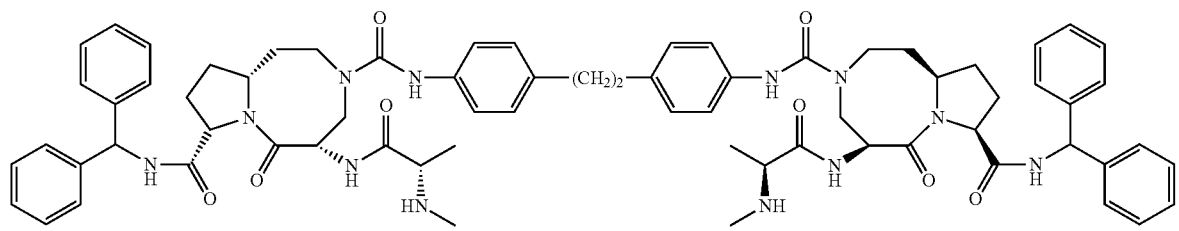
Example 18
¹H NMR (300 MHz, CD₃OD): δ7.47 (d, J=8.4 Hz, 4H), 7.36 (m, 20H), 7.06 (d, J=8.4 Hz, 4H), 6.16 (s, 2H), 4.94 (m, 2H), 4.67 (t, J=8.4 Hz, 2H), 4.25 (m, 2H), 4.09-4.04 (m, 6H), 3.17-3.28 (m, 4H), 2.84 (s, 4H), 2.66 (s, 6H), 2.37 (m, 2H), 2.15-2.02 (m, 6H), 1.79-1.67 (m, 4H), 1.56 (d, J=6.6 Hz, 6H); ESI MS: m/z 1220.25 (M+H)⁺.
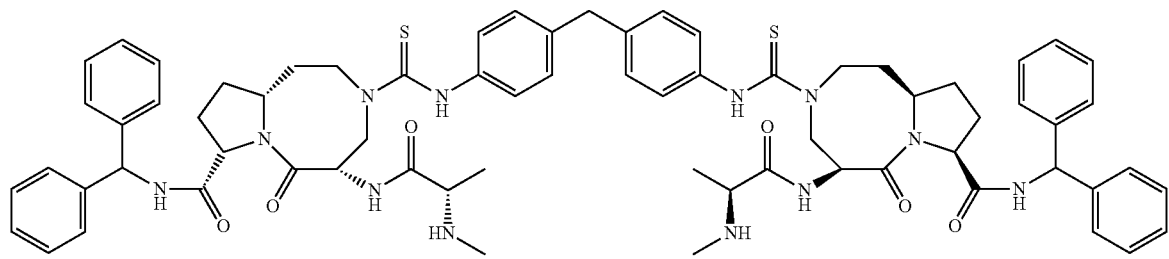
Example 19
¹H NMR (300 MHz, CD₃OD): δ 7.83 (d, J=8.4 Hz, 4H), 7.63 (d, J=8.4 Hz, 4H), 7.36-7.16 (m, 20H), 6.17 (s, 2H), 5.01 (m, 2H), 4.67 (m, 2H), 4.17 (m, 2H), 4.00-3.94 (m, 4H), 3.73 (s, 4H), 3.59-3.40 (m, 4H), 2.64 (s, 6H), 2.55-2.37 (m, 4H), 2.06 (m, 4H), 1.80-1.67 (m, 4H), 1.53 (d, J=6.9 Hz, 6H); ESI MS: m/z 1237.6 (M+H)⁺.

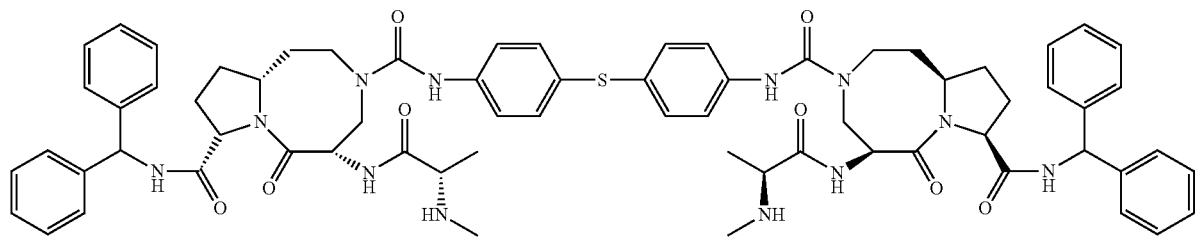
Example 20
¹H NMR (300 MHz, CD₃OD): δ 7.60 (d, J=8.4 Hz, 4H), 7.36-7.21 (m, 24H), 6.17 (s, 2H), 4.82 (m, 2H), 4.64 (t, J=8.1 Hz, 2H), 4.21 (m, 2H), 4.08-4.02 (m, 6H), 3.24 (m, 4H), 2.70 (s, 6H), 2.24 (m, 2H), 2.14-2.03 (m, 6H), 1.78-1.71 (m, 4H), 1.56 (d, J=6.9 Hz, 6H); ESI MS: m/z 1223.3 (M+H)⁺.
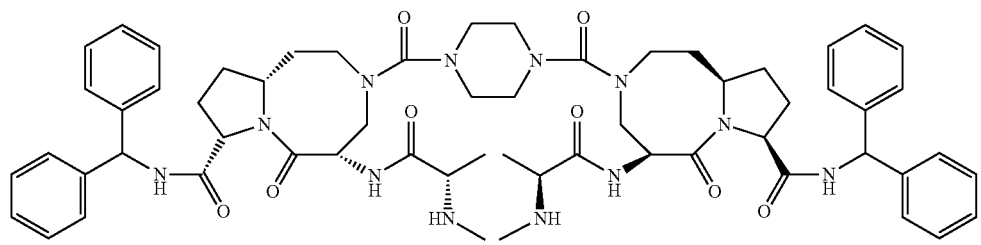
Example 21
¹H NMR (300 MHz, CD₃OD): δ 7.33-7.21 (m, 20H), 6.12 (s, 2H), 5.11 (m, 2H), 4.84 (m, 2H), 4.56 (t, J=8.4 Hz, 2H), 4.25 (m, 2H), 3.93 (m, 2H), 3.66-3.53 (m, 6H), 3.22-3.15 (m, 8H), 2.67 (s, 6H), 2.34 (m, 2H), 2.15-1.96 (m, 4H), 1.83-1.77 (m, 6H), 1.54 (d, J=6.9 Hz, 6H); ESI MS: m/z 1093.7 (M+H)⁺.
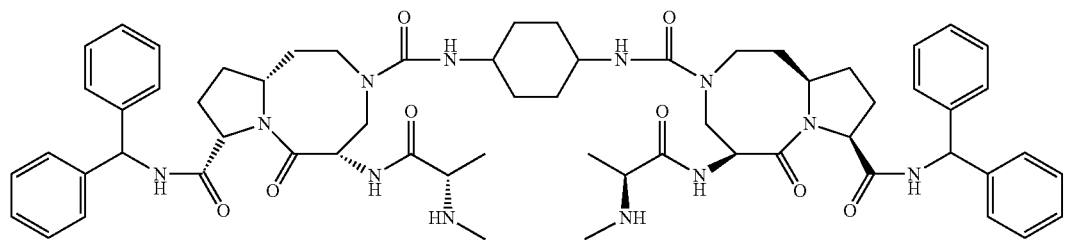
Example 22
¹H NMR (300 MHz, CD₃OD): δ 7.34-7.23 (m, 20H), 6.14 (s, 2H), 4.92 (m, 2H), 4.70 (m, 4H), 4.08-3.86 (m, 8H), 3.59 (m, 2H), 3.16-3.05 (m, 4H), 2.70 (s, 6H), 2.36 (m, 2H), 2.10-1.92 (m, 10H), 1.79-1.71 (m, 4H), 1.60-1.40 (m, 8H), 1.40-1.25 (m, 2H); ESI MS: m/z 1121.7 (M+H)⁺.

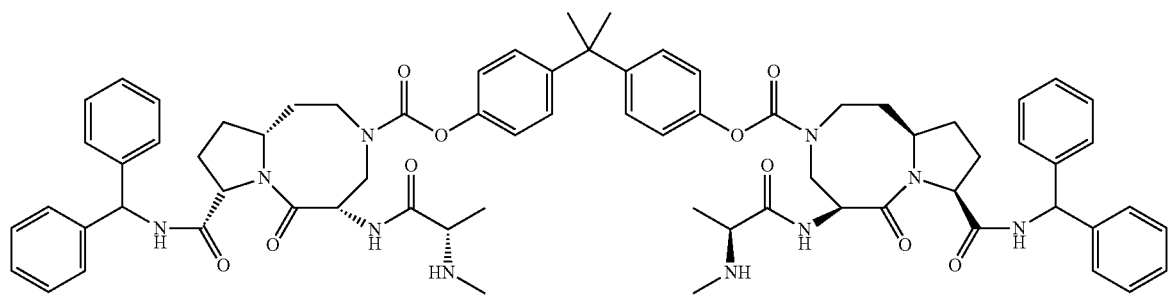
Example 23
¹H NMR (300 MHz, CD₃OD): δ 7.27-7.02 (m, 28H), 6.12 (m, 2H), 5.07-4.97 (m, 2H), 4.60 (m, 2H), 4.39 (m, 2H), 3.89-3.85 (m, 4H), 3.73-3.54 (m, 6H), 2.66 (s, 6H), 2.31 (m, 2H), 2.11-1.81 (m, 10H), 1.65 (m, 6H) 1.56 (d, J=6.9 Hz, 6H); ESI MS: m/z 1236.2 (M+H)⁺.
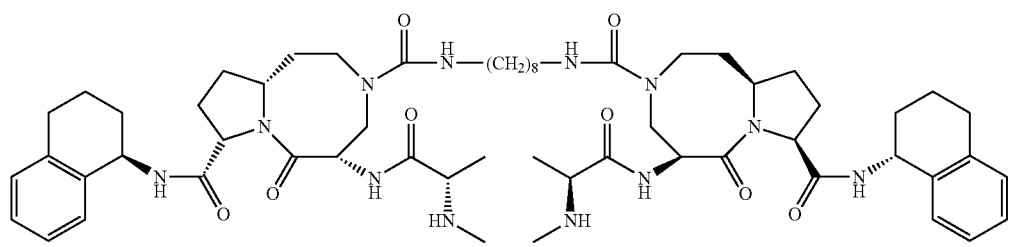
Example 4
¹H NMR (300 MHz, CD₃OD): δ 7.40 (m, 2H), 7.14-7.06 (m, 6H), 5.06 (m, 2H), 4.84 (m, 2H), 4.72 (m, 2H), 4.50 (t, J=8.4 Hz, 2H), 4.12 (m, 2H), 4.02-3.93 (m, 6H), 3.27-3.10 (m, 6H), 2.80 (m, 4H), 2.67 (s, 6H), 2.34 (m, 2H), 2.14-1.90 (m, 10H), 1.81-1.72 (m, 8H), 1.58 (m, 4H), 1.53 (d, J=6.9 Hz, m, 6H), 1.35 (m, 8H); ESI MS: m/z 1151.8 (M+H)⁺.
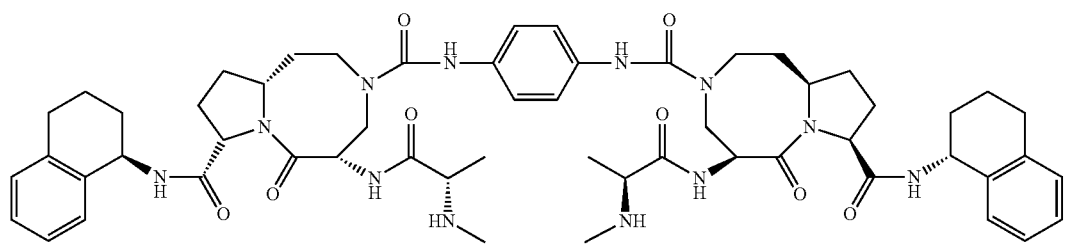
Example 5
¹H NMR (300 MHz, CD₃OD): δ 7.55 (s, 4H), 7.43 (m, 2H), 7.17-7.07 (m, 6H), 5.09 (m, 2H), 4.83 (m, 2H), 4.52 (t, J=8.4 Hz, 2H), 4.25 (m, 2H), 4.16-4.05 (m, 6H), 3.39-3.34 (m, 4H), 2.81 (m, 4H), 2.73 (s, 6H), 2.32 (m, 4H), 2.05-1.93 (m, 8H), 1.82-1.74 (m, 8H), 1.57 (d, J=6.9 Hz, m, 6H); ESI MS: m/z 1044.0 (M+H)⁺.

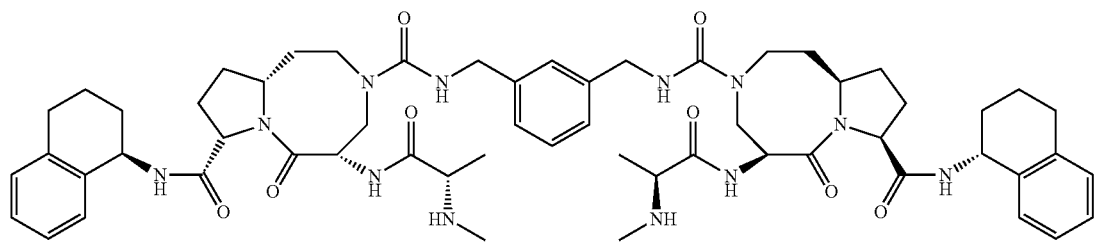
Example 6
¹H NMR (300 MHz, CD₃OD): δ 7.38-7.09 (m, 12H), 5.03 (m, 2H), 4.85 (m, 2H), 4.78 (m, 2H), 4.60 (m, 2H), 4.55 (t, J=8.4 Hz, 2H), 4.35-4.17 (m, 4H), 4.05-3.92 (m, 6H), 3.61 (m, 2H), 2.80 (m, 4H), 2.66 (s, 6H), 2.31 (m, 2H), 2.15-1.91 (m, 10H), 1.78-1.72 (m, 8H), 1.51 (d, J=6.9 Hz, m, 6H); ESI MS: m/z 1071.63 (M+H)⁺.
Example 12
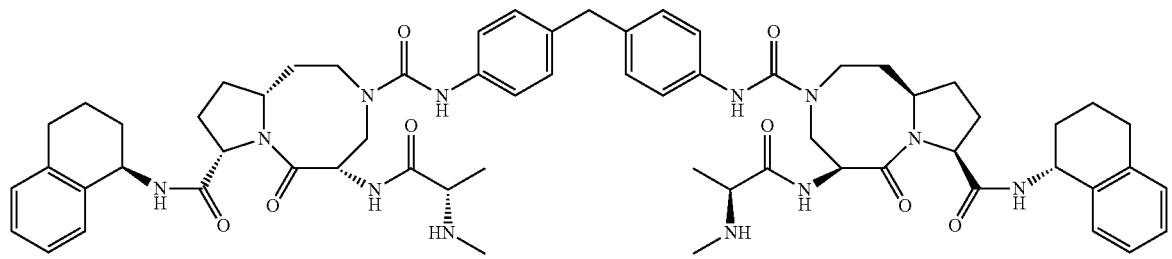
¹H NMR (300 MHz, CD₃OD): δ 7.51 (d, J=8.4 Hz, 4H), 7.43 (m, 2H), 7.14-7.07 (m, 10H), 5.08 (m, 2H), 4.82 (m, 2H), 4.51 (t, J=8.4 Hz, 2H), 4.28 (m, 2H), 4.15-4.04 (m, 6H), 3.89 (s, 2H), 3.38-3.33 (m, 4H), 2.87 (m, 4H), 2.71 (s, 6H), 2.31 (m, 2H), 2.10-1.73 (m, 18H), 1.56 (d, J=6.9 Hz, m, 6H); ESI MS: m/z 1134.1 (M+H)⁺.
Example 24
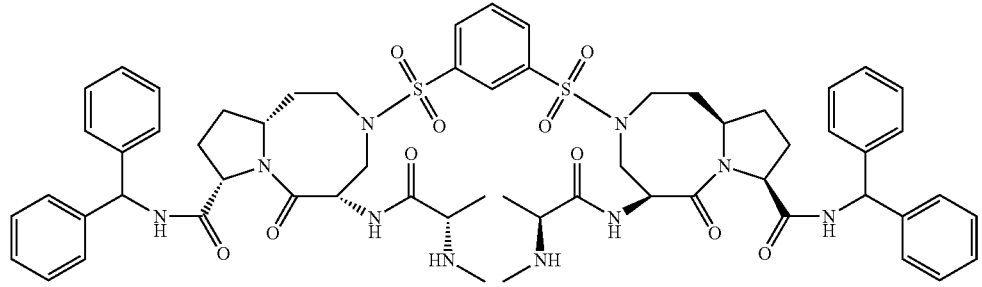
¹H NMR (300 MHz, CD₃OD): δ 8.21 (m, 3H), 7.85 (m, 1H), 7.34-7.18 (m, 20H), 6.10 (s, 2H), 4.85 (m, 2H), 4.58 (t, J=8.4 Hz, 2H), 4.31 (m, 2H), 3.93 (m, 4H), 3.73 (m, 2H), 3.21 (m, 2H), 2.96 (m, 2H), 2.67 (s, 6H), 2.33 (m, 2H), 2.06-1.93 (m, 6H), 1.84-1.76 (m, 4H), 1.51 (d, J=6.9 Hz, 6H); ESI MS: m/z 1157.6 (M+H)⁺.

Example 38
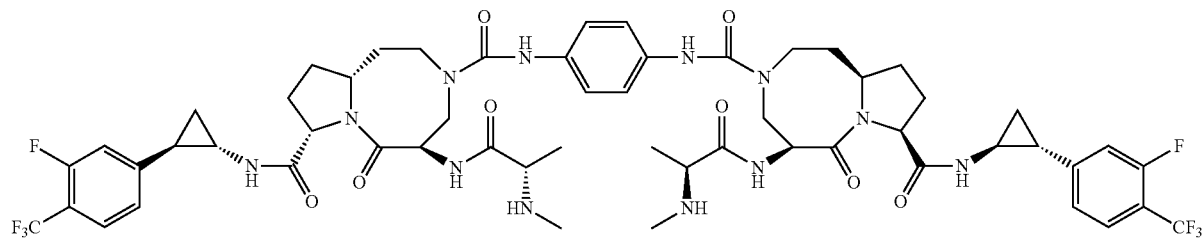
$^1$H NMR (300 MHz, D$_2$O): δ 7.50-6.70 (m, 10H), 4.90 (m, 2H), 4.70 (m, 2H), 4.45-4.10 (m, 4H), 3.95-3.40 (m, 10H), 2.60 (m, 2H), 2.55 (s, 6H), 2.30-1.60 (m, 12H), 1.45 (brd, J=7.0 Hz, 6H), 1.40-1.05 (m, 4H); ESI MS: m/z 1187.3 (M+H)$^+$.
Example 37
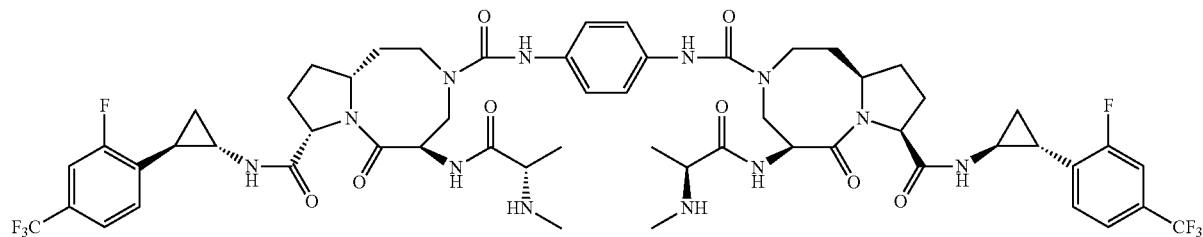
$^1$H NMR (300 MHz, D$_2$O): δ 7.50-6.70 (m, 10H), 4.92 (m, 2H), 4.80 (m, 2H), 4.45-4.20 (m, 4H), 3.95 (m, 2H), 3.80-3.40 (m, 8H), 2.60 (m, 2H), 2.55 (s, 6H), 2.30-1.60 (m, 12H), 1.45 (brd, J=7.0 Hz, 6H), 1.40-1.05 (m, 4H); ESI MS: m/z 1187.3 (M+H)$^+$.
Example 36
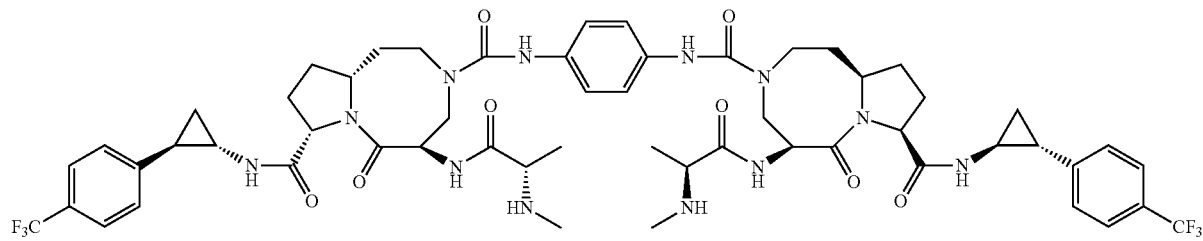
$^1$H NMR (300 MHz, D$_2$O): δ 7.65-7.45 (m, 4H), 7.35-6.90 (m, 8H), 5.05 (m, 2H), 4.80 (m, 2H), 4.50-4.30 (m, 4H), 4.05 (m, 2H), 3.90-3.40 (m, 8H), 2.60 (m, 2H), 2.50 (s, 6H), 2.40-1.60 (m, 12H), 1.45 (brd, J=7.0 Hz, 6H), 1.40-1.05 (m, 4H); ESI MS: m/z 1151.2 (M+H)$^+$.

Example 26
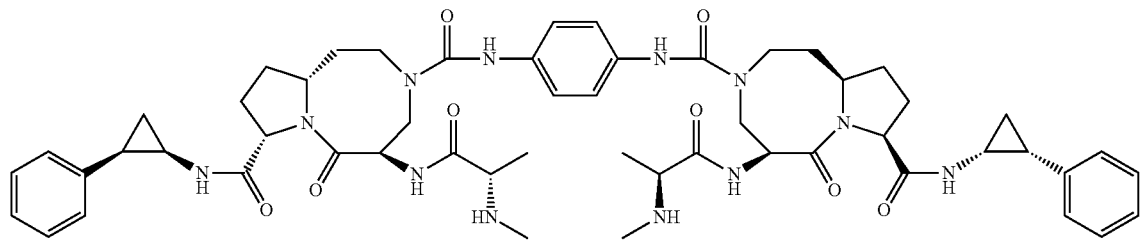 [SMILES: CN[C@@H](C)C(=O)N[C@H]1CN(C(=O)Nc2ccc(NC(=O)N3CC[C@H]4CC[C@@H](C(=O)N[C@@H]5C[C@@H]5c5ccccc5)N4C(=O)[C@@H](NC(=O)[C@H](C)NC)C3)cc2)CC[C@H]2CC[C@@H](C(=O)N[C@@H]3C[C@@H]3c3ccccc3)N2C1=O]
$^1$H NMR (300 MHz, D$_2$O): δ 7.35-7.05 (m, 14H), 4.75 (m, 2H), 4.20-3.90 (m, 4H), 3.90-3.65 (m, 6H), 3.35-3.10 (m, 4H), 2.90 (m, 2H), 2.60 (s, 6H), 2.30 (m, 2H), 2.05-1.55 (m, 8H), 1.45 (brd, J=7.2 Hz, 6H), 1.40-1.05 (m, 6H), 0.80 (m, 2H); ESI MS: m/z 1015.5 (M+H)$^+$.
Example 27
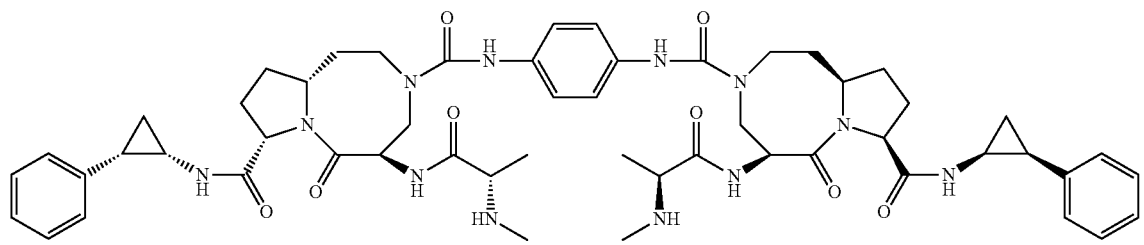 [SMILES: CN[C@@H](C)C(=O)N[C@H]1CN(C(=O)Nc2ccc(NC(=O)N3CC[C@H]4CC[C@@H](C(=O)N[C@H]5C[C@H]5c5ccccc5)N4C(=O)[C@@H](NC(=O)[C@H](C)NC)C3)cc2)CC[C@H]2CC[C@@H](C(=O)N[C@H]3C[C@H]3c3ccccc3)N2C1=O]
$^1$H NMR (300 MHz, D$_2$O): δ 7.35-7.05 (m, 14H), 4.75 (m, 2H), 4.30-3.95 (m, 4H), 3.95-3.65 (m, 6H), 3.40-3.10 (m, 4H), 2.90 (m, 2H), 2.60 (s, 6H), 2.25 (m, 2H), 2.05-1.55 (m, 8H), 1.45 (brd, J=7.2 Hz, 6H), 1.40-1.05 (m, 6H), 0.80 (m, 2H); ESI MS: m/z 1015.5 (M+H)$^+$.
Example 30
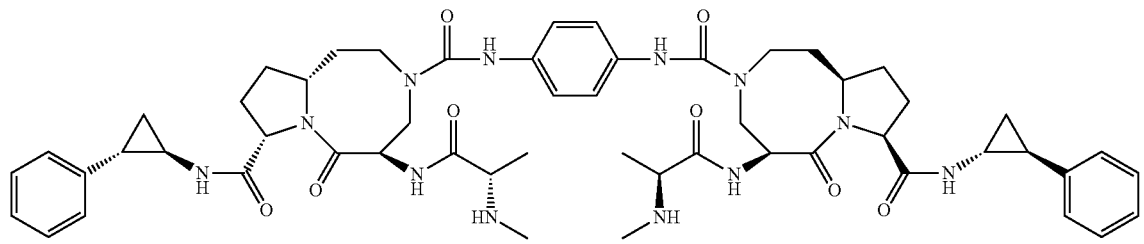
$^1$H NMR (300 MHz, CD$_3$OD): δ 7.60 (s, 4H), 7.30-7.10 (m, 10H), 4.80 (m, 2H), 4.45 (m, 2H), 4.25 (m, 2H), 4.20-4.02 (m, 6H), 3.50-3.30 (m, 4H), 2.95 (m, 2H), 2.70 (s, 6H), 2.40-2.05 (m, 10H), 1.90-1.70 (m, 4H), 1.55 (d, J=7.2 Hz, 6H), 1.30-1.10 (m, 4H); ESI MS: m/z 1015.5 (M+H)$^+$.

Example 31
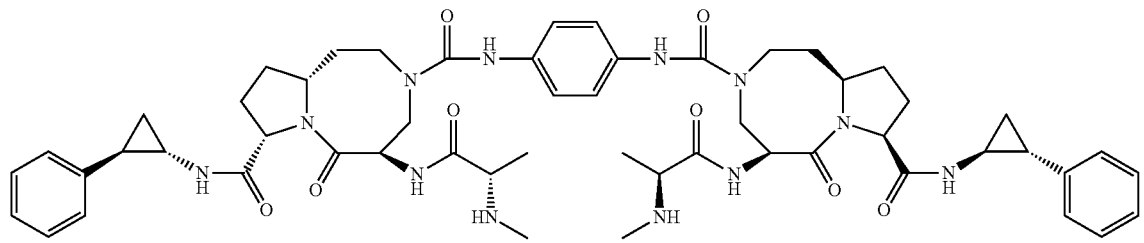
¹H NMR (300 MHz, CD₃OD): δ 7.60 (s, 4H), 7.30-7.10 (m, 10H), 4.80 (m, 2H), 4.45 (m, 2H), 4.30 (m, 2H), 4.20-4.02 (m, 6H), 3.50-3.30 (m, 4H), 2.90 (m, 2H), 2.70 (s, 6H), 2.35-2.05 (m, 10H), 1.90-1.70 (m, 4H), 1.55 (d, J=7.2 Hz, 6H), 1.30-1.10 (m, 4H); ESI MS: m/z 1015.5 (M+H)⁺.
Example 29
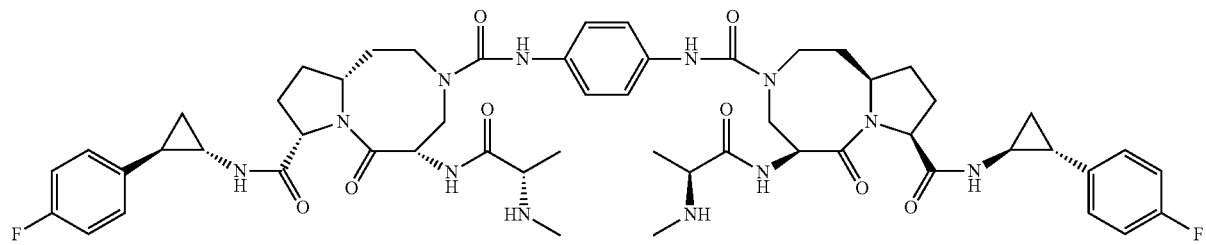 [SMILES: CN[C@@H](C)C(=O)N[C@H]1CN(C(=O)Nc2ccc(NC(=O)N3CC[C@H]4CC[C@@H](C(=O)N[C@H]5C[C@@H]5c5ccc(F)cc5)N4C(=O)[C@@H](NC(=O)[C@H](C)NC)C3)cc2)CC[C@H]2CC[C@@H](C(=O)N[C@H]3C[C@@H]3c3ccc(F)cc3)N2C1=O]
¹H NMR (300 MHz, D₂O): δ 7.30-6.90 (m, 12H), 4.90 (m, 2H), 4.70 (m, 2H), 4.40-4.20 (m, 4H), 3.95 (m, 2H), 3.90-3.30 (m, 8H), 2.65 (m, 2H), 2.60 (s, 6H), 2.30-1.75 (m, 12H), 2.50 (d, J=7.0 Hz, 6H), 1.20 (m, 4H); ESI MS: m/z 1051.2 (M+H)⁺.
Example 28
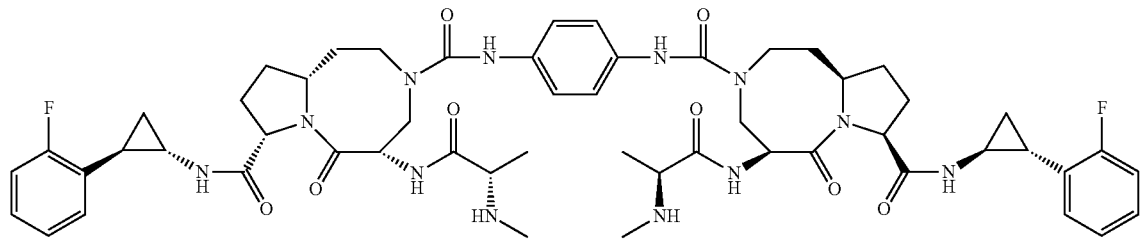
¹H NMR (300 MHz, CD₃OD): δ 7.30-6.80 (m, 12H), 4.85 (m, 2H), 4.70 (m, 2H), 4.30-4.20 (m, 4H), 4.05-3.60 (m, 6H), 3.50-3.30 (m, 4H), 2.65 (m, 2H), 2.55 (s, 6H), 2.30-1.70 (m, 12H), 2.50 (d, J=7.0 Hz, 6H), 1.20 (m, 4H); ESI MS: m/z 1051.2 (M+H)⁺.

Example 25
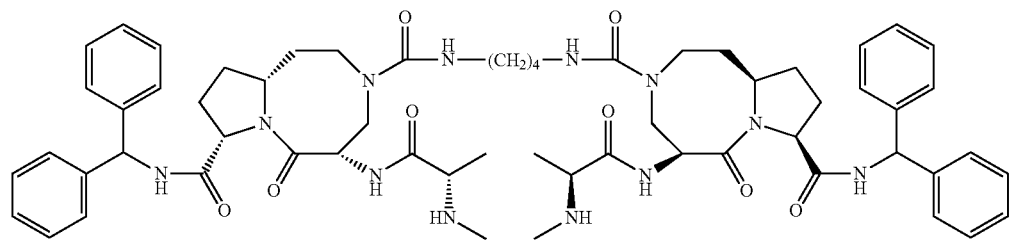
$^1$H NMR (300 MHz, D$_2$O): δ 7.40-7.20 (m, 10H), 5.99 (s, 2H), 4.75 (m, 2H), 4.45 (m, 2H), 4.10 (m, 2H), 3.95 (m, 2H), 3.80 (m, 2H), 3.65 (m, 2H), 3.25-3.05 (m, 8H), 2.62 (m, 6H), 2.30 (m, 2H), 2.20-1.70 (m, 12H), 1.45 (m, 2H), 1.40 (d, J=7.2 Hz, 6H); ESI MS: m/z 1095.4 (M+H)$^+$.
Example 39
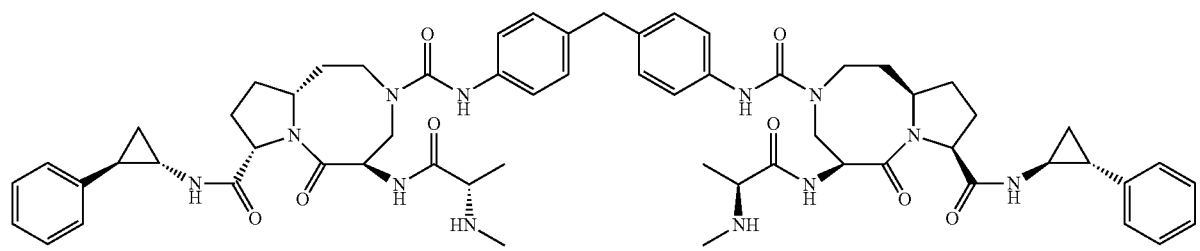
$^1$H NMR (300 MHz, CD$_3$OD): δ 7.48-7.08 (m, 18H), 4.92 (m, 2H), 4.42 (m, 2H), 4.21-4.03 (m, 8H), 3.87 (m, 2H), 3.36-3.20 (m, 4H), 2.85 (m, 2H), 2.70 (s, 6H), 2.30-2.02 (m, 10H), 1.76 (m, 4H), 1.56 (d, J=6.9 Hz, 6H), 1.23 (m, 4H); ESI MS: m/z 1105.4 (M+H)$^+$.
Example 40
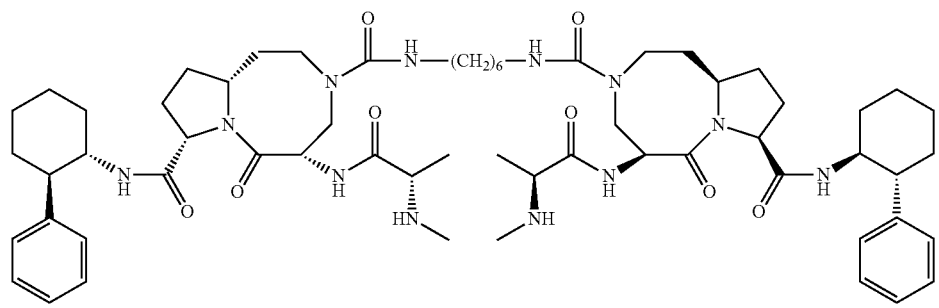
$^1$H NMR (300 MHz, CD$_3$OD) δ 7.35-7.15 (m, 10H), 4.84 (m, 2H), 4.40-3.90 (m, 8H), 3.75-3.50 (m, 6H), 3.40-3.20 (m, 8H), 2.71 (s, 6H), 2.65 (m, 2H), 1.90-1.43 (m, 42H); ESI MS: m/z 1107.9 (M+H)$^+$.

Example 41
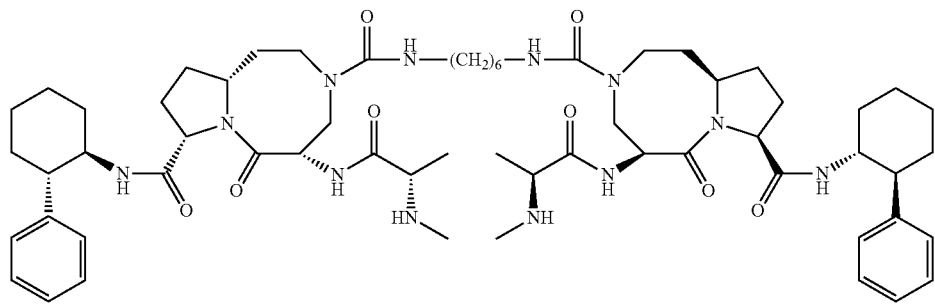
$^1$H NMR (300 MHz, CD$_3$OD): δ 7.35-7.20 (m, 10H), 4.84 (m, 2H), 4.61 (d, J=9.0 Hz, 2H), 4.20 (t, J=9.0 Hz, 2H), 3.97-3.81 (m, 10H), 3.30-2.95 (m, 6H), 2.68 (s, 6H), 2.51 (m, 2H), 2.01-1.31 (m, 42H); ESI MS: m/z 1107.6 (M+H)$^+$.
Example 42
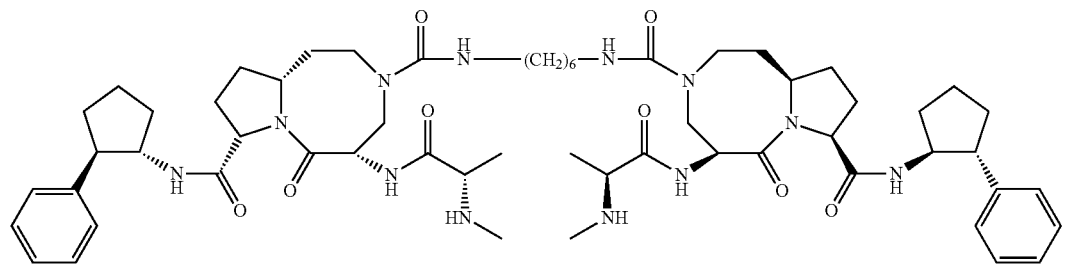
$^1$H NMR (300 MHz, CD$_3$OD): δ 7.35-7.10 (m, 10H), 4.84 (m, 2H), 4.66 (m, 2H), 4.43 (m, 2H), 4.22 (m, 2H), 4.04-3.72 (m, 8H), 3.10-2.85 (m, 6H), 2.68 (s, 6H), 2.24-1.37 (m, 40H); ESI MS: m/z 1079.5 (M+H)$^+$.
Example 43
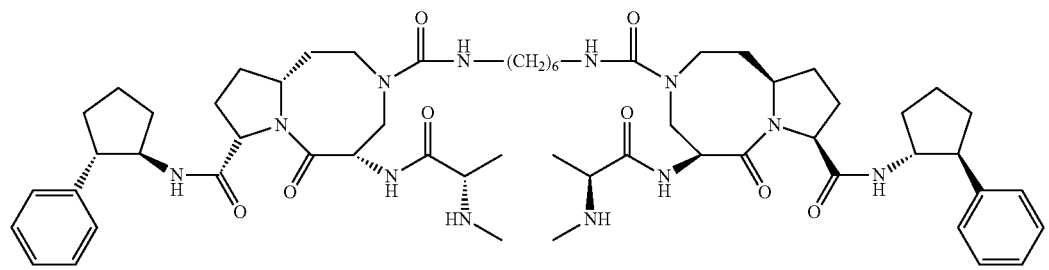
$^1$H NMR (300 MHz, CD$_3$CD): δ 7.35-7.15 (m, 10H), 4.81 (m, 2H), 4.65 (m, 2H), 4.35 (m, 2H), 4.22 (m, 2H), 3.98-3.80 (m, 8H), 3.25-2.87 (m, 6H), 2.68 (s, 6H), 2.20-1.33 (m, 40H); ESI MS: m/z 1079.9 (M+H)$^+$.

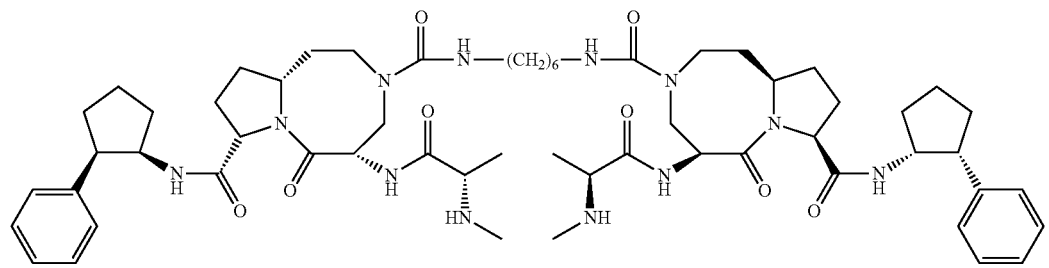
Example 44
$^1$H NMR (300 MHz, CD$_3$OD): δ 7.30-7.10 (m, 10H), 4.84 (m, 2H), 4.61 (m, 4H), 4.24 (t, J=9.0 Hz, 2H), 3.97-3.81 (m, 8H), 3.41-3.02 (m, 6H), 2.64 (s, 6H), 2.17-1.37 (m, 40H); ESI MS: m/z 1079.3 (M+H)$^+$.
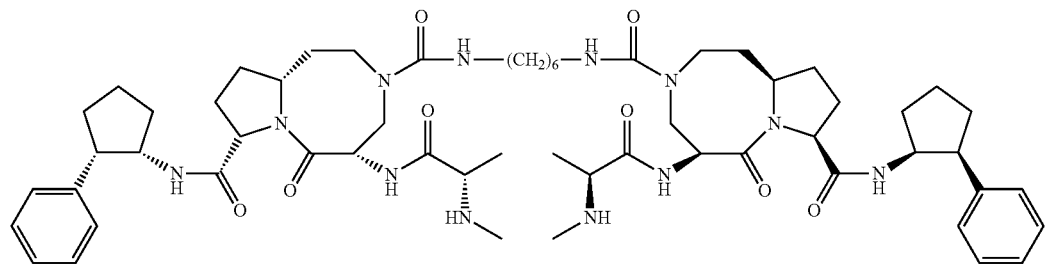
Example 45
$^1$H NMR (300 MHz, CD$_3$OD): δ 7.35-7.10 (m, 10H), 4.84 (m, 2H), 4.67-4.24 (m, 6H), 3.97-3.81 (m, 8H), 3.41-3.02 (m, 6H), 2.68 (s, 6H), 2.17-1.37 (m, 40H); ESI MS: m/z 1079.5 (M+H)$^+$.
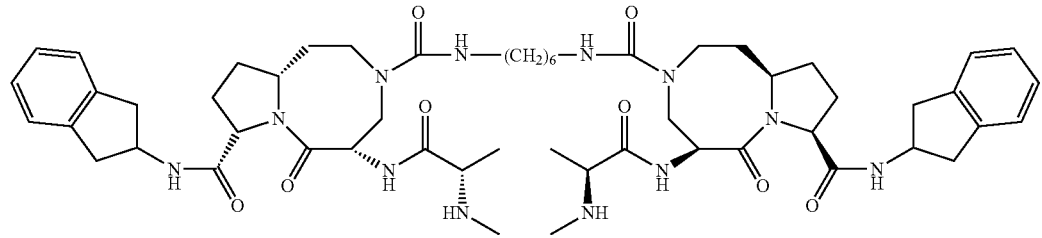
Example 46
$^1$H NMR (300 MHz, CD$_3$OD): δ 7.19-7.11 (m, 8H), 4.84 (m, 2H), 4.70 (m, 2H), 4.57 (m, 2H), 4.42 (m, 2H), 4.10 (m, 2H), 4.00 (m, 6H), 3.22-3.06 (m, 6H), 2.92-2.75 (m, 4H), 2.66 (s, 6H), 2.26-1.37 (m, 30H); ESI MS: m/z 1023.7 (M+H)$^+$.
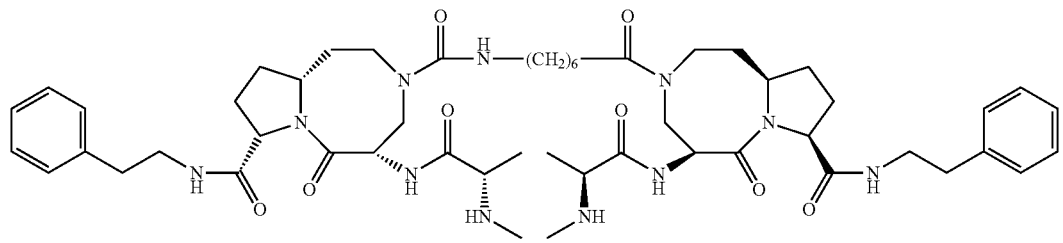
Example 47

¹H NMR (300 MHz, CD₃OD): δ 7.35-7.15 (m, 10H), 4.84 (m, 2H), 4.71 (m, 2H), 4.41 (m, 2H), 4.11 (m, 2H), 3.98-3.88 (m, 6H), 3.48-3.08 (m, 10H), 2.82 (m, 4H), 2.69 (s, 6H), 2.22-1.39 (m, 26H); ESI MS: m/z 999.7 (M+H)⁺.
Example 48
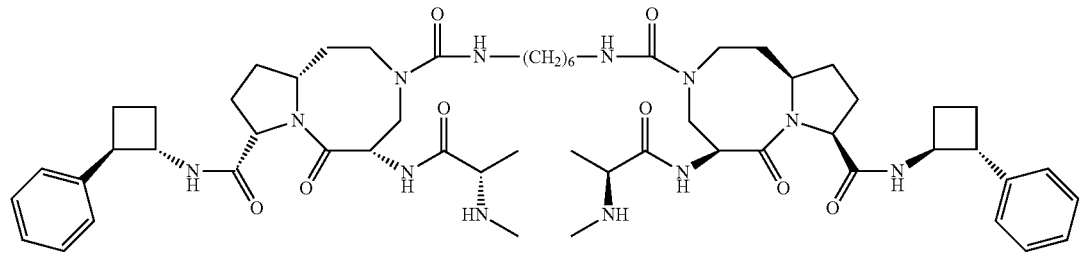
¹H NMR (300 MHz, CD₃OD): δ 7.35-7.15 (m, 10H), 4.84 (m, 2H), 4.69 (m, 2H), 4.50-4.30 (m, 4H), 4.11-3.86 (m, 8H), 3.48 (m, 2H), 3.25-3.06 (m, 6H), 2.68 (s, 6H), 2.31-1.28 (m, 34H); ESI MS: m/z 1051.4 (M+H)⁺.
Example 49
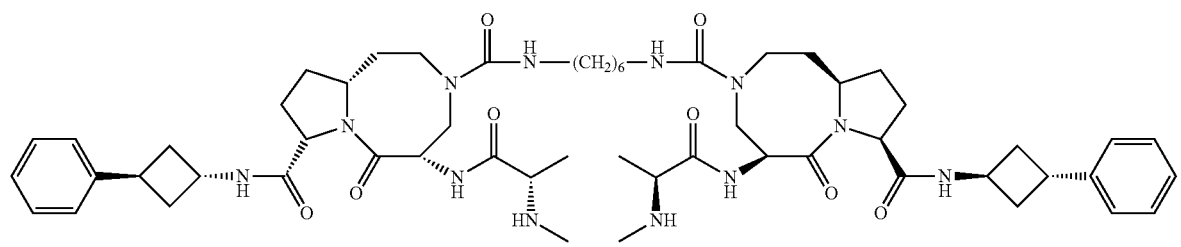
¹H NMR (300 MHz, CD₃OD): δ 7.35-7.10 (m, 10H), 4.82 (m, 2H), 4.70 (d, J=8.4 Hz, 2H), 4.43-4.34 (m, 4H), 4.12 (m, 2H), 4.01-3.90 (m, 6H), 3.65 (m, 2H), 3.25-3.06 (m, 6H), 2.67 (s, 6H), 2.52-2.34 (m, 10H), 2.10 (m, 6H), 1.80-1.39 (18H); ESI MS: m/z 1051.9 (M+H)⁺.
Example 50
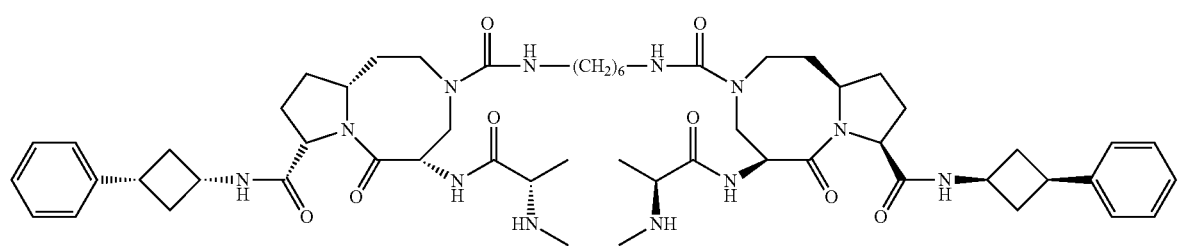
¹H NMR (300 MHz, CD₃OD): δ 7.35-7.15 (m, 10H), 4.82 (m, 2H), 4.70 (d, J=9.0 Hz, 2H), 4.43-4.28 (m, 4H), 4.12 (m, 2H), 4.01-3.90 (m, 6H), 3.25-3.06 (m, 6H), 2.77 (m, 2H), 2.70 (s, 6H), 2.51 (m, 2H), 2.30 (m, 2H), 2.20-1.90 (m, 10H), 1.90-1.45 (m, 16H), 1.45-1.35 (m, 4H); ESI MS: m/z 1051.7 (M+H)⁺.

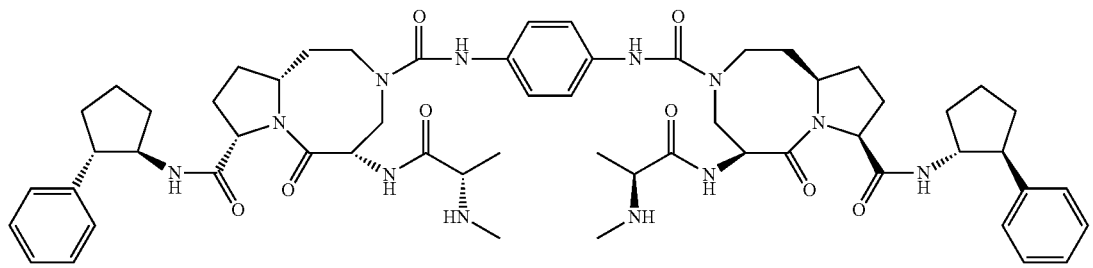
Example 32
¹H NMR (300 MHz, D$_2$O): δ 7.35-7.10 (m, 14H), 4.80 (m, 2H), 4.40-4.25 (m, 4H), 4.20 (m, 2H), 4.15-4.05 (m, 4H), 3.90 (m, 2H), 3.40-3.30 (m, 4H), 2.90 (m, 2H), 2.70 (s, 6H), 2.30-1.90 (m, 10H), 1.90-1.55 (m, 14H), 1.55 (d, J=7.2 Hz, 6H); ESI MS: m/z 1071.5 (M+H)$^+$.
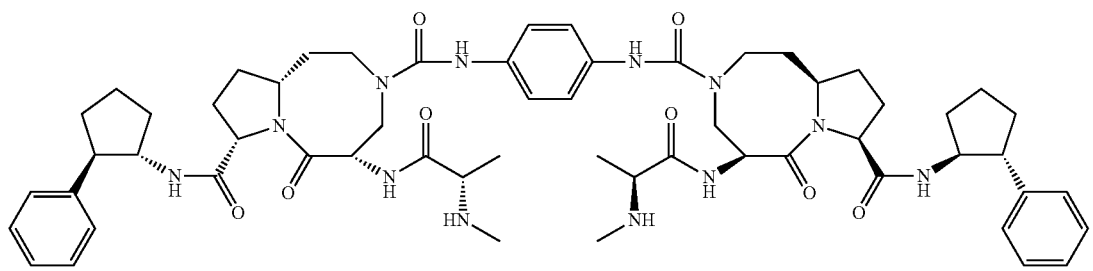
Example 33
¹H NMR (300 MHz, D$_2$O): δ 7.35-7.10 (m, 14H), 4.75 (m, 2H), 4.40-4.25 (m, 4H), 4.20 (m, 2H), 4.15-4.05 (m, 4H), 3.90 (m, 2H), 3.40-3.30 (m, 4H), 2.90 (m, 2H), 2.70 (s, 6H), 2.30-1.90 (m, 10H), 1.90-1.35 (m, 20H); ESI MS: m/z 1071.7 (M+H)$^+$.
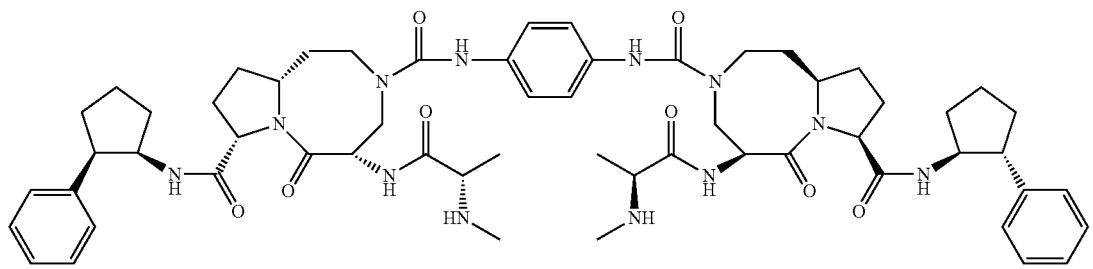
Example 34
¹H NMR (300 MHz, D$_2$O): δ 7.35-7.10 (m, 14H), 4.80 (m, 2H), 4.40 (m, 2H), 4.25-4.05 (m, 4H), 4.05-3.85 (m, 4H), 3.80 (m, 2H), 3.30-3.15 (m, 6H), 2.70 (s, 6H), 2.30-1.60 (m, 24H), 1.55 (d, J=7.2 Hz, 6H); ESI MS: m/z 1071.7 (M+H)$^+$.

Example 35
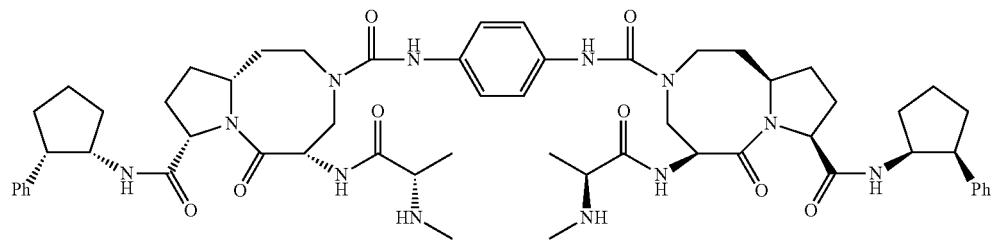
$^1$H NMR (300 MHz, D$_2$O): δ 7.35-7.10 (m, 14H), 4.80 (m, 2H), 4.45 (m, 2H), 4.20-3.90 (m, 6H), 3.80 (m, 2H), 3.30-3.20 (m, 6H), 2.70 (s, 6H), 2.30-1.60 (m, 24H), 1.55 (d, J=7.2 Hz, 6H); ESI MS: m/z 1071.7 (M+H)$^+$.
Example 7
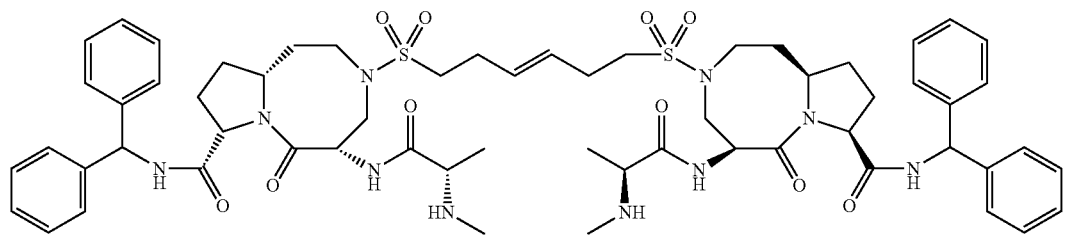
$^1$H NMR (300 MHz, CD$_3$OD): δ 7.40-7.20 (m, 20H), 6.15 (m, 2H), 5.60 (m, 2H), 4.85 (m, 2H), 4.55 (m, 2H), 4.40 (m, 2H), 3.95-3.80 (m, 4H), 3.65 (m, 2H), 3.35-2.05 (m, 6H), 2.65 (s, 6H), 2.45-1.70 (m, 16H), 1.55 (d, J=7.2 Hz, 6H); ESI MS: m/z 1162.5 (M+H)$^+$.
Example 8
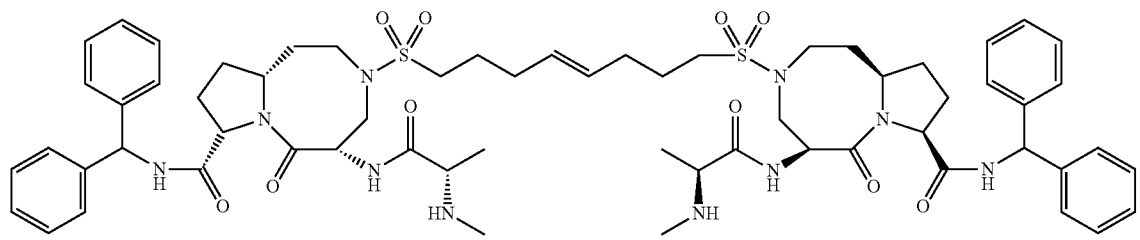
$^1$H NMR (300 MHz, CD$_3$OD): δ 7.40-7.20 (m, 20H), 6.15 (m, 2H), 5.45 (m, 2H), 4.82 (m, 2H), 4.55 (m, 2H), 4.40 (m, 2H), 3.95-3.72 (m, 4H), 3.65 (m, 2H), 3.35-2.95 (m, 6H), 2.65 (s, 6H), 2.45-1.70 (m, 20H), 1.55 (d, J=7.2 Hz, 6H); ESI MS: m/z 1190.6 (M+H)$^+$.
Example 17
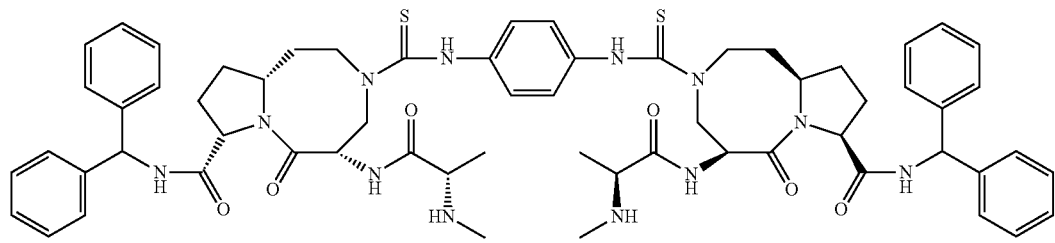
ESI MS: m/z 1147.6 (M+H)$^+$.

Binding Affinities to XIAP Linker-BIR2-BIR3, cIAP1-BIR3, and cIAP-2 BIR2

Binding affinities of the present compounds to XIAP linker-BIR2-BIR3 (residues 120-356), cIAP1-BIR3 (residues 253-363), and cIAP-2 BIR3 (residues 238-349) proteins were determined by fluorescence polarization (FP) based competitive assays. For cIAP-1 BIR3 and cIAP-2 BIR3 assays, a fluorescently labeled Smac mimetic (Smac-2F) was used as the fluorescent probe. The $K_d$ values of Smac-2F to cIAP-1 BIR3 and cIAP-2 BIR3 were determined by monitoring the total fluorescence polarization of mixtures composed with the fluorescent probe at a fixed concentration and proteins with increasing concentrations up to full saturation. Fluorescence polarization values were measured using the Infinite M-1000 plate reader (Tecan U.S., Research Triangle Park, N.C.) in Microfluor 2 96-well, black, round-bottom plates (Thermo Scientific). To each well, 1 nM of SMAC-2F and increasing concentrations of protein were added to a final volume of 125 µl in the assay buffer (100 mM potassium phosphate, pH 7.5, 100 µg/ml bovine γ-globulin, 0.02% sodium azide, Invitrogen, with 4% DMSO). Plates were incubated at room temperature for 1-2 hours and mixed with gentle shaking to assure equilibrium. The polarization values in millipolarization units (mP) were measured at an excitation wavelength of 485 nm and an emission wavelength of 530 nm. Equilibrium dissociation constants ($K_d$) were then calculated by fitting the sigmoidal dose-dependent FP increases as a function of protein concentrations using Graphpad Prism 5.0 software (Graphpad Software, San Diego, Calif.).

The $K_i$ values of compounds were determined through a compound dose-dependent competitive binding experiment in which serial dilutions of compounds competed against fixed concentration of the fluorescent probe for binding to a fixed concentration of the protein (typically 2 to 3 times the $K_d$ values determined above). Mixtures of 5 µl of the tested compounds in DMSO and 120 µl of preincubated protein/tracer complex in the assay buffer (100 mM potassium phosphate, pH 7.5, 100 µg/ml bovine γ-globulin, 0.02% sodium azide, Invitrogen) were added into assay plates and incubated at room temperature for 2 hours with gentle shaking. Final concentrations of proteins and probes were 3 nM and 1 nM, 5 nM and 1 nM for assays for cIAP-1 BIR3 and cIAP-2 BIR3, respectively. Negative controls containing protein/probe complex only (equivalent to 0% inhibition), and positive controls containing only free probes (equivalent to 100% inhibition), were included in each assay plate. FP values were measured as described above. $IC_{50}$ values were determined by nonlinear regression fitting of the competition curves. The $K_i$ values of competitive inhibitors were calculated using the derived equation described previously, based upon the measured $IC_{50}$ values, the $K_d$ values of the probe to different proteins, and the concentrations of the proteins and probes in the competitive assays.

The FP-based assay for XIAP linker-BIR2-BIR3 protein was performed with the same procedures. In this assay, a bivalent fluorescently tagged peptidic Smac mimetic (Smac-1F) was used as the fluorescent probe whose $K_d$ value to XIAP linker-BIR2-BIR3 was determined similarly through the saturation experiments. 0.01% of Triton X-100 was added in the assay buffer to achieve stable fluorescence and polarization value of the dimeric fluorescent probe. Final protein and probe concentrations utilized in the competitive assay were 3 nM and 1 nM, respectively.

| Ex-am-ple | Structures | Binding Affinities IC50 (nM) | | |
|---|---|---|---|---|
| | | XIAP Protein | cIAP1 Protein | cIAP2 Protein |
| 1 | 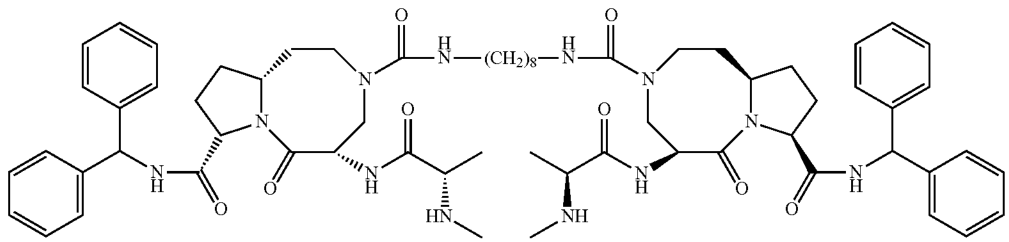 | <10 | <300 | <300 |
| 2 | 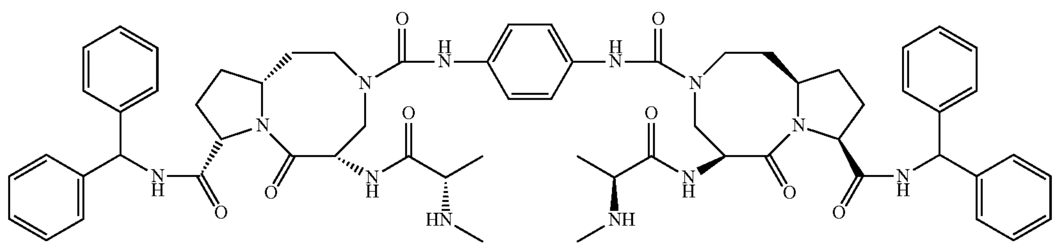 | <10 | <100 | <100 |
| 3 | 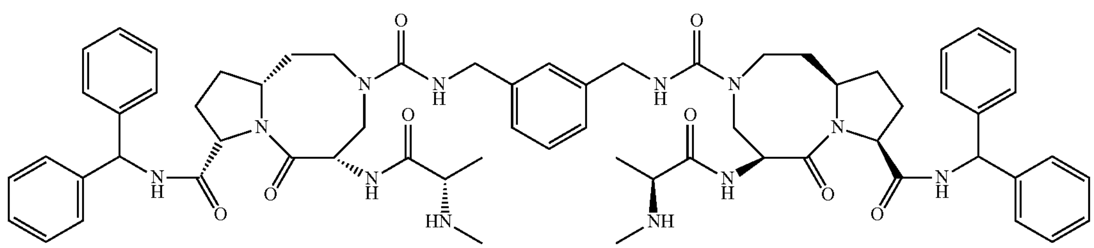 | <10 | <100 | <100 |

| Example | Structures | Binding Affinities IC50 (nM) | | |
|---|---|---|---|---|
| | | XIAP Protein | cIAP1 Protein | cIAP2 Protein |
| 4 | 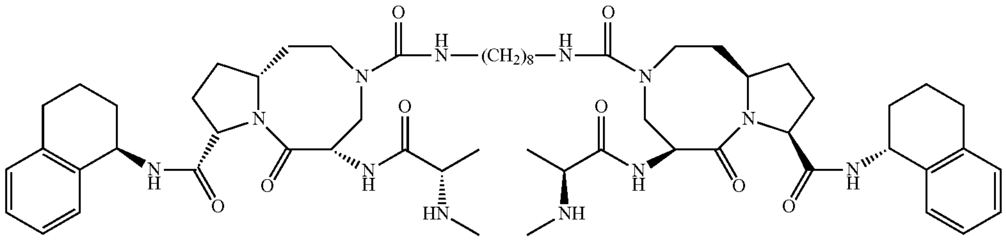 | <10 | <100 | <100 |
| 5 | 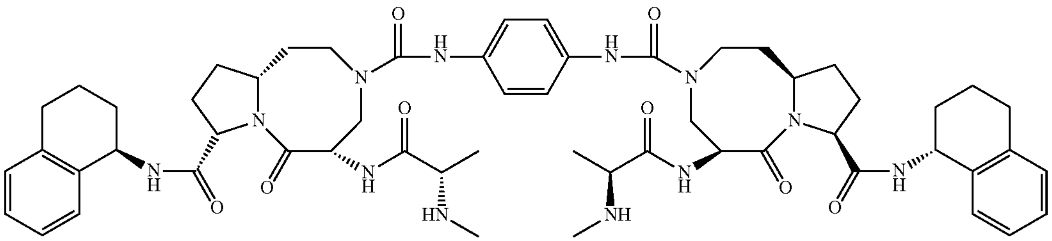 | <10 | <100 | <100 |
| 6 | 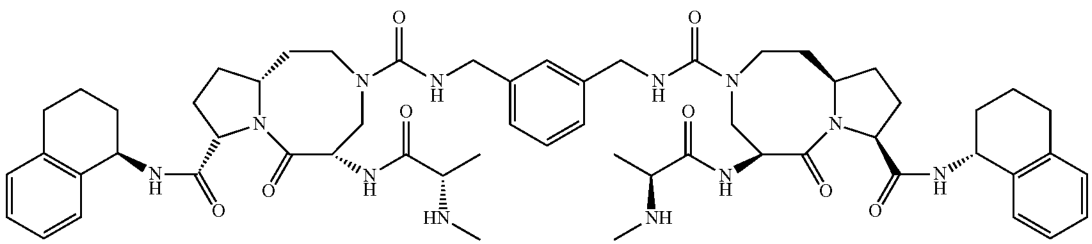 | <10 | <100 | <100 |
| 7 | 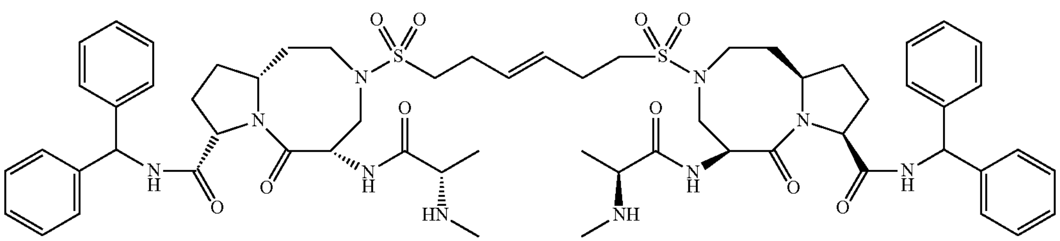 | <10 | <300 | <300 |

-continued

| Example | Structures | Binding Affinities IC50 (nM) | | |
|---|---|---|---|---|
| | | XIAP Protein | cIAP1 Protein | cIAP2 Protein |
| 8 | 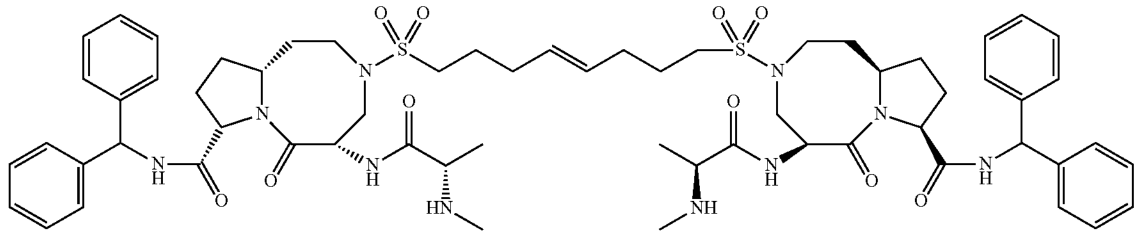 | <10 | <100 | <100 |
| 9 | 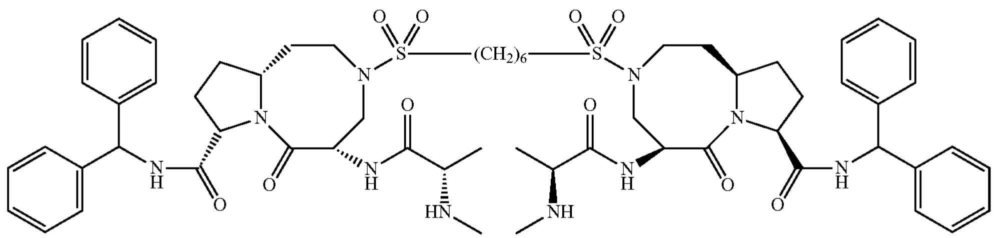 | <10 | <100 | <100 |
| 10 | 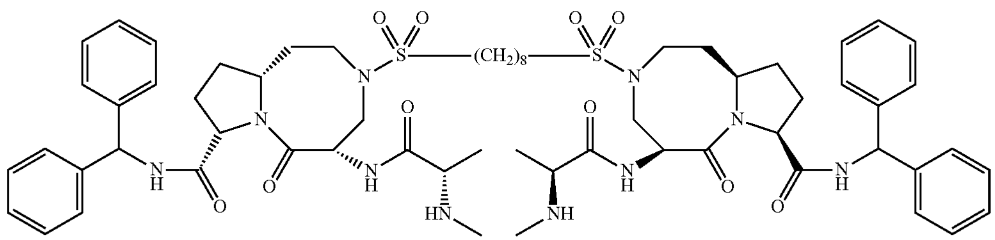 | <10 | <100 | <100 |
| 11 | 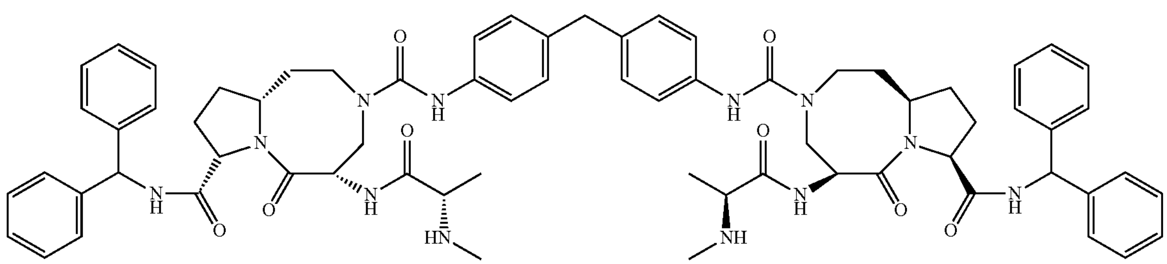 | <10 | <100 | <100 |

| Example | Structures | Binding Affinities IC50 (nM) | | |
|---|---|---|---|---|
| | | XIAP Protein | cIAP1 Protein | cIAP2 Protein |
| 12 | 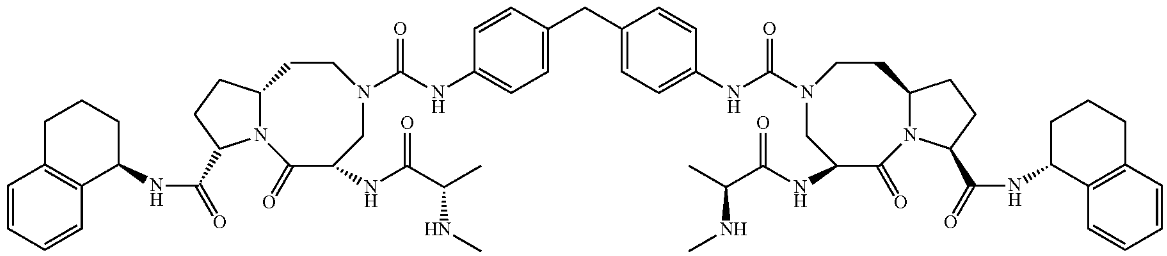 | <10 | <100 | <100 |
| 13 | 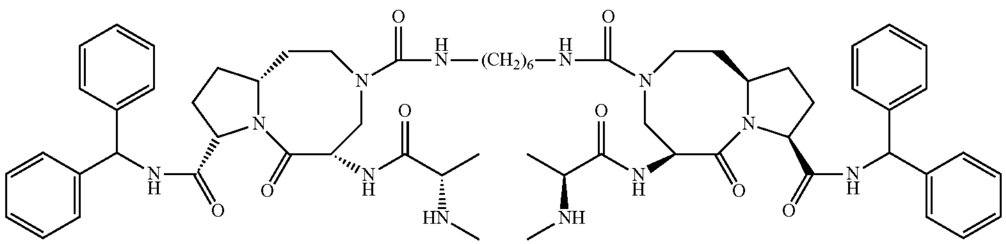 | <30 | <300 | <300 |
| 14 | 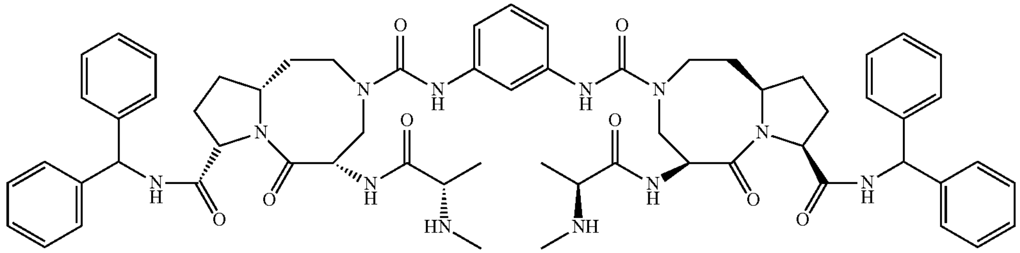 | <30 | <300 | <300 |

| Example | Structures | Binding Affinities IC50 (nM) | | |
|---|---|---|---|---|
| | | XIAP Protein | cIAP1 Protein | cIAP2 Protein |
| 15 | 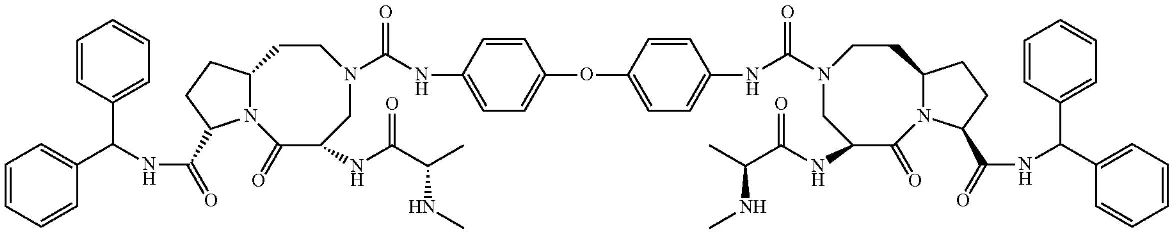 | <30 | <300 | <300 |
| 16 | 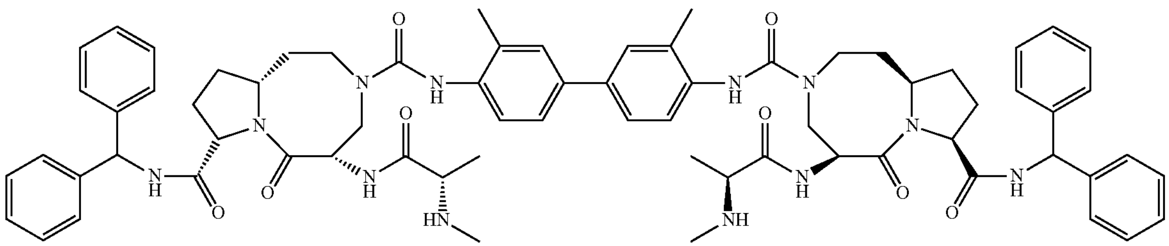 | <100 | <300 | <300 |
| 17 | 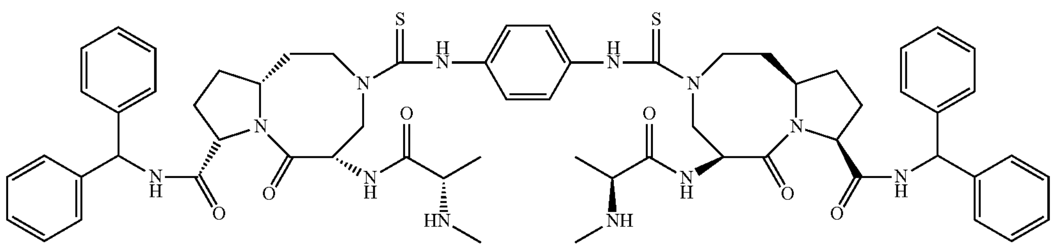 | <30 | <300 | <300 |
| 18 | 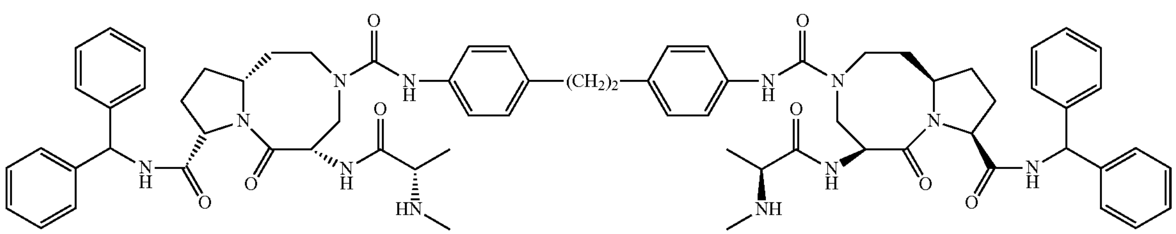 | <30 | <300 | <300 |

-continued

| Example | Structures | Binding Affinities IC50 (nM) | | |
|---|---|---|---|---|
| | | XIAP Protein | cIAP1 Protein | cIAP2 Protein |
| 19 | 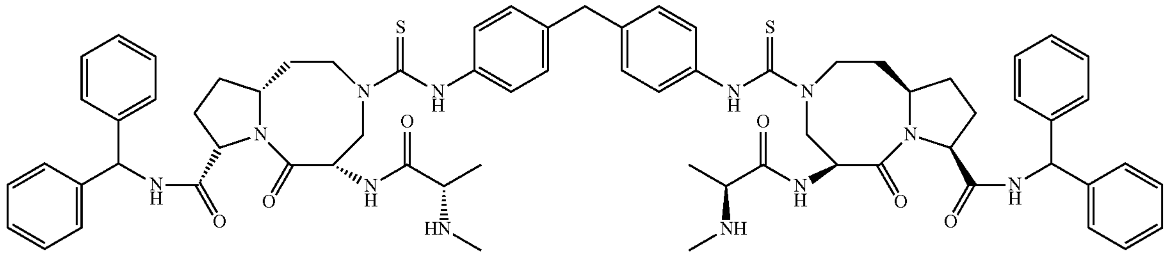 | <30 | <300 | <300 |
| 20 | 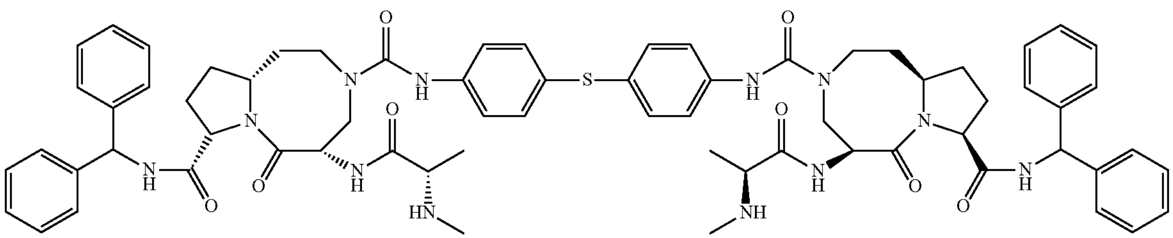 | <30 | <100 | <300 |
| 21 | 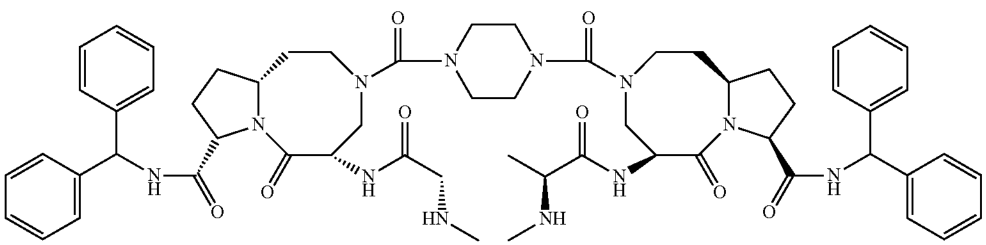 | <30 | <300 | <300 |
| 22 | 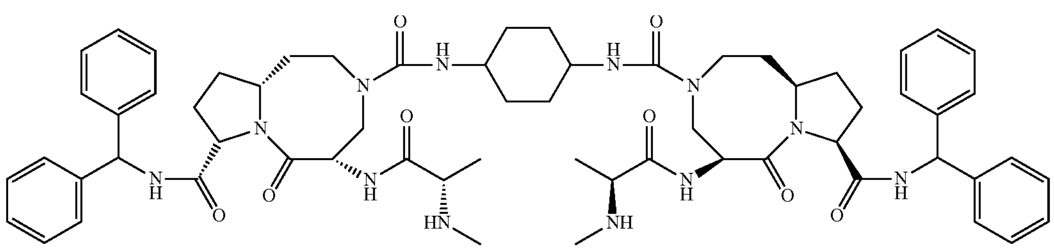 | <30 | <300 | <300 |

-continued

| Example | Structures | Binding Affinities IC50 (nM) | | |
|---|---|---|---|---|
| | | XIAP Protein | cIAP1 Protein | cIAP2 Protein |
| 23 | 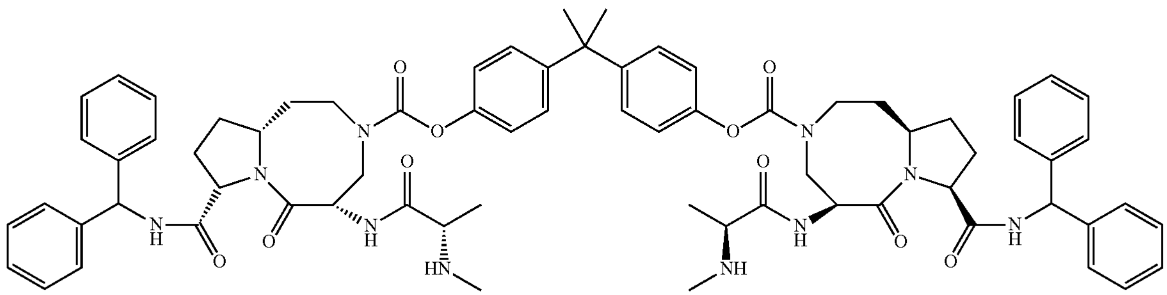 | <30 | <300 | <300 |
| 24 | 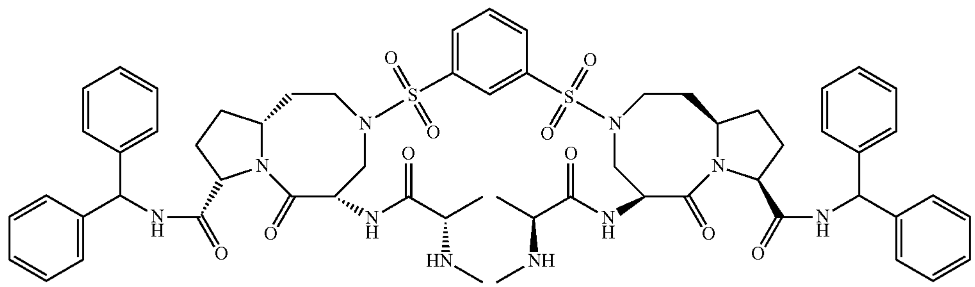 | <30 | <300 | <300 |
| 25 | 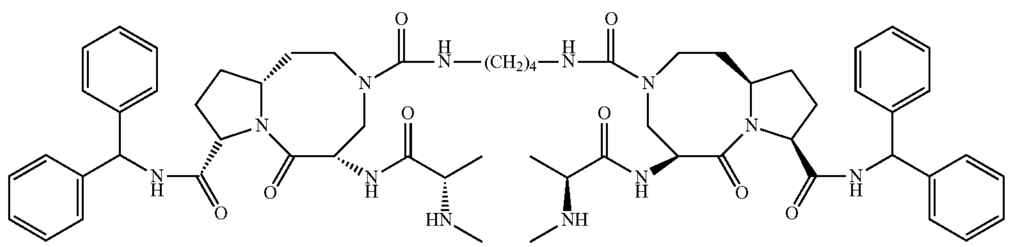 | <30 | <300 | <300 |

| Example | Structures | Binding Affinities IC50 (nM) | | |
|---|---|---|---|---|
| | | XIAP Protein | cIAP1 Protein | cIAP2 Protein |
| 26 | 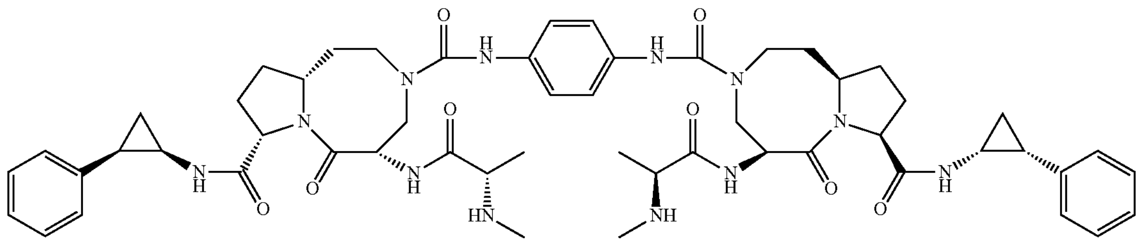 [SMILES: CN[C@@H](C)C(=O)N[C@H]1CN(C(=O)Nc2ccc(NC(=O)N3CC[C@H]4CC[C@@H](C(=O)N[C@@H]5C[C@@H]5c5ccccc5)N4C(=O)[C@@H](NC(=O)[C@H](C)NC)C3)cc2)CC[C@H]2CC[C@@H](C(=O)N[C@@H]3C[C@@H]3c3ccccc3)N2C1=O] | <1000 | <1000 | <1000 |
| 27 | 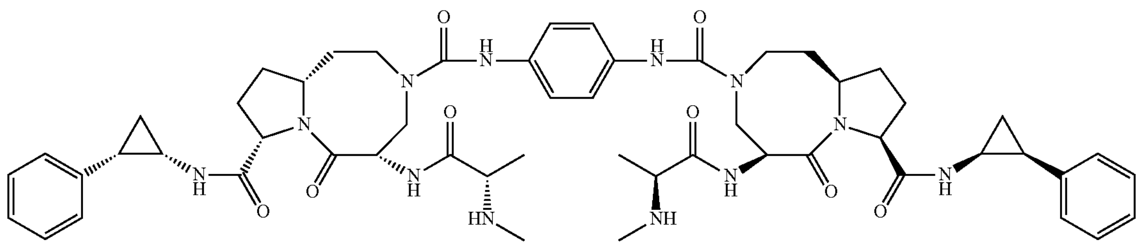 [SMILES: CN[C@@H](C)C(=O)N[C@H]1CN(C(=O)Nc2ccc(NC(=O)N3CC[C@H]4CC[C@@H](C(=O)N[C@H]5C[C@H]5c5ccccc5)N4C(=O)[C@@H](NC(=O)[C@H](C)NC)C3)cc2)CC[C@H]2CC[C@@H](C(=O)N[C@H]3C[C@H]3c3ccccc3)N2C1=O] | <1000 | <1000 | <1000 |
| 28 | 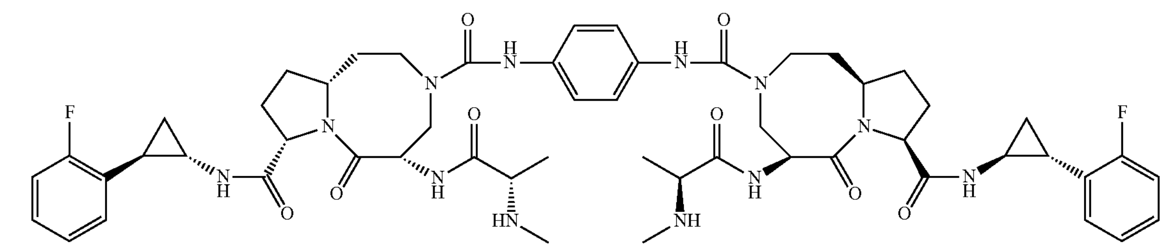 | <1000 | <1000 | <1000 |
| 29 | 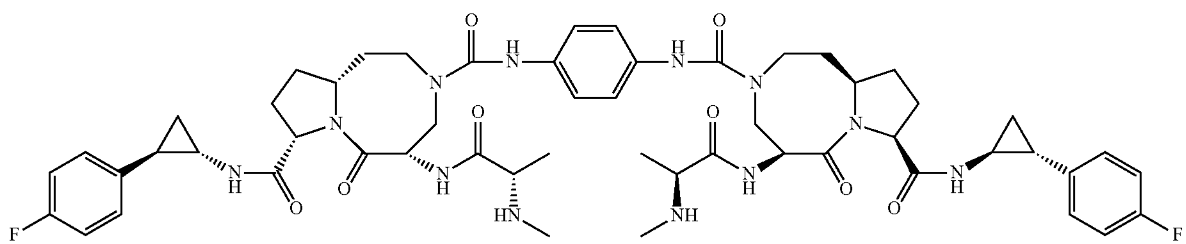 [SMILES: CN[C@@H](C)C(=O)N[C@H]1CN(C(=O)Nc2ccc(NC(=O)N3CC[C@H]4CC[C@@H](C(=O)N[C@H]5C[C@@H]5c5ccc(F)cc5)N4C(=O)[C@@H](NC(=O)[C@H](C)NC)C3)cc2)CC[C@H]2CC[C@@H](C(=O)N[C@H]3C[C@@H]3c3ccc(F)cc3)N2C1=O] | <1000 | <1000 | <1000 |

| Example | Structures | Binding Affinities IC50 (nM) | | |
|---|---|---|---|---|
| | | XIAP Protein | cIAP1 Protein | cIAP2 Protein |
| 30 | 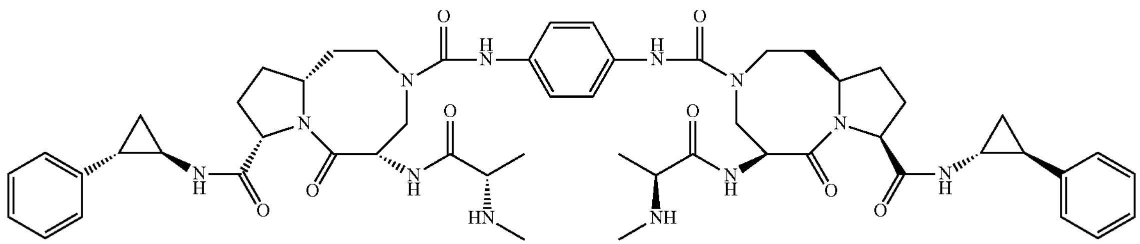 [SMILES: CN[C@@H](C)C(=O)N[C@H]1CN(C(=O)Nc2ccc(NC(=O)N3CC[C@H]4CC[C@@H](C(=O)N[C@@H]5C[C@H]5c5ccccc5)N4C(=O)[C@@H](NC(=O)[C@H](C)NC)C3)cc2)CC[C@H]2CC[C@@H](C(=O)N[C@@H]3C[C@H]3c3ccccc3)N2C1=O] | <3000 | <3000 | <3000 |
| 31 | 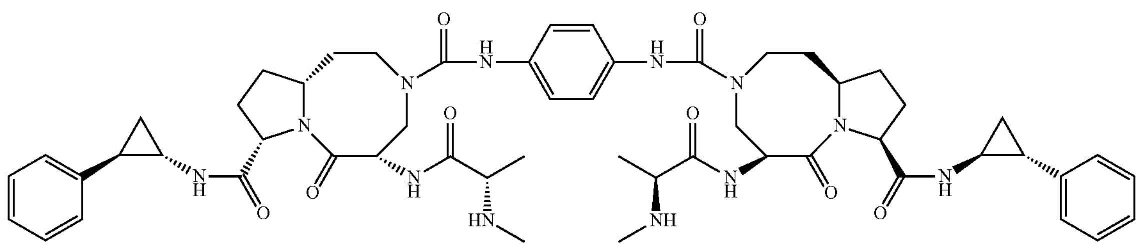 [SMILES: CN[C@@H](C)C(=O)N[C@H]1CN(C(=O)Nc2ccc(NC(=O)N3CC[C@H]4CC[C@@H](C(=O)N[C@H]5C[C@@H]5c5ccccc5)N4C(=O)[C@@H](NC(=O)[C@H](C)NC)C3)cc2)CC[C@H]2CC[C@@H](C(=O)N[C@H]3C[C@@H]3c3ccccc3)N2C1=O] | <1000 | <1000 | <1000 |
| 32 | 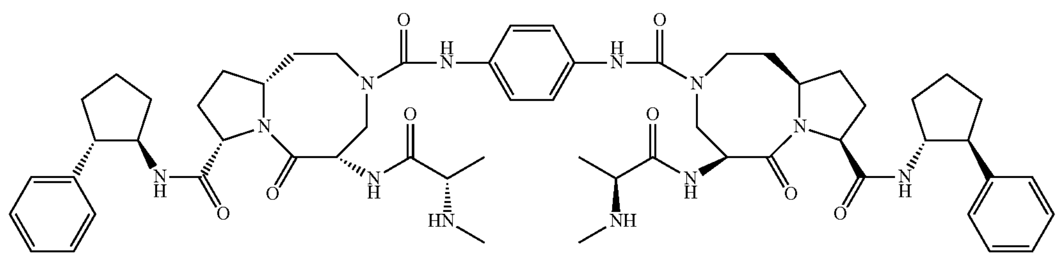 [SMILES: CN[C@@H](C)C(=O)N[C@H]1CN(C(=O)Nc2ccc(NC(=O)N3CC[C@H]4CC[C@@H](C(=O)N[C@@H]5CCC[C@H]5c5ccccc5)N4C(=O)[C@@H](NC(=O)[C@H](C)NC)C3)cc2)CC[C@H]2CC[C@@H](C(=O)N[C@@H]3CCC[C@H]3c3ccccc3)N2C1=O] | <3000 | <3000 | <3000 |
| 33 | 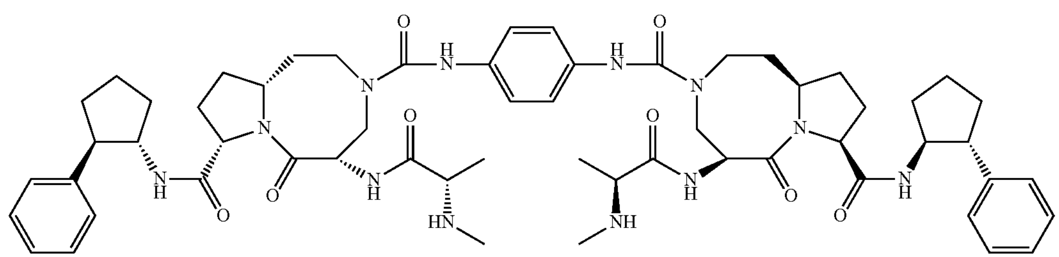 | <3000 | <3000 | <3000 |

-continued

| Example | Structures | Binding Affinities IC50 (nM) | | |
|---|---|---|---|---|
| | | XIAP Protein | cIAP1 Protein | cIAP2 Protein |
| 34 | 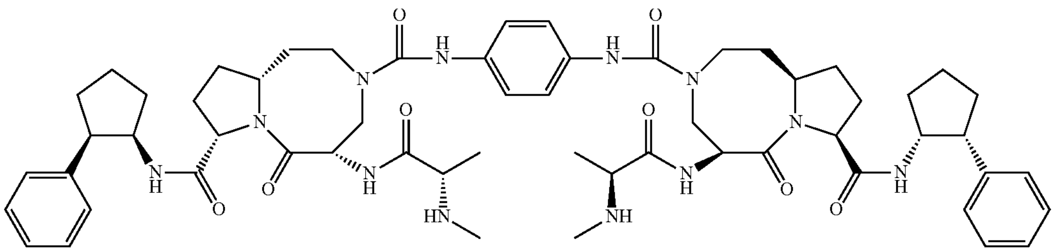 [SMILES: CN[C@@H](C)C(=O)N[C@H]1CN(C(=O)Nc2ccc(NC(=O)N3CC[C@H]4CC[C@@H](C(=O)N[C@@H]5CCC[C@@H]5c5ccccc5)N4C(=O)[C@@H](NC(=O)[C@H](C)NC)C3)cc2)CC[C@H]2CC[C@@H](C(=O)N[C@@H]3CCC[C@@H]3c3ccccc3)N2C1=O] | <1000 | <1000 | <1000 |
| 35 | 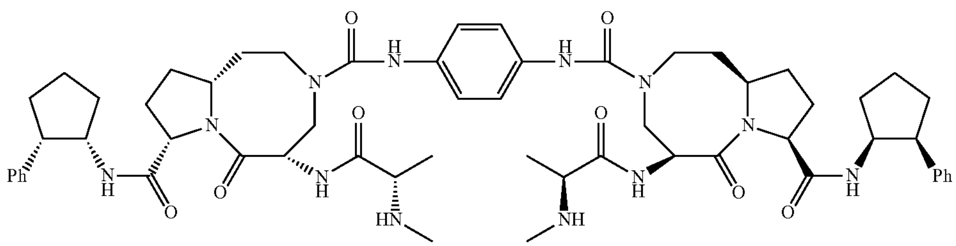 | <1000 | <1000 | <1000 |
| 36 | 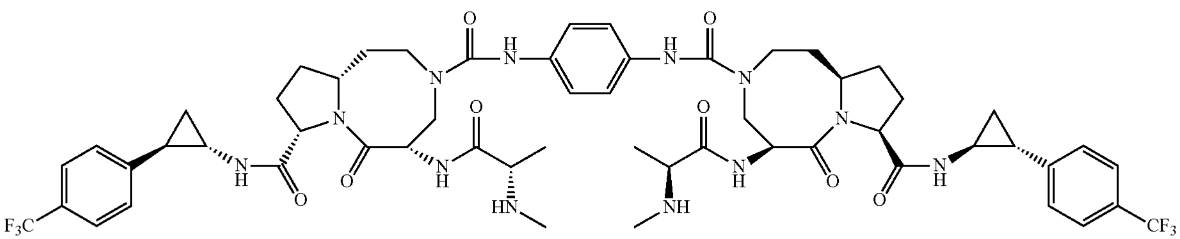 [SMILES: CN[C@@H](C)C(=O)N[C@H]1CN(C(=O)Nc2ccc(NC(=O)N3CC[C@H]4CC[C@@H](C(=O)N[C@H]5C[C@@H]5c5ccc(C(F)(F)F)cc5)N4C(=O)[C@@H](NC(=O)[C@H](C)NC)C3)cc2)CC[C@H]2CC[C@@H](C(=O)N[C@H]3C[C@@H]3c3ccc(C(F)(F)F)cc3)N2C1=O] | <3000 | <3000 | <3000 |
| 37 | 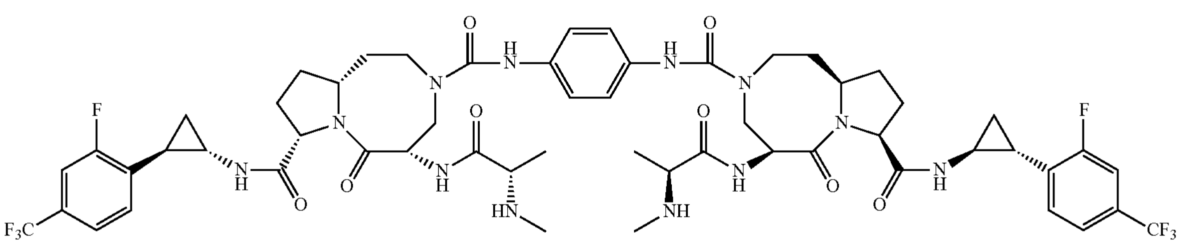 | <3000 | <3000 | <3000 |

-continued

| Example | Structures | Binding Affinities IC50 (nM) | | |
|---|---|---|---|---|
| | | XIAP Protein | cIAP1 Protein | cIAP2 Protein |
| 38 | 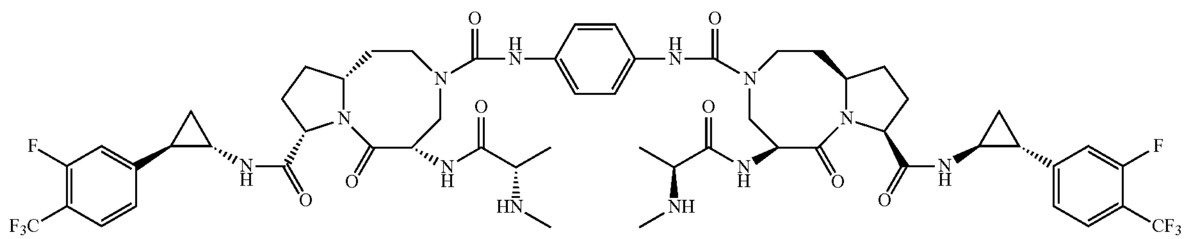 | <3000 | <3000 | <3000 |
| 39 | 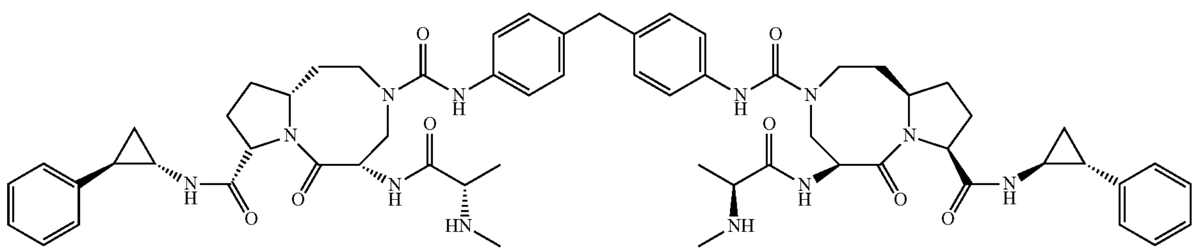 | <1000 | <3000 | <3000 |
| 40 | 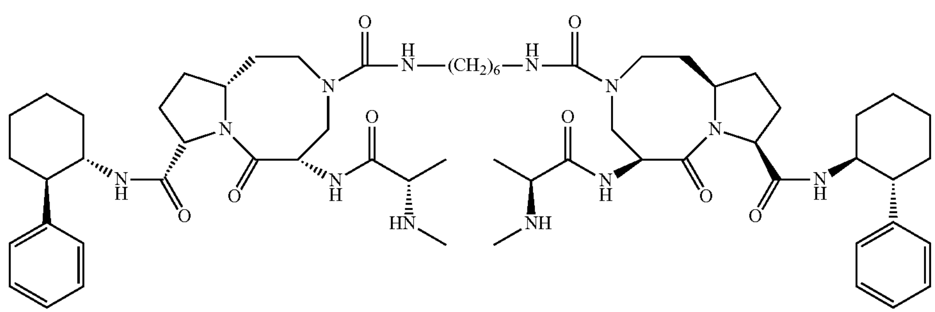 | <3000 | <3000 | <3000 |

-continued

| Example | Structures | Binding Affinities IC50 (nM) | | |
|---|---|---|---|---|
| | | XIAP Protein | cIAP1 Protein | cIAP2 Protein |
| 41 | 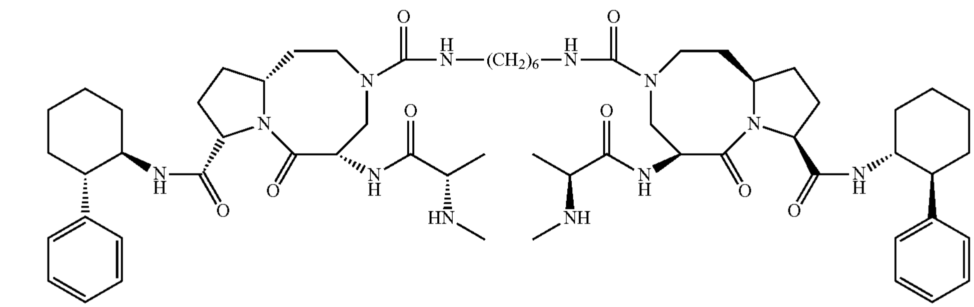 | <5000 | <5000 | <5000 |
| 42 | 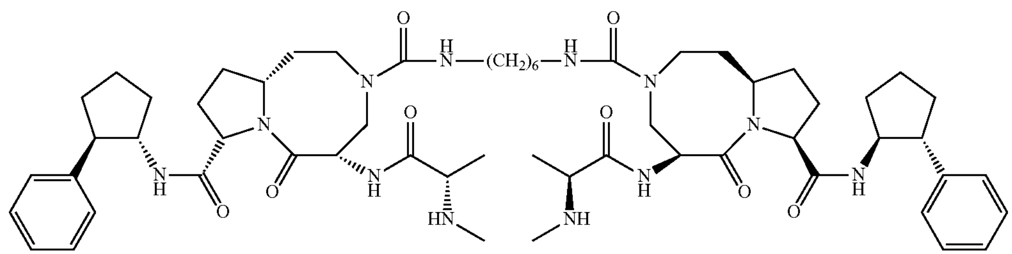 | <1000 | <1000 | <3000 |
| 43 | 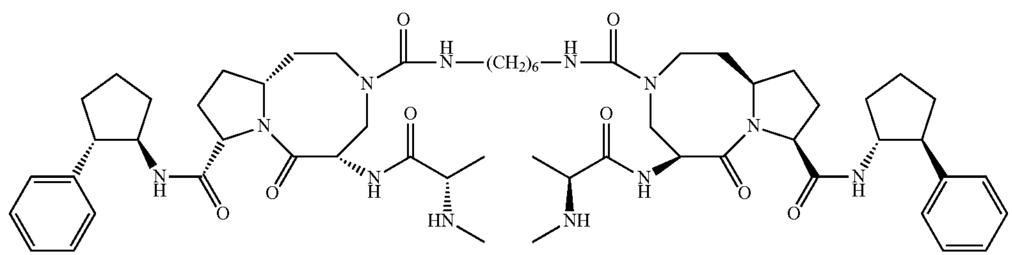 | <3000 | <3000 | <3000 |

-continued

| Example | Structures | Binding Affinities IC50 (nM) | | |
|---|---|---|---|---|
| | | XIAP Protein | cIAP1 Protein | cIAP2 Protein |
| 44 | 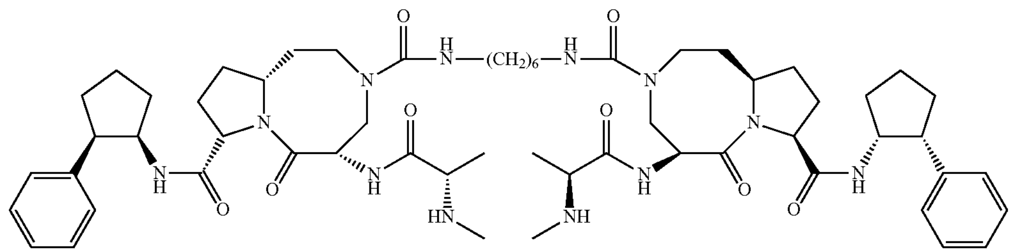 | <1000 | <1000 | <3000 |
| 45 | 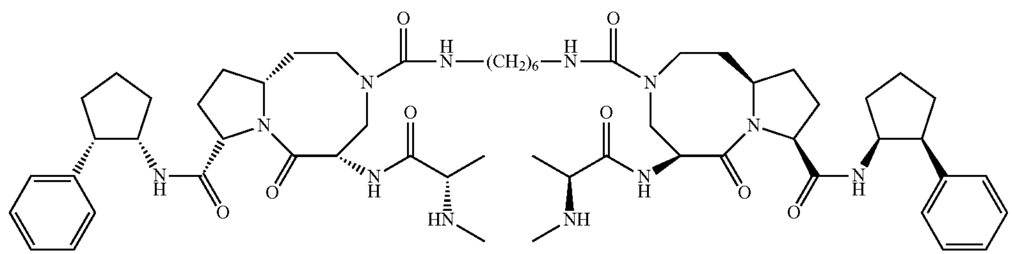 | <1000 | <3000 | <3000 |
| 46 | 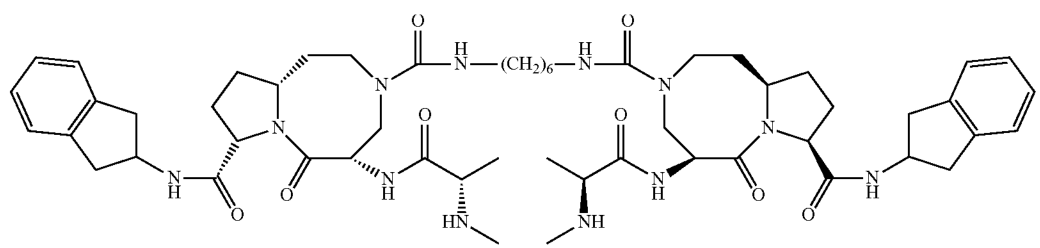 | <1000 | <10000 | <5000 |
| 47 | 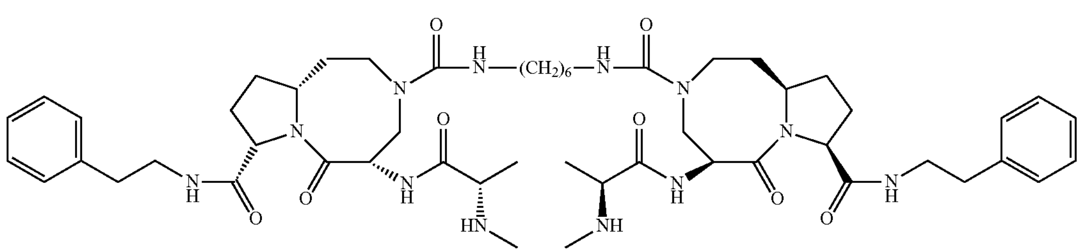 | <1000 | <1000 | <5000 |

-continued

| Example | Structures | Binding Affinities IC50 (nM) | | |
|---|---|---|---|---|
| | | XIAP Protein | cIAP1 Protein | cIAP2 Protein |
| 48 | 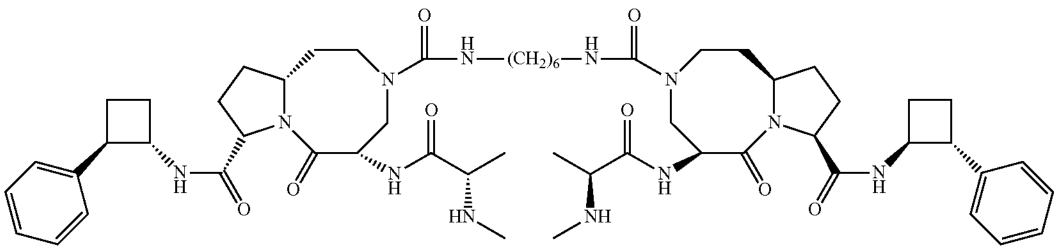 | <1000 | <1000 | <1000 |
| 49 | 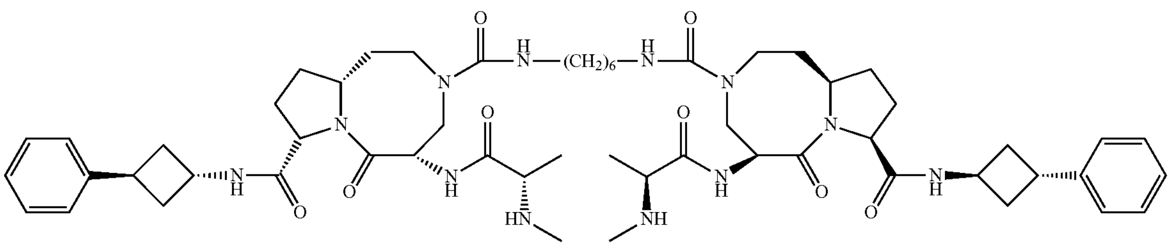 | <1000 | <1000 | <5000 |
| 50 | 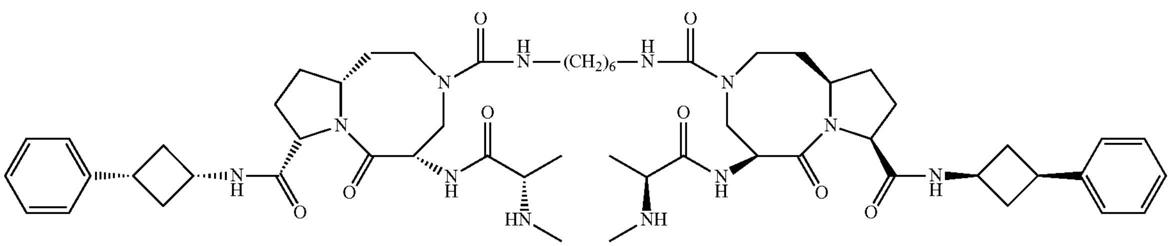 | <1000 | <1000 | <1000 |

Inhibition of Cell Growth in MDA-MB-231
Breast Cancer and SK-OV-3 Ovarian Cancer Cell Line

| Example | Structures | Cell growth Inhibition (IC$_{50}$, nM) | |
|---|---|---|---|
| | | MDA-MB-231 Cancer Cell Line | SK-OV-3 Cancer Cell Line |
| 1 | 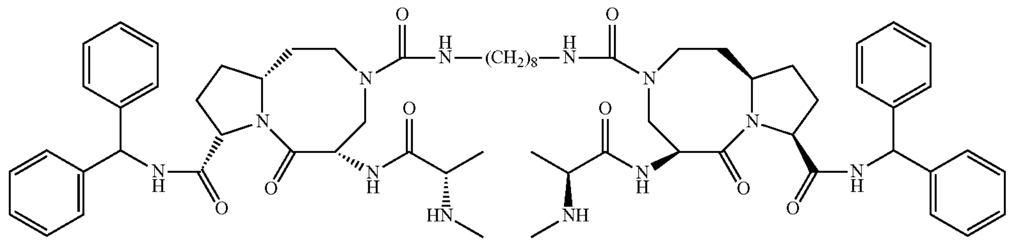 | <100 | <100 |
| 2 | 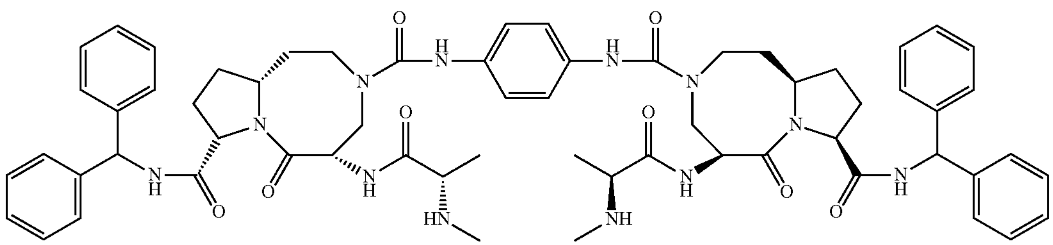 | <100 | <100 |
| 3 | 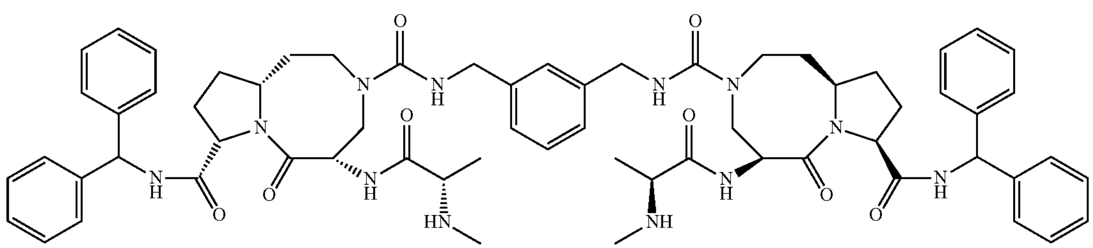 | <100 | <100 |

Inhibition of Cell Growth in MDA-MB-231 Breast Cancer and SK-OV-3 Ovarian Cancer Cell Line

| Example | Structures | Cell growth Inhibition (IC$_{50}$, nM) | |
| --- | --- | --- | --- |
| | | MDA-MB-231 Cancer Cell Line | SK-OV-3 Cancer Cell Line |
| 4 | 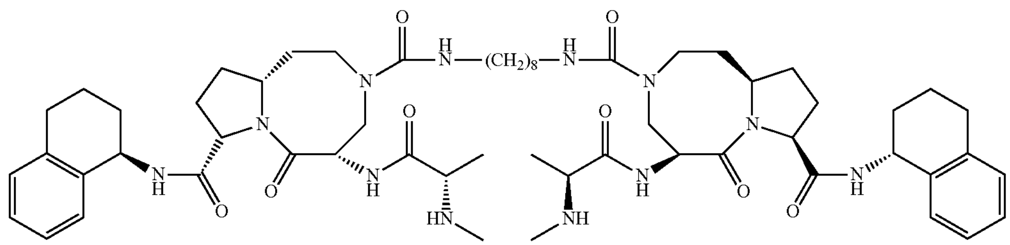 | <100 | <100 |
| 5 | 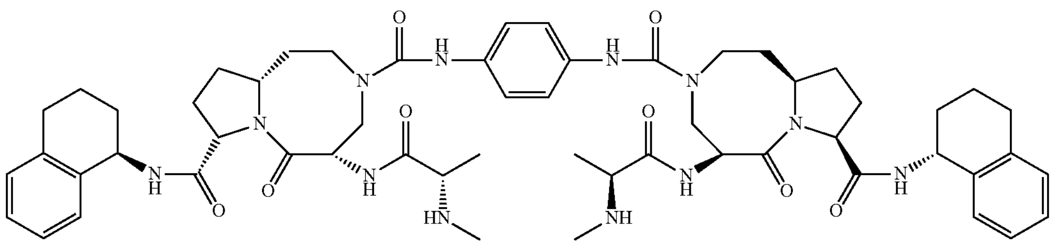 | <100 | <100 |
| 6 | 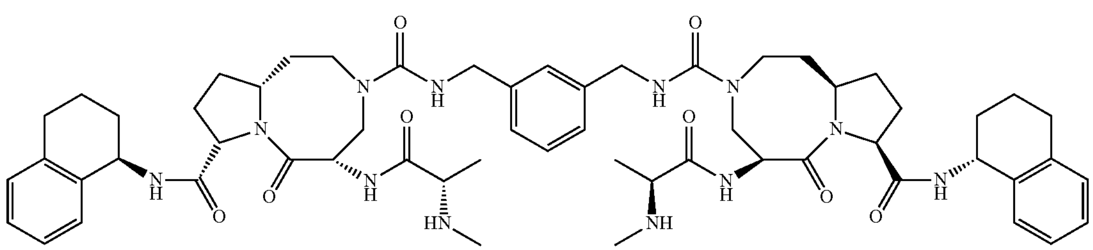 | <100 | <100 |

-continued

Inhibition of Cell Growth in MDA-MB-231
Breast Cancer and SK-OV-3 Ovarian Cancer Cell Line

| | | Cell growth Inhibition (IC$_{50}$, nM) | |
|---|---|---|---|
| Example | Structures | MDA-MB-231 Cancer Cell Line | SK-OV-3 Cancer Cell Line |
| 7 | | <1000 | <1000 |
| 8 | | <1000 | <1000 |
| 9 | | <1000 | <1000 |

-continued

Inhibition of Cell Growth in MDA-MB-231
Breast Cancer and SK-OV-3 Ovarian Cancer Cell Line

| Example | Structures | Cell growth Inhibition (IC$_{50}$, nM) | |
|---|---|---|---|
| | | MDA-MB-231 Cancer Cell Line | SK-OV-3 Cancer Cell Line |
| 10 | 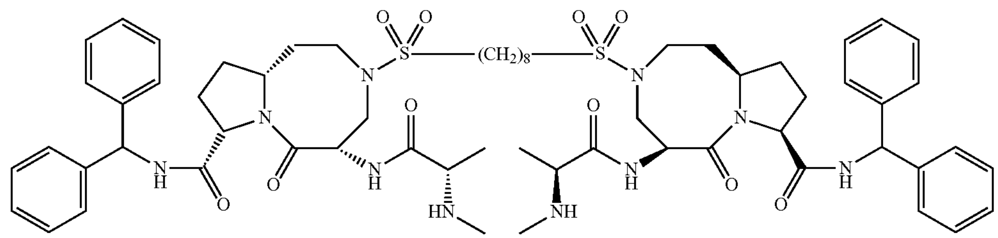 | <1000 | <1000 |
| 11 | 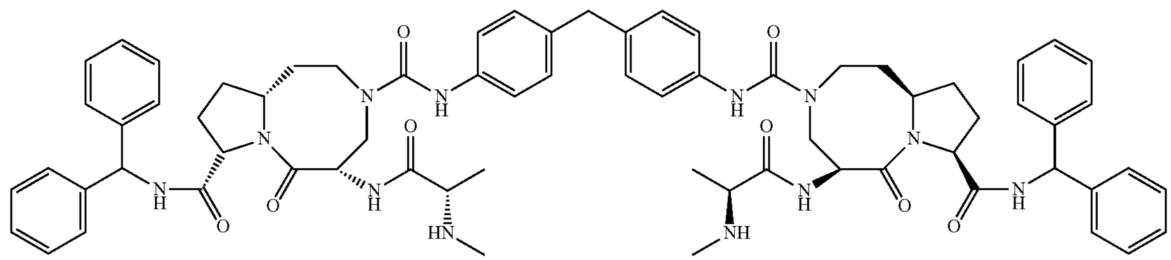 | <100 | <100 |
| 12 | 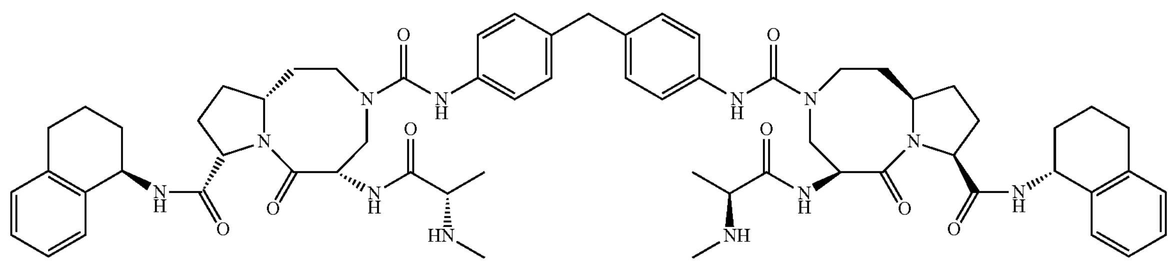 | <100 | <100 |

-continued

Inhibition of Cell Growth in MDA-MB-231
Breast Cancer and SK-OV-3 Ovarian Cancer Cell Line

| Example | Structures | Cell growth Inhibition (IC$_{50}$, nM) | |
|---|---|---|---|
| | | MDA-MB-231 Cancer Cell Line | SK-OV-3 Cancer Cell Line |
| 13 | | <100 | <100 |
| 14 | | <1000 | <1000 |
| 15 | | <1000 | <1000 |

Inhibition of Cell Growth in MDA-MB-231 Breast Cancer and SK-OV-3 Ovarian Cancer Cell Line

| Example | Structures | Cell growth Inhibition (IC$_{50}$, nM) | |
|---|---|---|---|
| | | MDA-MB-231 Cancer Cell Line | SK-OV-3 Cancer Cell Line |
| 16 | 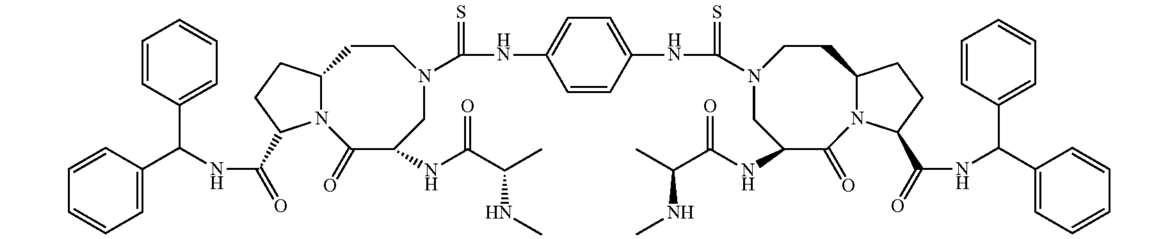 | <100 | Not tested |
| 17 | 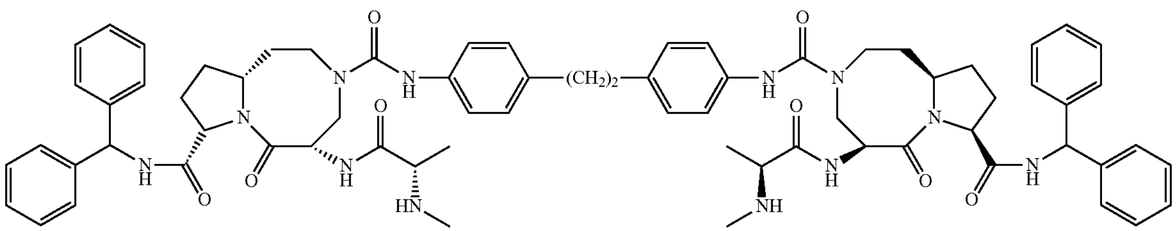 | <100 | Not tested |
| 18 | 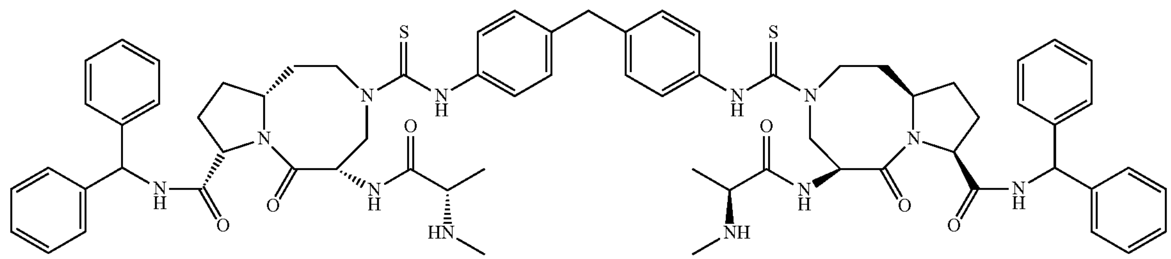 | <100 | Not tested |

-continued

Inhibition of Cell Growth in MDA-MB-231
Breast Cancer and SK-OV-3 Ovarian Cancer Cell Line

| Example | Structures | Cell growth Inhibition (IC$_{50}$, nM) | |
| --- | --- | --- | --- |
| | | MDA-MB-231 Cancer Cell Line | SK-OV-3 Cancer Cell Line |
| 19 | | <1000 | <1000 |
| 20 | | <10,000 | <10,000 |
| 21 | | <1000 | <1000 |

-continued

Inhibition of Cell Growth in MDA-MB-231
Breast Cancer and SK-OV-3 Ovarian Cancer Cell Line

| Example | Structures | Cell growth Inhibition (IC$_{50}$, nM) | |
|---|---|---|---|
| | | MDA-MB-231 Cancer Cell Line | SK-OV-3 Cancer Cell Line |
| 22 | | <100 | <1000 |
| 23 | | <100 | <100 |
| 24 | | <100 | <100 |

Inhibition of Cell Growth in MDA-MB-231
Breast Cancer and SK-OV-3 Ovarian Cancer Cell Line

| Example | Structures | Cell growth Inhibition (IC$_{50}$, nM) | |
|---|---|---|---|
| | | MDA-MB-231 Cancer Cell Line | SK-OV-3 Cancer Cell Line |
| 25 | 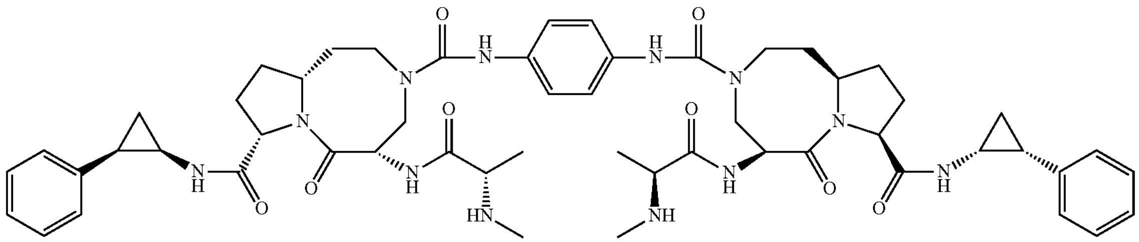 | <1000 | <1000 |
| 26 | 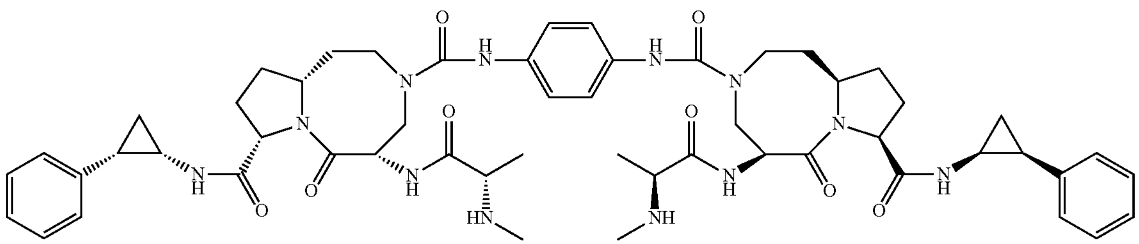 | <1000 | <1000 |
| 27 | 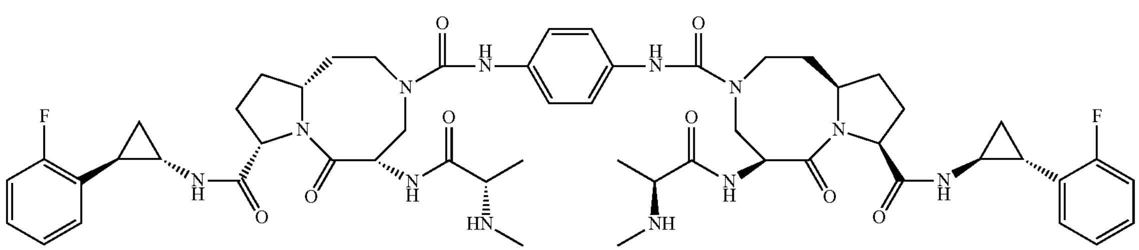 | <5000 | <5000 |

-continued

Inhibition of Cell Growth in MDA-MB-231
Breast Cancer and SK-OV-3 Ovarian Cancer Cell Line

| Example | Structures | Cell growth Inhibition (IC$_{50}$, nM) | |
|---|---|---|---|
| | | MDA-MB-231 Cancer Cell Line | SK-OV-3 Cancer Cell Line |
| 28 | | Not tested | Not tested |
| 29 | | <5000 | <5000 |
| 30 | | <10,000 | <10,000 |

-continued

Inhibition of Cell Growth in MDA-MB-231
Breast Cancer and SK-OV-3 Ovarian Cancer Cell Line

| Example | Structures | Cell growth Inhibition (IC$_{50}$, nM) | |
|---|---|---|---|
| | | MDA-MB-231 Cancer Cell Line | SK-OV-3 Cancer Cell Line |
| 31 | | <1000 | <1000 |
| 32 | | <1000 | <1000 |
| 33 | | <1000 | <1000 |

Inhibition of Cell Growth in MDA-MB-231 Breast Cancer and SK-OV-3 Ovarian Cancer Cell Line

| Example | Structures | Cell growth Inhibition (IC$_{50}$, nM) | |
|---|---|---|---|
| | | MDA-MB-231 Cancer Cell Line | SK-OV-3 Cancer Cell Line |
| 34 | | <100 | <100 |
| 35 | | <10,000 | <10,000 |
| 36 | | <10,000 | <10,000 |

-continued

Inhibition of Cell Growth in MDA-MB-231
Breast Cancer and SK-OV-3 Ovarian Cancer Cell Line

| Example | Structures | Cell growth Inhibition (IC$_{50}$, nM) | |
|---|---|---|---|
| | | MDA-MB-231 Cancer Cell Line | SK-OV-3 Cancer Cell Line |
| 37 | | <10,000 | <10,000 |
| 38 | | <10,000 | <10,000 |
| 39 | | <1000 | <1000 |

Inhibition of Cell Growth in MDA-MB-231 Breast Cancer and SK-OV-3 Ovarian Cancer Cell Line

| Example | Structures | Cell growth Inhibition (IC$_{50}$, nM) | |
| --- | --- | --- | --- |
| | | MDA-MB-231 Cancer Cell Line | SK-OV-3 Cancer Cell Line |
| 40 | | <10,000 | <10,000 |
| 41 | | <1000 | <1000 |
| 42 | | <1000 | <1000 |

-continued

Inhibition of Cell Growth in MDA-MB-231 Breast Cancer and SK-OV-3 Ovarian Cancer Cell Line

| Example | Structures | Cell growth Inhibition (IC$_{50}$, nM) | |
|---|---|---|---|
| | | MDA-MB-231 Cancer Cell Line | SK-OV-3 Cancer Cell Line |
| 43 | | <1000 | <1000 |
| 44 | | <1000 | <1000 |
| 45 | | <1000 | <1000 |

-continued

Inhibition of Cell Growth in MDA-MB-231
Breast Cancer and SK-OV-3 Ovarian Cancer Cell Line

| Example | Structures | Cell growth Inhibition (IC$_{50}$, nM) | |
|---|---|---|---|
| | | MDA-MB-231 Cancer Cell Line | SK-OV-3 Cancer Cell Line |
| 46 | 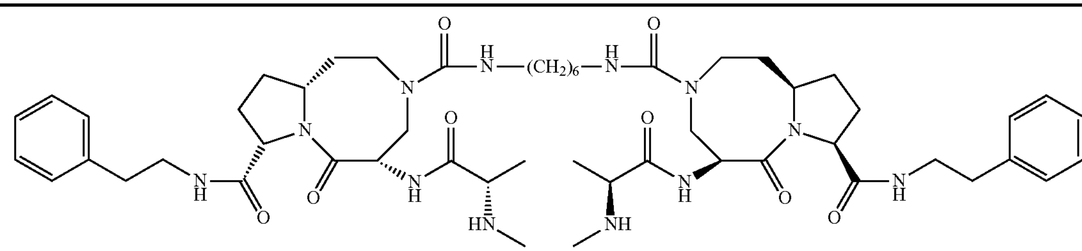 | <1000 | <1000 |
| 47 | 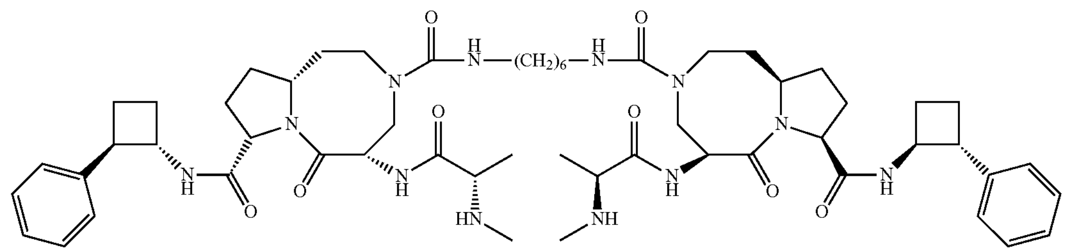 | <1000 | <1000 |
| 48 | 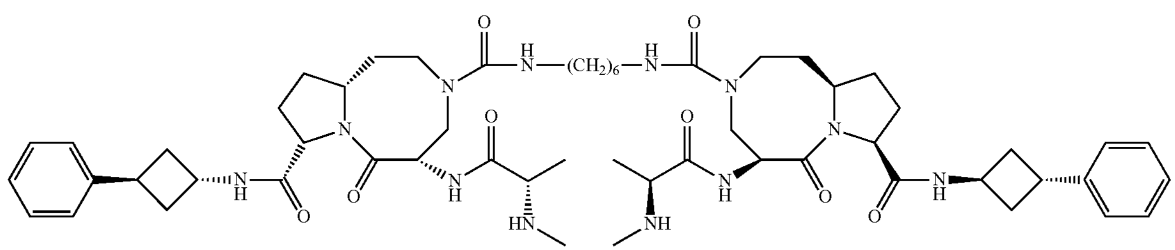 | <10,000 | <10,000 |

FIG. 1 shows the antitumor activity of Example 2 and Example 24 in the MDA-MB-231 xenograft model in nude mice. Treatments started when the tumors reached an average volume of 80 mm$^3$ Example 24 was given intravenously, weekly dose for 4 weeks (qwkx4, iv) at 10 mg/kg. Example 2 was given weekly dose for 4 weeks (qwkx4, iv) at 3 mg/kg. Control treatment was given vehicle control. Each group has 8-10 mice and each mouse has one tumor. Tumor regression was achieved for Examples 2 and 24.

REFERENCES (1) D. W. Nicholson, *Nature* 2000, 407, 810-816.
(2) B. A. Ponder, *Nature* 2001, 411, 336-341.
(3) S. W. Lowe et al., *Carcinogenesis* 2000, 21, 485-495.
(4) D. Hanahan et al., *Cell* 2000, 100, 57-70.
(5) G. S. Salvesen et al., *Nat. Rev. Mol. Cell. Biol.* 2002, 3, 401-410.
(6) Q. L. Deveraux et al., *Genes Dev.* 1999, 13, 239-252.
(7) S. M. Srinivasula et al., *Mol. Cell.* 2008, 30, 123-135.
(8) M. Gyrd-Hansen et al., *Nat. Rev. Cancer,* 2010, 10, 561-574.
(9) I. Tamm et al., *Clin Cancer Res.* 2000, 6, 1796-1803.
(10) D. Vucic et al., *Clin Cancer Res.* 2007, 13, 5995-6000.
(11) A. M. Hunter et al., *Apoptosis* 2007, 12, 1543-1568.
(12) E. C. LaCasse et al., *Oncogene* 2008, 27, 6252-6275.
(13) S. Fulda, *Expert Rev Anticancer Ther.* 2007, 7, 1255-64.
(14) C. Du et al., *Cell* 2000, 102, 33-42.
(15) A. M. Verhagen et al., *Cell* 2000, 102, 43-53.
(16) G. Wu et al., *Nature* 2000, 408, 1008-1012.
(17) Z. Liu et al., *Nature* 2000, 408, 1004-1008.
(18) E. N. Shiozaki et al., *Trends Biochem. Sci.* 2004, 29, 486-494.
(19) T. Samuel et al., *J. Biol. Chem.* 2006, 281, 1080-1090.
(20) Q. Yang et al., *J Biol. Chem.* 2004, 279, 16963-16970.
(21) S. Wang, *Curr Top Microbiol Immunol.* 2011, 348, 89-113.
(22) H. Sun et al., *Acc Chem. Res.* 2008, 41, 1264-1277.
(23) R. Mannhold et al., *Drug Discov Today.* 2010, 15, 210-219.
(24) L. Li et al., *Science* 2004, 305, 1471-1474.
(25) T. K. Oost et al., *J. Med. Chem.* 2004, 47, 4417-4426.
(26) H. Sun et al., *J. Am. Chem. Soc.* 2004, 126, 16686-16697.
(27) H. Sun et al., *J. Med. Chem.* 2004, 47, 4147-4150.
(28) H. Sun et al., *J. Med. Chem.* 2006, 49, 7916-7920.
(29) K. Zobel et al., *ACS Chem. Biol.* 2006, 1, 525-33.
(30) H. Sun et al., *J. Am. Chem. Soc.,* 2007, 129, 15279-15294.
(31) J. Lu et al., *Cancer Res.* 2008, 68, 9384-9393.
(32) H. Sun et al., *J. Med. Chem.,* 2008, 51, 7169-7180.
(33) Y. Peng et al., *J. Med. Chem.,* 2008, 51, 8158-8162.
(34) B. Zhang et al., *J. Med. Chem.,* 2008, 51, 7352-7355.
(35) W. Sun et al., *J. Med. Chem.,* 2009, 52, 593-596.
(36) H. Sun et al., *J. Med. Chem.,* 2010, 53 6361-6367.
(37) Q. Cai et al., *J Med. Chem.* 2011, 54, 2714-2726.
(38) H. Sun et al., *J Med. Chem.* 2011, 54, 3306-3318.

The invention claimed is:

1. A compound having a structure

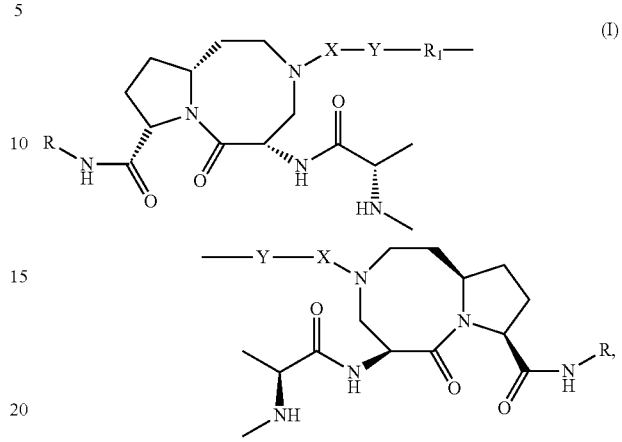

(I)

wherein X is selected from the group consisting of

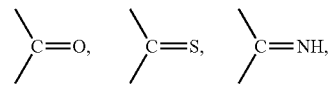

and —SO$_2$—;

Y is selected from the group consisting of —NH—, —O—, and —S—, or Y is null when X is —SO$_2$—;

R is selected from the group consisting of

wherein ring A is a C$_{4-8}$ aliphatic ring

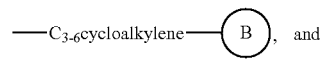, and

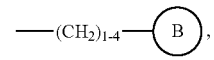, wherein the B ring is phenyl, naphthyl, pyridinyl, pyridazinyl, pyrazinyl, or pyrimidinyl and the B rings are optionally substituted with halo, CF$_3$ or both; and R$_1$ is selected from the group consisting of —(CH$_2$)$_{4-10}$—,

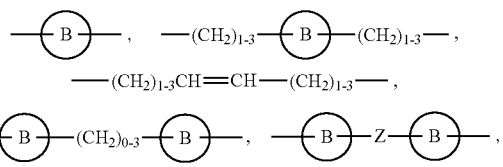

wherein Z is O, S, or NH, and $$-\text{N}\underset{\underset{}{}}{\overset{\overset{}{}}{\diagup}}\text{N}-(\ )_n$$

wherein n is 0, 1, or 2 and the (B)

rings are optionally substituted with $C_{1-3}$ alkyl;
or a pharmaceutically acceptable salt thereof.

2. The compound of claim 1 wherein R is

[structures: —CH(C6H5)2, indane with (—)p substituent]

wherein p is 0 to 4,

[structures: halo-phenyl-cyclopropyl-methyl, CF3-phenyl-cyclopropyl-methyl, C6H5-cyclopentyl-(—)q]

wherein q is 0 to 2, or —(CH$_2$)$_{2-4}$—C$_6$H$_5$.

3. The compound of claim 2 wherein R is

[structures: —CH(C6H5)2, methyl-tetrahydronaphthyl, phenyl-cyclopropyl-methyl, 2-F-phenyl-cyclopropyl-methyl, 3-F-phenyl-cyclopropyl-methyl, 4-F-phenyl-cyclopropyl-methyl, methyl-cyclopentyl-C6H5]

[structures continued: 4-CF3-phenyl-cyclopropyl-methyl, 3-F-4-CF3-phenyl-cyclopropyl-methyl, 4-F-3-CF3-phenyl-cyclopropyl-methyl, methyl-cyclohexyl-C6H5, methyl-indanyl, —(CH$_2$)$_2$—C$_6$H$_5$, phenyl-cyclobutyl-methyl, or phenyl-cyclobutyl-methyl]

4. The compound of claim 1 wherein R$_1$ is

—(CH$_2$)$_{4-8}$—, —(CH$_2$)$_{4-8}$—,

—(CH$_2$)$_{1-2}$—[phenyl]—(CH$_2$)$_{1-2}$—,

—(CH$_2$)$_{1-2}$—CH═CH—(CH$_2$)$_{1-2}$—,

—[phenyl]—(CH$_2$)$_{0-2}$—[phenyl]—,

—[phenyl]—Z—[phenyl]—, or $$-\text{N}\underset{\underset{}{}}{\overset{\overset{}{}}{\diagup}}\text{N}-(\ )_n$$

wherein n is 0 or 1.

5. The compound of claim 4 wherein R$_1$ is

—(CH$_2$)$_4$—, —(CH$_2$)$_6$—, —(CH$_2$)$_8$—,

—CH$_2$—[1,4-phenyl]—CH$_2$—, —CH$_2$—[1,3-phenyl]—CH$_2$—,

—(CH$_2$)$_2$—CH═CH—(CH)$_{1-2}$—,

—[phenyl]—CH$_2$—[phenyl]—,

-continued
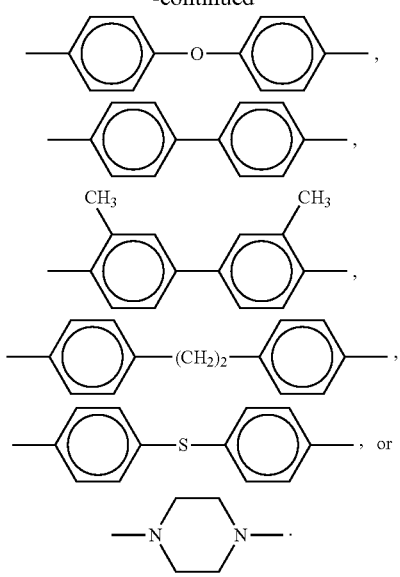
6. The compound of claim 1 wherein X is
and Y is —NH—.
7. The compound of claim 1 wherein X is SO$_2$ and Y is null.
8. The compound of claim 1 wherein X is
and Y is —NH—.
9. The compound of claim 1 wherein X and X' are
and Y is —O—.
10. A compound selected from the group consisting of
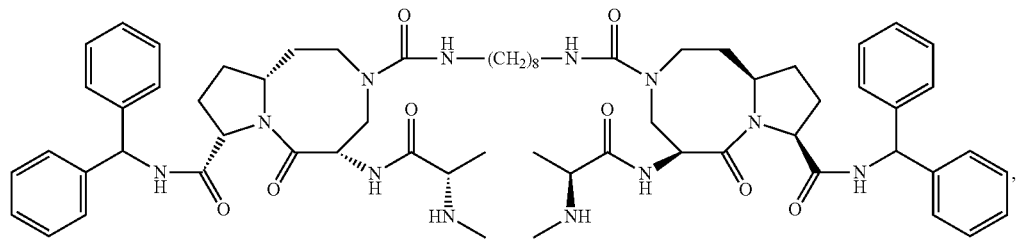
,
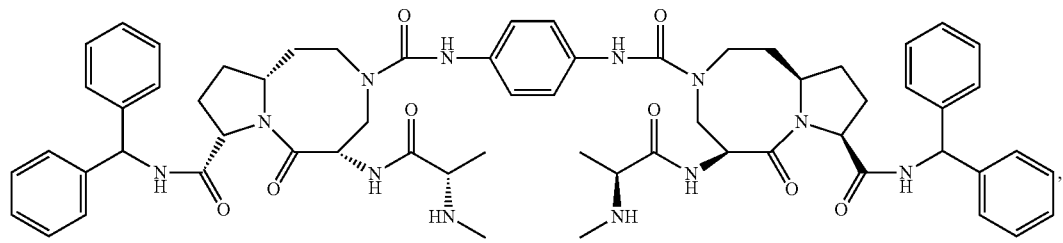
,
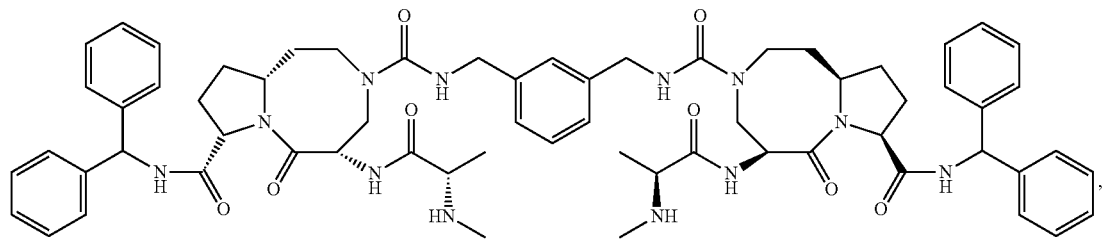
,
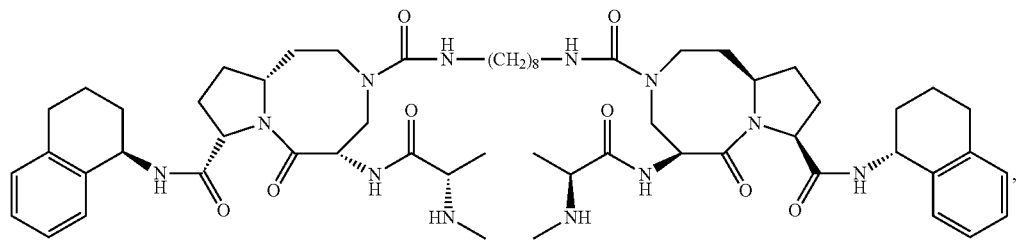
, -continued
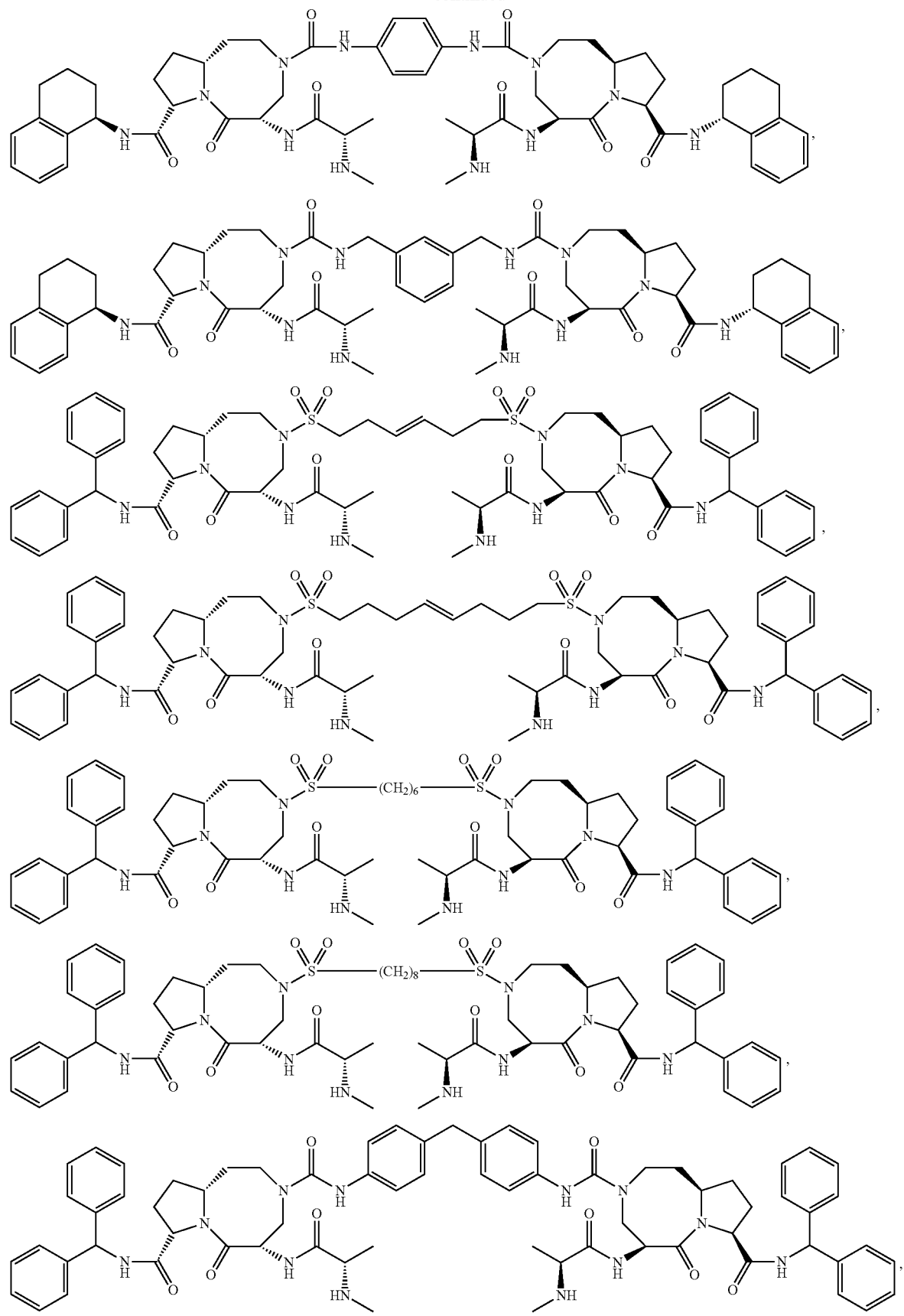

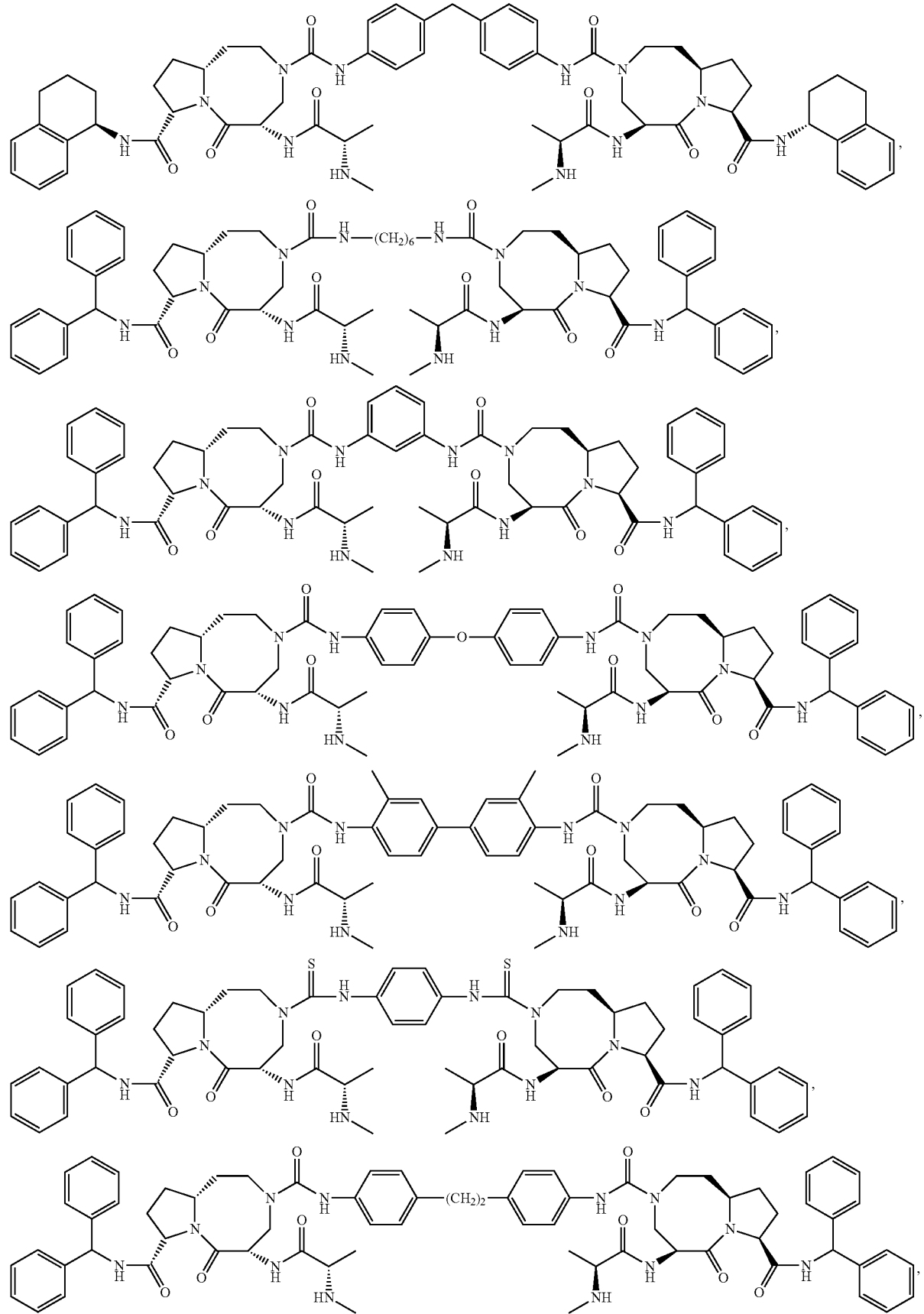

-continued
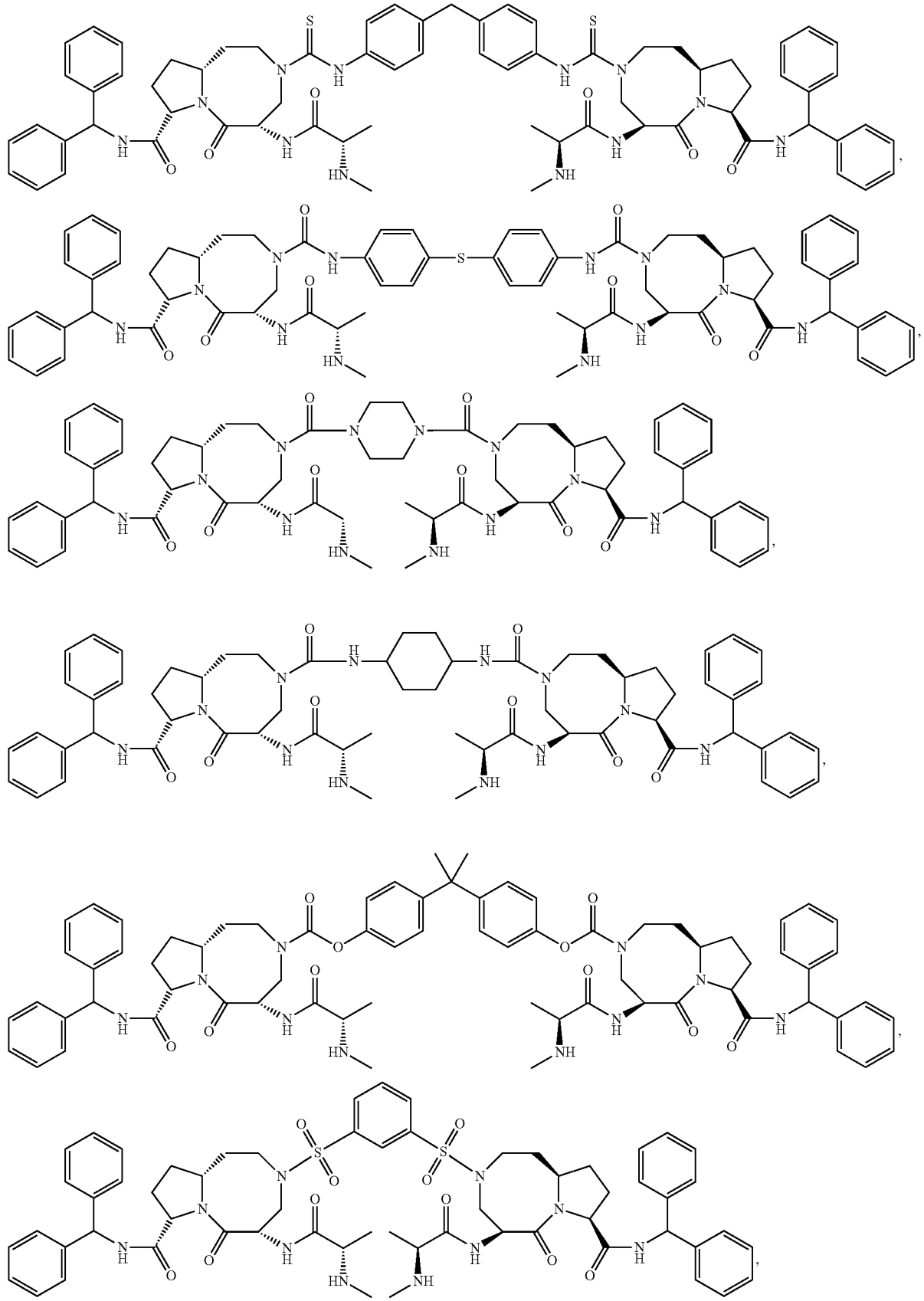

-continued
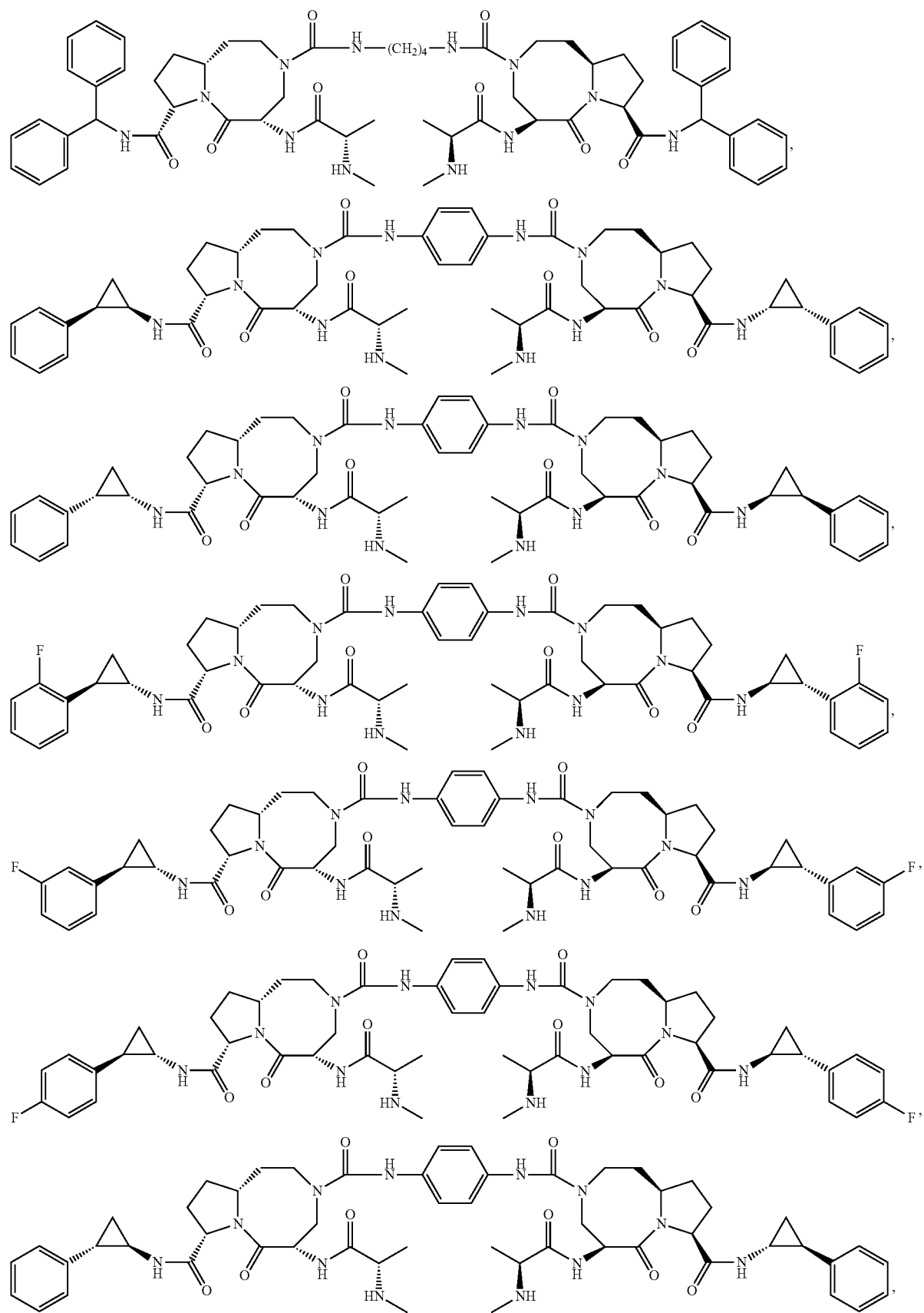

-continued
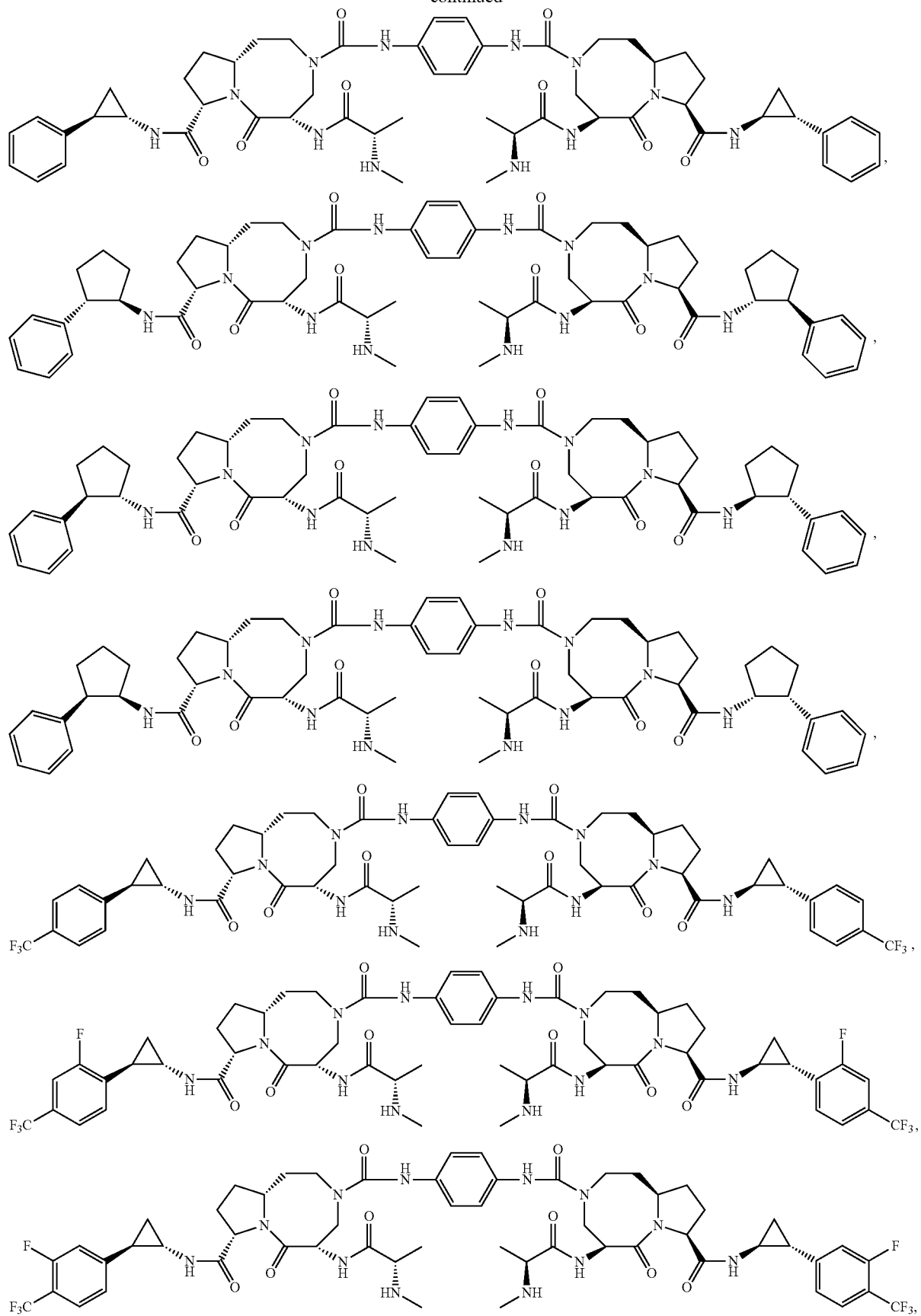

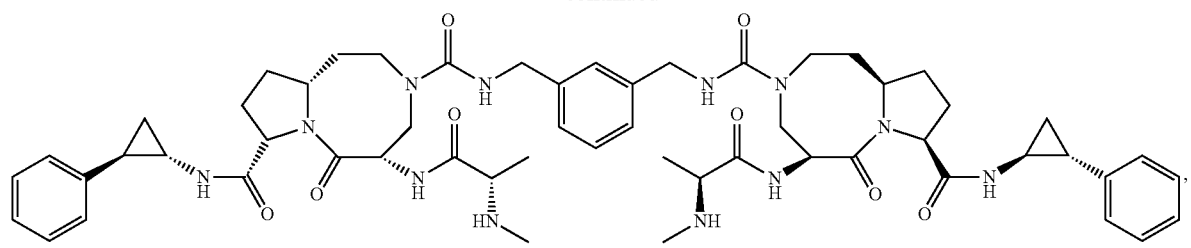
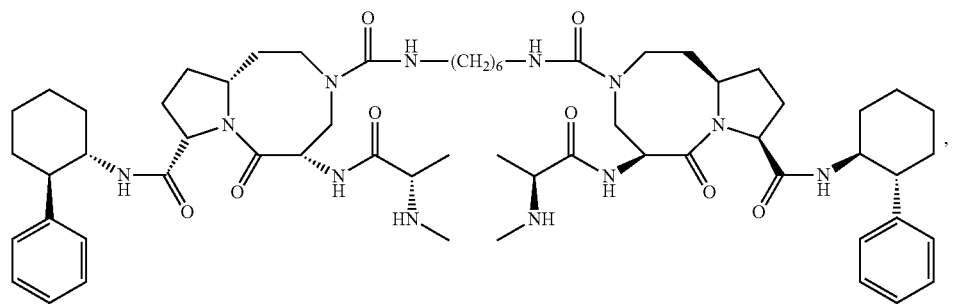
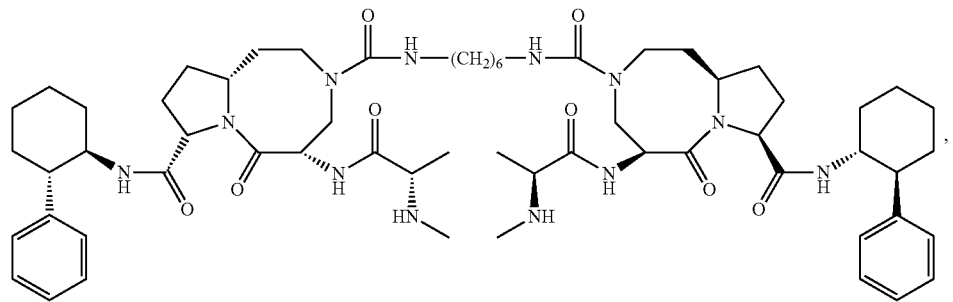
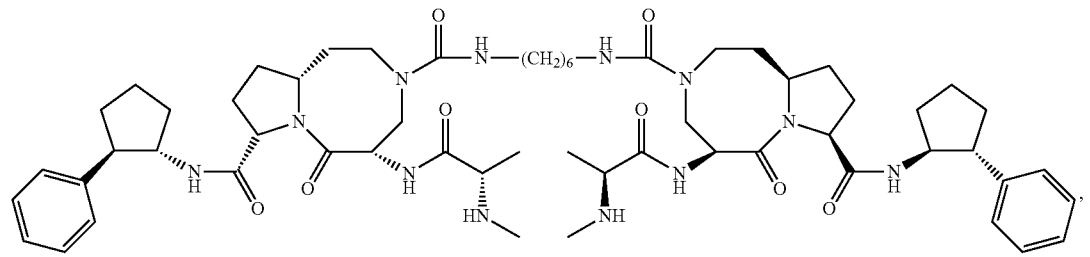
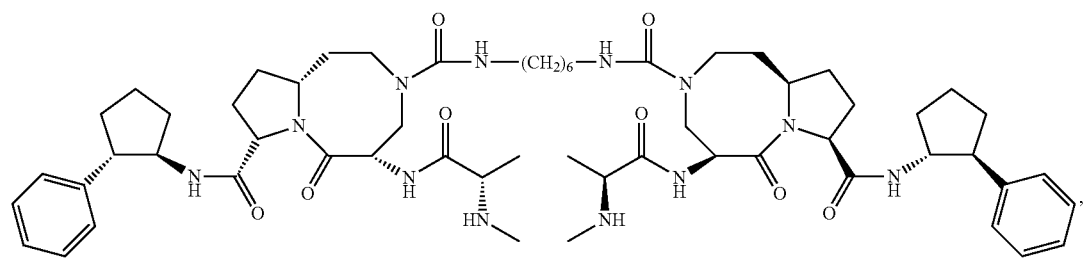
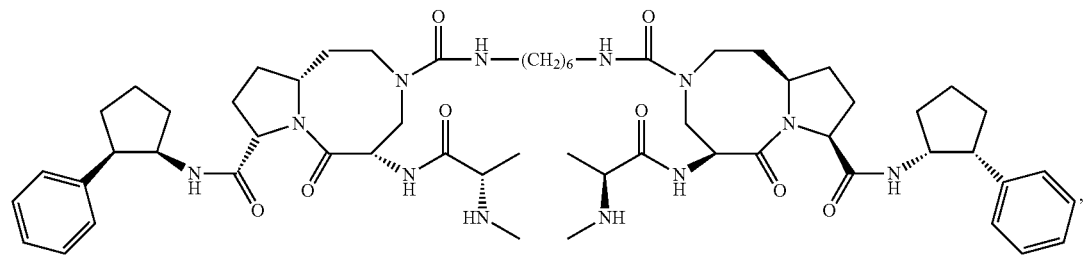

-continued
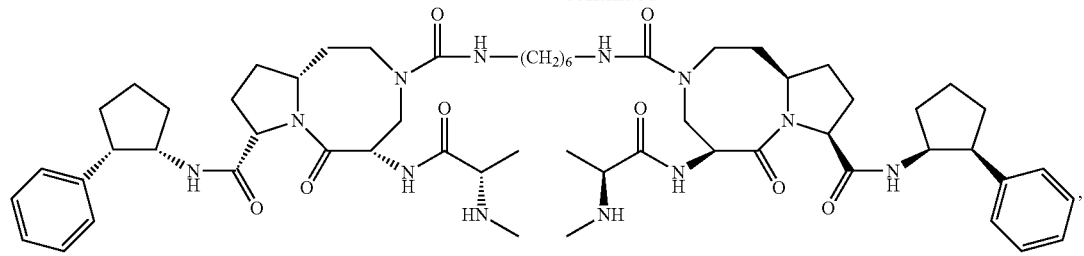
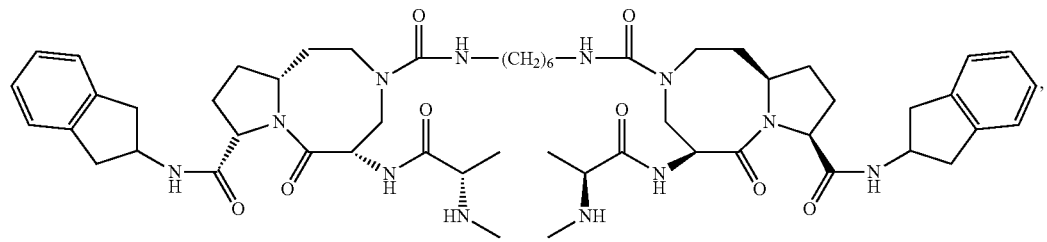
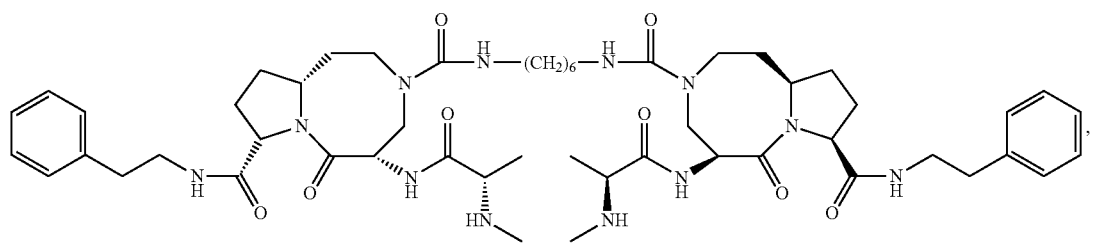
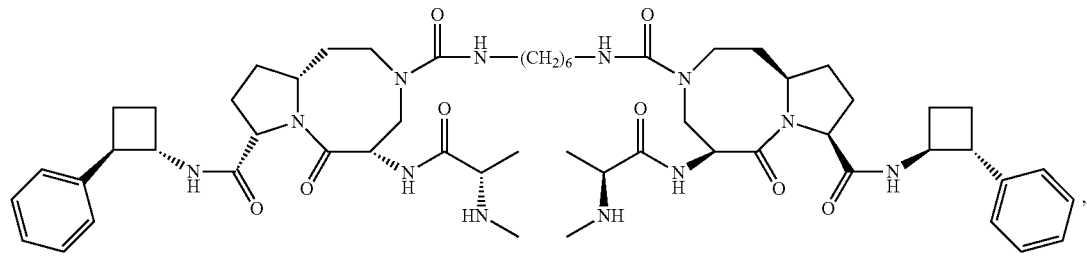
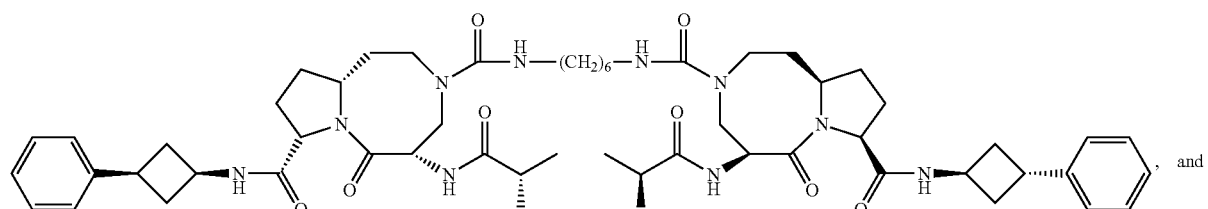, and
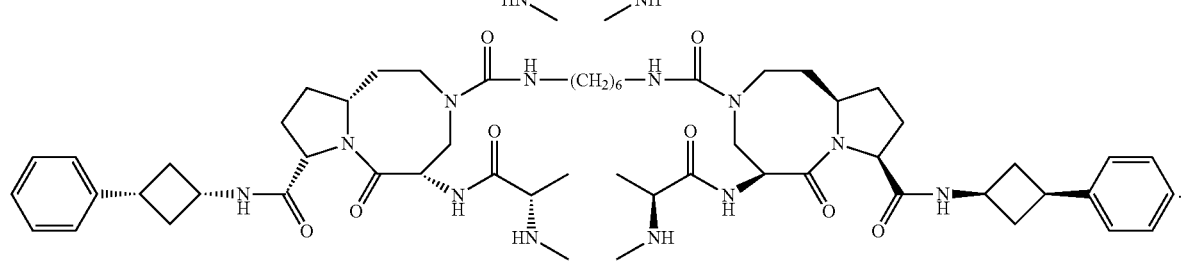.

11. A compound selected from the group consisting of

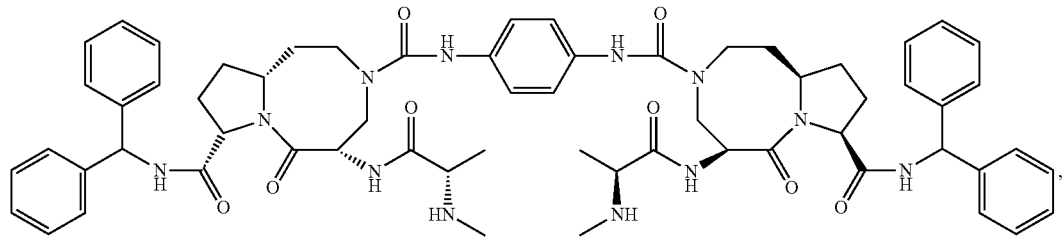

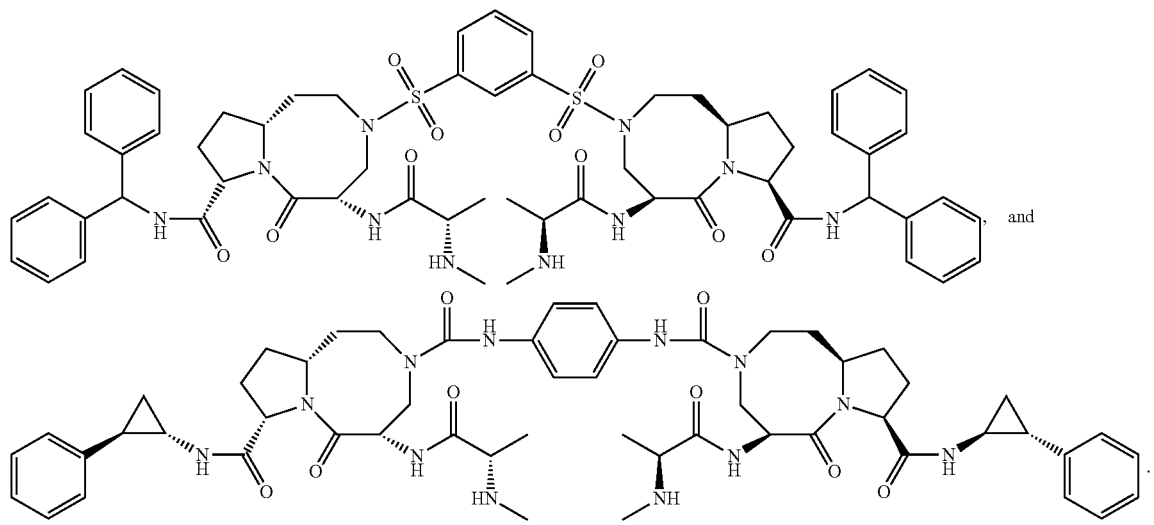

, and

12. A pharmaceutical composition comprising a compound of claim 1 and a pharmaceutically acceptable carrier or vehicle.

13. A method of treating a breast cancer or an ovarian cell line cancer comprising administering a therapeutically effective amount of a compound of claim 1 to an individual in need thereof.

14. The method of claim 13 further comprising administering a therapeutically effective amount of a second therapeutic agent useful in the treatment of the breast cancer or ovarian cell line cancer.

15. The method of claim 14 wherein the compound of claim 1 and the second therapeutic agent are administered simultaneously.

16. The method of claim 14 wherein the compound of claim 1 and the second therapeutic agent are administered separately.

17. The method of claim 14 wherein the second therapeutic agent is one or more of a chemotherapeutic agent and radiation.

18. The method of claim 14 wherein the compound of claim 1 and the second therapeutic agent are administered from a single composition.

19. The method of claim 14 wherein the compound of claim 1 and the second therapeutic agent are administered from separate compositions.

20. The method of claim 14 wherein the compound of claim 1 is administered prior to the second therapeutic agent.

21. The method of claim 14 wherein the compound of claim 1 is administered after the second therapeutic agent.

22. A compound having a structure

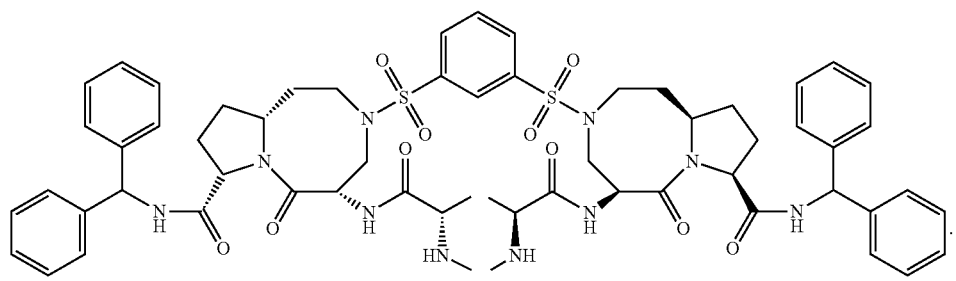

.

* * * * *

UNITED STATES PATENT AND TRADEMARK OFFICE
CERTIFICATE OF CORRECTION

PATENT NO. : 8,883,771 B2
APPLICATION NO. : 13/969030
DATED : November 11, 2014
INVENTOR(S) : Shaomeng Wang et al.

It is certified that error appears in the above-identified patent and that said Letters Patent is hereby corrected as shown below:

In the Claims:

At Column 150, line 43, Claim 1, "aliphatic ring" should be -- aliphatic ring, --.

At Column 152, line 35, Claim 4, " 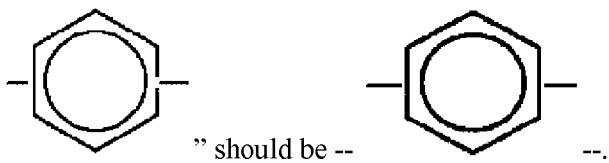 " should be -- --.

At Column 152, line 40, Claim 4, " 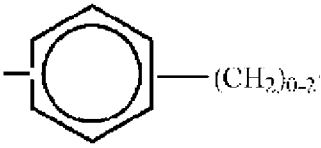 " should be

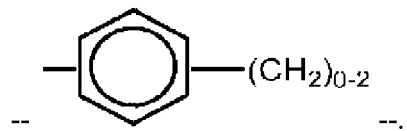 -- --.

At Column 154, line 13, Claim 8, " 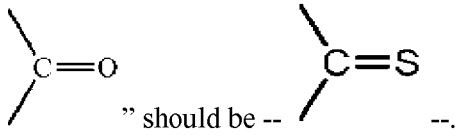 " should be -- --.

At Column 154, line 22, Claim 8, " 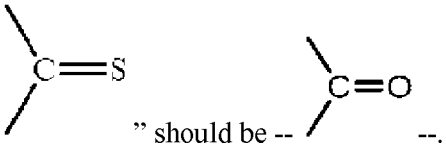 " should be -- --.

Signed and Sealed this
Eighth Day of December, 2015

Michelle K. Lee
*Director of the United States Patent and Trademark Office*